United States Patent
Bui et al.

(10) Patent No.: US 10,295,444 B2
(45) Date of Patent: May 21, 2019

(54) AUTOMATED STAINING SYSTEM AND REACTION CHAMBER

(71) Applicant: Sakura Finetek U.S.A., Inc., Torrance, CA (US)

(72) Inventors: Xuan S. Bui, Torrance, CA (US); Anthony L. Hartman, Tucson, AZ (US); Toshiyuki Fujimaki, Nagano (JP); Shinji Tokudaiji, Nagano (JP); Yoshitake Okabe, Higashichikuma-gun (JP); Yoshitada Mizusawa, Nagano (JP)

(73) Assignee: Sakura Finetek U.S.A., Inc., Torrance, CA (US)

( * ) Notice: Subject to any disclaimer, the term of this patent is extended or adjusted under 35 U.S.C. 154(b) by 498 days.

(21) Appl. No.: 14/579,858

(22) Filed: Dec. 22, 2014

(65) Prior Publication Data

US 2015/0111202 A1    Apr. 23, 2015

Related U.S. Application Data

(62) Division of application No. 13/238,511, filed on Sep. 21, 2011, now Pat. No. 8,932,543.

(51) Int. Cl.
*G01N 1/31*    (2006.01)
*G01N 35/00*    (2006.01)
(Continued)

(52) U.S. Cl.
CPC .......... *G01N 1/31* (2013.01); *B01L 3/502715* (2013.01); *B01L 9/52* (2013.01);
(Continued)

(58) Field of Classification Search
CPC ....................................................... B01L 3/52
See application file for complete search history.

(56) References Cited

U.S. PATENT DOCUMENTS

| 1,621,097 A | 3/1927 | Zammataro |
| 2,709,025 A | 5/1955 | Scott |

(Continued)

FOREIGN PATENT DOCUMENTS

| AU | 2004266226 | 3/2005 |
| CN | 2390207 | 8/2000 |

(Continued)

OTHER PUBLICATIONS

Sakura Finetek, Non-Final Office Action dated Jan. 25, 2013 for U.S. Appl. No. 13/238,575.

(Continued)

*Primary Examiner* — Kathryn Wright
(74) *Attorney, Agent, or Firm* — William Thomas Babbitt; Leech Tishman Fusclado & Lampl

(57) ABSTRACT

An apparatus including a reagent cartridge and a reaction chamber, the reagent cartridge having a reagent capsule removably positioned therein for dispensing of a reagent onto the reaction chamber. A system including a linearly translatable mounting assembly having a plurality of mounting stations dimensioned to receive at least one fluid dispensing cartridge, a linearly translatable bulk reagent dispensing assembly having a plurality of bulk reagent dispensing nozzles coupled thereto and a receiving assembly positioned beneath the mounting assembly and the bulk reagent dispensing assembly, the receiving assembly including a plurality of reaction stations. A method including determining an inventory of an automated sample processing system, downloading a processing protocol from a central controller to the automated sample processing system, operating the automated sample processing system based on the processing protocol and independently of the central controller and dispensing a reagent from the automated sample processing system.

10 Claims, 29 Drawing Sheets

(51) Int. Cl.
  *G01N 35/02* (2006.01)
  *B01L 3/00* (2006.01)
  *B01L 9/00* (2006.01)
(52) U.S. Cl.
  CPC ....... *G01N 35/00732* (2013.01); *G01N 35/02* (2013.01); *B01L 2300/0822* (2013.01); *B01L 2300/0877* (2013.01); *B01L 2400/0409* (2013.01); *B01L 2400/0478* (2013.01); *G01N 2035/00752* (2013.01); *G01N 2035/00831* (2013.01); *G01N 2035/00851* (2013.01); *Y10T 436/11* (2015.01); *Y10T 436/112499* (2015.01)

(56) References Cited

U.S. PATENT DOCUMENTS

| | | |
|---|---|---|
| 2,772,817 A | 12/1956 | Jauch |
| 3,008,611 A | 11/1961 | Mancusi, Jr. |
| 3,066,832 A | 12/1962 | Rossetti |
| 3,116,747 A | 1/1964 | Cowles et al. |
| 3,232,496 A | 2/1966 | Rockwell, Jr. et al. |
| 3,294,290 A | 12/1966 | Erickson et al. |
| 3,504,699 A | 4/1970 | Grise |
| 3,741,439 A | 6/1973 | Vehrs |
| 3,752,366 A | 8/1973 | Lawrence, Jr. |
| 3,794,213 A | 2/1974 | Schwartzman |
| 3,870,201 A | 3/1975 | Asplund |
| 3,881,641 A | 5/1975 | Pliml, Jr. et al. |
| 3,904,079 A | 9/1975 | Kross |
| 3,987,938 A | 10/1976 | Cooprider et al. |
| 4,018,363 A | 4/1977 | Cassia |
| 4,025,241 A | 5/1977 | Clemens |
| 4,039,775 A | 8/1977 | Andra |
| 4,067,414 A | 1/1978 | Funke |
| 4,099,483 A | 7/1978 | Henderson |
| 4,130,224 A | 12/1978 | Norman et al. |
| 4,134,853 A | 1/1979 | Ehrlich et al. |
| 4,135,649 A | 1/1979 | Baldwin et al. |
| 4,149,573 A | 4/1979 | Cassia |
| 4,149,633 A | 4/1979 | Nilson |
| 4,199,558 A | 4/1980 | Henderson |
| 4,256,242 A | 3/1981 | Christine |
| 4,258,759 A | 3/1981 | Achen |
| 4,334,640 A | 6/1982 | van Overbruggen et al. |
| 4,345,627 A | 8/1982 | Cassia |
| 4,349,133 A | 9/1982 | Christine |
| 4,356,727 A | 11/1982 | Brown et al. |
| 4,394,938 A | 7/1983 | Frassanito |
| 4,440,323 A | 4/1984 | Benson |
| 4,513,885 A | 4/1985 | Hogan |
| 4,515,294 A | 5/1985 | Udall |
| 4,561,571 A | 12/1985 | Chen |
| 4,573,612 A | 3/1986 | Maddison et al. |
| 4,601,411 A | 7/1986 | van Overbruggen |
| 4,604,964 A | 8/1986 | Gordon et al. |
| 4,607,764 A | 8/1986 | Christine |
| 4,615,476 A | 10/1986 | Hobbs et al. |
| 4,621,749 A | 11/1986 | Kanfer |
| 4,646,945 A | 3/1987 | Steiner et al. |
| 4,651,898 A | 3/1987 | Bell |
| 4,667,854 A | 5/1987 | McDermott et al. |
| 4,673,109 A | 6/1987 | Cassia |
| 4,678,752 A | 7/1987 | Thorne et al. |
| 4,722,372 A | 2/1988 | Hoffman et al. |
| 4,731,335 A | 3/1988 | Brigati |
| 4,741,461 A | 5/1988 | Williamson et al. |
| 4,741,898 A | 5/1988 | Mallik et al. |
| 4,764,342 A | 8/1988 | Kelln et al. |
| 4,776,495 A | 10/1988 | Vignot |
| 4,790,640 A | 12/1988 | Nason |
| 4,798,311 A | 1/1989 | Workum |
| 4,801,431 A | 1/1989 | Cuomo et al. |
| 4,834,019 A | 5/1989 | Gordon et al. |
| 4,838,457 A | 6/1989 | Swahl et al. |
| 4,846,636 A | 7/1989 | Danby et al. |
| 4,849,176 A | 7/1989 | Sakagami |
| 4,867,347 A | 9/1989 | Wass et al. |
| 4,880,149 A | 11/1989 | Scholefield et al. |
| 4,886,192 A | 12/1989 | Cassia |
| 4,895,276 A | 1/1990 | Maldonado |
| 4,917,265 A | 4/1990 | Chiang |
| 4,921,136 A | 5/1990 | Roggenburg, Jr. |
| 4,927,061 A | 5/1990 | Leigh et al. |
| 4,932,624 A | 6/1990 | Holm |
| 4,946,076 A | 8/1990 | Hackmann et al. |
| 4,955,512 A | 9/1990 | Sharples |
| 4,961,508 A | 10/1990 | Weimer et al. |
| 4,967,940 A | 11/1990 | Blette et al. |
| 4,969,581 A | 11/1990 | Seifert et al. |
| 4,972,978 A | 11/1990 | DeLuca |
| 4,974,754 A | 12/1990 | Wirz |
| 4,978,036 A | 12/1990 | Burd |
| 4,978,502 A | 12/1990 | Dole et al. |
| 4,985,206 A | 1/1991 | Bowman et al. |
| 5,002,736 A | 3/1991 | Babbitt et al. |
| 5,033,656 A | 7/1991 | Blette et al. |
| 5,033,943 A | 7/1991 | Durrum et al. |
| 5,035,350 A | 7/1991 | Blette et al. |
| 5,042,691 A | 8/1991 | Maldonado |
| 5,068,091 A | 11/1991 | Toya |
| 5,073,504 A | 12/1991 | Bogen |
| 5,082,150 A | 1/1992 | Steiner et al. |
| 5,105,992 A | 4/1992 | Fender et al. |
| 5,225,325 A | 7/1993 | Miller et al. |
| 5,232,664 A | 8/1993 | Krawzak et al. |
| 5,242,081 A | 9/1993 | van der Heyden et al. |
| 5,242,083 A | 9/1993 | Christine et al. |
| 5,244,787 A | 9/1993 | Key et al. |
| 5,252,293 A | 10/1993 | Drbal et al. |
| 5,253,774 A | 10/1993 | Honig et al. |
| 5,255,822 A | 10/1993 | Mease et al. |
| 5,265,770 A | 11/1993 | Matkovich et al. |
| 5,273,905 A | 12/1993 | Muller et al. |
| 5,275,309 A | 1/1994 | Baron et al. |
| 5,316,452 A | 5/1994 | Bogen et al. |
| 5,322,771 A | 6/1994 | Rybski et al. |
| 5,338,358 A | 8/1994 | Mizusawa et al. |
| 5,355,439 A | 10/1994 | Bernstein et al. |
| 5,356,039 A | 10/1994 | Christine et al. |
| 5,390,822 A | 2/1995 | Lataix |
| 5,405,580 A * | 4/1995 | Palmer ................ A61L 2/28 |
| | | 206/569 |
| 5,418,138 A | 5/1995 | Miller et al. |
| 5,421,489 A | 6/1995 | Holzner, Sr. et al. |
| 5,424,036 A | 6/1995 | Ushikubo |
| 5,425,918 A | 6/1995 | Healey et al. |
| 5,433,351 A | 7/1995 | Okuyama et al. |
| 5,439,645 A | 8/1995 | Saralegui et al. |
| 5,439,649 A | 8/1995 | Tseung et al. |
| 5,464,125 A | 11/1995 | Daansen |
| 5,474,212 A | 12/1995 | Ichikawa et al. |
| 5,492,247 A | 2/1996 | Shu et al. |
| 5,501,372 A | 3/1996 | Daansen |
| 5,525,300 A | 6/1996 | Danssaert et al. |
| 5,534,114 A | 7/1996 | Cutright et al. |
| 5,561,556 A | 10/1996 | Weissman et al. |
| 5,578,452 A | 11/1996 | Shi et al. |
| 5,579,945 A | 12/1996 | Ichikawa et al. |
| 5,580,523 A | 12/1996 | Bard |
| 5,595,707 A | 1/1997 | Copeland et al. |
| 5,597,093 A | 1/1997 | Lee |
| 5,602,674 A | 2/1997 | Weissman et al. |
| 5,609,822 A | 3/1997 | Carey et al. |
| 5,626,262 A | 5/1997 | Fitten et al. |
| 5,639,423 A | 6/1997 | Northrup et al. |
| 5,645,114 A | 7/1997 | Bogen et al. |
| 5,650,327 A | 7/1997 | Copeland et al. |
| 5,654,199 A | 8/1997 | Copeland et al. |
| 5,654,200 A | 8/1997 | Copeland et al. |
| 5,675,715 A | 10/1997 | Bernstein et al. |
| 5,700,346 A | 12/1997 | Edwards |
| 5,810,204 A | 9/1998 | Devlin et al. |
| 5,819,842 A | 10/1998 | Potter et al. |
| 5,836,482 A | 11/1998 | Ophardt et al. |

(56) References Cited

U.S. PATENT DOCUMENTS

| | | |
|---|---|---|
| 5,839,091 A | 11/1998 | Rhett et al. |
| 5,843,700 A | 12/1998 | Kerrod et al. |
| 5,846,396 A | 12/1998 | Zanzucchi et al. |
| 5,851,488 A | 12/1998 | Saul et al. |
| 5,855,302 A | 1/1999 | Fisscher |
| 5,857,595 A | 1/1999 | Nilson |
| 5,885,530 A | 3/1999 | Babson et al. |
| 5,909,828 A | 6/1999 | Salisbury |
| 5,938,414 A | 8/1999 | Kayahara et al. |
| 5,947,167 A | 9/1999 | Bogen et al. |
| 5,948,359 A | 9/1999 | Kalra et al. |
| 5,950,874 A | 9/1999 | Sindoni |
| 5,950,878 A | 9/1999 | Wade et al. |
| 5,954,167 A | 9/1999 | Richardson et al. |
| 5,958,341 A | 9/1999 | Chu |
| 5,964,454 A | 10/1999 | Volpel |
| 5,965,454 A | 10/1999 | Farmilo et al. |
| 5,968,731 A | 10/1999 | Layne et al. |
| 5,971,223 A | 10/1999 | Fisscher |
| 6,001,309 A | 12/1999 | Gamble et al. |
| 6,012,613 A | 1/2000 | Chen |
| 6,017,495 A | 1/2000 | Ljungmann |
| 6,020,995 A | 2/2000 | Dreyer et al. |
| 6,045,759 A | 4/2000 | Ford et al. |
| 6,068,162 A | 5/2000 | De Winter et al. |
| 6,076,583 A | 6/2000 | Edwards |
| 6,092,695 A | 7/2000 | Loeffler |
| 6,093,574 A | 7/2000 | Druyor-Sanchez et al. |
| 6,096,271 A | 8/2000 | Bogen et al. |
| 6,131,773 A | 10/2000 | Wade et al. |
| 6,142,343 A | 11/2000 | Wade et al. |
| 6,152,330 A | 11/2000 | Polan |
| 6,180,061 B1 | 1/2001 | Bogen et al. |
| 6,183,693 B1 | 2/2001 | Bogen et al. |
| 6,189,740 B1 | 2/2001 | Wade et al. |
| 6,192,945 B1 | 2/2001 | Ford et al. |
| 6,206,238 B1 | 3/2001 | Ophardt |
| 6,216,916 B1 | 4/2001 | Maddox et al. |
| 6,238,910 B1 | 5/2001 | Custance et al. |
| 6,244,474 B1 | 6/2001 | Loeffler |
| 6,259,956 B1 | 7/2001 | Myers et al. |
| 6,273,298 B1 | 8/2001 | Post |
| 6,286,725 B1 | 9/2001 | Gerber |
| 6,296,809 B1 | 10/2001 | Richards et al. |
| 6,335,166 B1 | 1/2002 | Ammann et al. |
| 6,343,716 B1 | 2/2002 | Baudin et al. |
| 6,349,264 B1 | 2/2002 | Rhett et al. |
| 6,352,861 B1 | 3/2002 | Copeland et al. |
| 6,387,326 B1 | 5/2002 | Edwards et al. |
| 6,415,961 B2 | 7/2002 | Bonnigue |
| 6,416,713 B1 | 7/2002 | Ford et al. |
| 6,451,551 B1 | 9/2002 | Zhan et al. |
| 6,472,217 B1 | 10/2002 | Richards et al. |
| 6,489,171 B1 | 12/2002 | Aghassi et al. |
| 6,495,106 B1 | 12/2002 | Kalra et al. |
| 6,516,620 B2 | 2/2003 | Lang |
| 6,534,008 B1 | 3/2003 | Angros |
| 6,540,117 B2 | 4/2003 | Powling |
| 6,541,261 B1 | 4/2003 | Bogen et al. |
| 6,543,652 B1 | 4/2003 | Kelder et al. |
| 6,544,798 B1 | 4/2003 | Christensen et al. |
| 6,553,145 B1 | 4/2003 | Kang et al. |
| 6,568,561 B2 | 5/2003 | Studer et al. |
| 6,580,056 B1 | 6/2003 | Tacha |
| 6,582,962 B1 | 6/2003 | Richards et al. |
| 6,594,537 B1 | 7/2003 | Bernstein et al. |
| 6,605,213 B1 | 8/2003 | Ammann et al. |
| 6,607,103 B2 | 8/2003 | Gerenraich et al. |
| 6,632,598 B1 | 10/2003 | Zhang et al. |
| 6,635,225 B1 | 10/2003 | Thiem et al. |
| 6,656,428 B1 | 12/2003 | Clark et al. |
| 6,673,620 B1 | 1/2004 | Loeffler et al. |
| 6,703,247 B1 | 3/2004 | Chu |
| 6,707,873 B2 | 3/2004 | Thompson et al. |
| 6,720,888 B2 | 4/2004 | Eagleson et al. |
| 6,729,502 B2 | 5/2004 | Lewis et al. |
| 6,735,531 B2 | 5/2004 | Rhett et al. |
| 6,746,851 B1 | 6/2004 | Tseung et al. |
| 6,758,360 B2 | 7/2004 | Van Giezen et al. |
| 6,783,733 B2 | 8/2004 | Bogen et al. |
| 6,805,264 B2 | 10/2004 | Houvras |
| 6,814,262 B1 | 11/2004 | Adams et al. |
| 6,827,900 B2 | 12/2004 | Thiem et al. |
| 6,827,901 B2 | 12/2004 | Copeland et al. |
| 6,855,292 B2 | 2/2005 | Angros |
| 6,855,552 B2 | 2/2005 | Towne et al. |
| 6,855,559 B1 | 2/2005 | Christensen et al. |
| 6,899,283 B2 | 5/2005 | Ohnishi et al. |
| 6,943,029 B2 | 9/2005 | Copeland et al. |
| 6,945,128 B2 | 9/2005 | Ford et al. |
| 6,991,934 B2 | 1/2006 | Walton et al. |
| 6,998,270 B2 | 2/2006 | Tseung et al. |
| 7,004,356 B1 | 2/2006 | Sayers |
| 7,007,824 B2 | 3/2006 | Danby et al. |
| 7,025,937 B2 | 4/2006 | Plank |
| 7,057,808 B2 | 6/2006 | Dooling |
| 7,070,951 B2 | 7/2006 | Zhang et al. |
| 7,083,106 B2 | 8/2006 | Albany |
| 7,118,918 B2 | 10/2006 | Copeland et al. |
| 7,156,814 B1 | 1/2007 | Williamson et al. |
| 7,165,722 B2 | 1/2007 | Shafer et al. |
| 7,169,601 B1 | 1/2007 | Northrup |
| 7,178,416 B2 | 2/2007 | Whelan et al. |
| 7,179,424 B2 | 2/2007 | Williamson, IV et al. |
| 7,187,286 B2 | 3/2007 | Morris et al. |
| 7,199,712 B2 | 4/2007 | Tafas et al. |
| 7,201,295 B1 | 4/2007 | Sitzberger |
| 7,209,042 B2 | 4/2007 | Martin et al. |
| 7,217,392 B2 | 5/2007 | Bogen et al. |
| 7,220,589 B2 | 5/2007 | Richards et al. |
| 7,226,788 B2 | 6/2007 | De La Torre-Bueno |
| 7,233,250 B2 | 6/2007 | Forster |
| 7,250,301 B2 | 7/2007 | Angros |
| 7,264,142 B2 | 9/2007 | Py |
| 7,270,785 B1 | 9/2007 | Lemme et al. |
| 7,275,682 B2 | 10/2007 | Excoffier et al. |
| 7,278,554 B2 | 10/2007 | Armstrong |
| 7,294,478 B1 | 11/2007 | Hinchcliffe |
| 7,303,725 B2 | 12/2007 | Reinhardt et al. |
| 7,314,238 B2 | 1/2008 | Robert |
| 7,323,491 B2 | 1/2008 | Lohray et al. |
| 7,338,803 B2 | 3/2008 | Mizzer et al. |
| 7,378,055 B2 | 5/2008 | Lemme et al. |
| 7,382,258 B2 | 6/2008 | Oldham et al. |
| 7,395,974 B2 | 7/2008 | Albany |
| 7,400,983 B2 | 7/2008 | Feingold et al. |
| 7,405,056 B2 | 7/2008 | Lam et al. |
| 7,425,306 B1 | 9/2008 | Kram |
| 7,435,381 B2 | 10/2008 | Pugia et al. |
| 7,435,383 B2 | 10/2008 | Tseung et al. |
| 7,468,161 B2 | 12/2008 | Reinhardt et al. |
| 7,470,401 B2 | 12/2008 | Morales |
| 7,470,541 B2 | 12/2008 | Copeland et al. |
| 7,476,362 B2 | 1/2009 | Angros |
| 7,501,283 B2 | 3/2009 | Hersch et al. |
| 7,553,672 B2 | 6/2009 | Bogen |
| 7,584,019 B2 | 9/2009 | Feingold et al. |
| 7,593,787 B2 | 9/2009 | Feingold et al. |
| 7,603,201 B2 | 10/2009 | Feingold et al. |
| 7,622,077 B2 | 11/2009 | Angros |
| 7,632,461 B2 | 12/2009 | Angros |
| 7,639,139 B2 | 12/2009 | Tafas et al. |
| 7,642,093 B2 | 1/2010 | Tseung et al. |
| 7,651,010 B2 | 1/2010 | Orzech et al. |
| 7,665,360 B2 | 2/2010 | McGill |
| 7,677,417 B2 | 3/2010 | Leiner et al. |
| 7,718,435 B2 | 5/2010 | Bogen et al. |
| 7,722,811 B2 | 5/2010 | Konrad et al. |
| 7,735,694 B2 | 6/2010 | Brown et al. |
| 7,744,817 B2 | 6/2010 | Bui |
| 7,760,428 B2 | 7/2010 | Sieckmann |
| 7,806,301 B1 | 10/2010 | Clavarella et al. |
| 7,838,283 B2 | 11/2010 | Erickson et al. |
| 7,850,912 B2 | 12/2010 | Favuzzi et al. |

(56) References Cited

U.S. PATENT DOCUMENTS

| | | | |
|---|---|---|---|
| 7,861,890 B2 | 1/2011 | McGill |
| 7,880,617 B2 | 2/2011 | Morris et al. |
| 7,887,755 B2 | 2/2011 | Mingerink et al. |
| 7,897,106 B2 | 3/2011 | Angros |
| 7,901,941 B2 | 3/2011 | Tseung et al. |
| 7,922,986 B2 | 4/2011 | Byrnard et al. |
| 7,937,228 B2 | 5/2011 | Feingold et al. |
| 7,951,612 B2 | 5/2011 | Angros |
| 7,960,178 B2 | 6/2011 | Key et al. |
| 7,980,425 B2 | 7/2011 | Baron et al. |
| 8,007,720 B2 | 8/2011 | Angros |
| 8,007,721 B2 | 8/2011 | Angros |
| 8,039,262 B2 | 10/2011 | Konrad et al. |
| 8,052,927 B2 | 11/2011 | Angros |
| 8,058,010 B2 | 11/2011 | Erickson et al. |
| 8,071,023 B2 | 12/2011 | Angros |
| 8,071,026 B2 | 12/2011 | Rapp et al. |
| 8,092,742 B2 | 1/2012 | Angros |
| 8,118,183 B2 | 2/2012 | Iwahashi et al. |
| 8,137,619 B2 | 3/2012 | Ford et al. |
| 8,142,739 B2 | 3/2012 | Tseung et al. |
| 8,216,846 B2 | 7/2012 | Ljungmann et al. |
| 8,236,255 B2 | 8/2012 | Takayama et al. |
| 8,257,968 B2 | 9/2012 | Sweet et al. |
| 8,283,176 B2 | 10/2012 | Bland et al. |
| 8,288,086 B2 | 10/2012 | Metzner et al. |
| 8,298,815 B2 | 10/2012 | Buchanan et al. |
| 8,315,899 B2 | 11/2012 | Samuhel et al. |
| 8,386,195 B2 | 2/2013 | Feingold |
| 8,394,322 B2 | 3/2013 | Windeyer et al. |
| 8,394,635 B2 | 3/2013 | Key et al. |
| 8,396,669 B2 | 3/2013 | Cocks |
| 8,486,714 B2 | 7/2013 | Favuzzi et al. |
| 8,529,836 B2 | 9/2013 | Winther et al. |
| 8,554,372 B2 | 10/2013 | Windeyer et al. |
| 8,585,985 B2 | 11/2013 | Lihl et al. |
| 8,609,023 B1 | 12/2013 | Druyor-Sanchez et al. |
| 8,663,978 B2 | 3/2014 | Sweet et al. |
| 8,673,642 B2 | 3/2014 | Key et al. |
| 8,676,509 B2 | 3/2014 | De La Torre-Bueno |
| 8,887,964 B2 | 11/2014 | Jokitalo et al. |
| 8,969,086 B2 | 3/2015 | Key et al. |
| 8,969,087 B2 | 3/2015 | Bland et al. |
| 2001/0044603 A1 | 11/2001 | Harold |
| 2002/0013194 A1 | 1/2002 | Kitano et al. |
| 2002/0079318 A1 | 6/2002 | Wurzinger |
| 2002/0110494 A1 | 8/2002 | Lemme et al. |
| 2002/0114733 A1 | 8/2002 | Copeland et al. |
| 2002/0182115 A1 | 12/2002 | Aghassi et al. |
| 2002/0192806 A1 | 12/2002 | Custance et al. |
| 2003/0100043 A1 | 5/2003 | Kalra et al. |
| 2003/0157545 A1 | 8/2003 | Jevons et al. |
| 2003/0203493 A1 | 10/2003 | Lemme et al. |
| 2004/0033163 A1 | 2/2004 | Tseung et al. |
| 2004/0033169 A1 | 2/2004 | Shah |
| 2004/0091395 A1 | 5/2004 | Ward et al. |
| 2004/0120862 A1 | 6/2004 | Lang et al. |
| 2004/0191128 A1 | 9/2004 | Bogen et al. |
| 2004/0197230 A1 | 10/2004 | Lemme et al. |
| 2004/0266015 A1 | 12/2004 | Favuzzi et al. |
| 2005/0019902 A1 | 1/2005 | Mathies et al. |
| 2005/0035156 A1 | 2/2005 | Hersch et al. |
| 2005/0064535 A1 | 3/2005 | Favuzzi et al. |
| 2005/0135972 A1 | 6/2005 | Lemme et al. |
| 2005/0150911 A1 | 7/2005 | Bach |
| 2005/0153453 A1 | 7/2005 | Copeland et al. |
| 2005/0164374 A1 | 7/2005 | Kram |
| 2005/0186114 A1 | 8/2005 | Reinhardt et al. |
| 2005/0191214 A1 | 9/2005 | Tseung et al. |
| 2005/0250211 A1 | 11/2005 | Reinhardt et al. |
| 2005/0272159 A1* | 12/2005 | Ismagilov ............ B01F 5/0646 436/34 |
| 2005/0281711 A1 | 12/2005 | Testa et al. |
| 2006/0019332 A1 | 1/2006 | Zhang et al. |
| 2006/0040341 A1 | 2/2006 | Bland et al. |
| 2006/0045806 A1 | 3/2006 | Winther et al. |
| 2006/0049208 A1 | 3/2006 | Daansen |
| 2006/0063265 A1 | 3/2006 | Welcher et al. |
| 2006/0088928 A1 | 4/2006 | Sweet et al. |
| 2006/0088940 A1 | 4/2006 | Feingold et al. |
| 2006/0105359 A1 | 5/2006 | Favuzzi et al. |
| 2006/0120921 A1 | 6/2006 | Elliot et al. |
| 2006/0127283 A1 | 6/2006 | Tseung et al. |
| 2006/0134793 A1 | 6/2006 | Key et al. |
| 2006/0147351 A1 | 7/2006 | Falb et al. |
| 2006/0148063 A1 | 7/2006 | Fauzzi et al. |
| 2006/0151051 A1 | 7/2006 | Py et al. |
| 2006/0169719 A1 | 8/2006 | Bui |
| 2006/0171857 A1 | 8/2006 | Stead et al. |
| 2006/0172426 A1 | 8/2006 | Buchanan |
| 2006/0173575 A1 | 8/2006 | Lefebvre et al. |
| 2006/0178776 A1 | 8/2006 | Feingold et al. |
| 2006/0190185 A1 | 8/2006 | Ford et al. |
| 2006/0191952 A1 | 8/2006 | Kalra et al. |
| 2006/0239858 A1 | 10/2006 | Becker |
| 2006/0252025 A1 | 11/2006 | Nitta et al. |
| 2006/0263268 A9 | 11/2006 | Tseung et al. |
| 2006/0265133 A1 | 11/2006 | Cocks et al. |
| 2006/0269985 A1 | 11/2006 | Kitayama |
| 2006/0275889 A1 | 12/2006 | Angros et al. |
| 2007/0010912 A1 | 1/2007 | Feingold et al. |
| 2007/0038491 A1 | 2/2007 | Samuhel et al. |
| 2007/0068969 A1 | 3/2007 | Orzech et al. |
| 2007/0160494 A1 | 7/2007 | Sands |
| 2007/0270714 A1 | 11/2007 | Cushner et al. |
| 2007/0272710 A1 | 11/2007 | Bui |
| 2008/0035677 A1 | 2/2008 | Daansen |
| 2008/0102006 A1 | 5/2008 | Kram et al. |
| 2008/0118378 A1 | 5/2008 | Baron et al. |
| 2008/0135583 A1 | 6/2008 | Caswell et al. |
| 2008/0215625 A1 | 9/2008 | Veitch et al. |
| 2008/0217246 A1 | 9/2008 | Benn et al. |
| 2008/0226508 A1 | 9/2008 | Byrnard et al. |
| 2008/0235055 A1 | 9/2008 | Mattingly et al. |
| 2008/0254503 A1 | 10/2008 | Ljungmann et al. |
| 2008/0286753 A1 | 11/2008 | Erickson et al. |
| 2008/0305515 A1 | 12/2008 | Burgart et al. |
| 2009/0004691 A1 | 1/2009 | Erickson et al. |
| 2009/0028757 A1 | 1/2009 | Lihl et al. |
| 2009/0108033 A1 | 4/2009 | Quinn et al. |
| 2009/0241751 A1 | 10/2009 | Walter |
| 2009/0298129 A1* | 12/2009 | Spence ............... B01L 3/0293 435/91.2 |
| 2009/0308887 A1 | 12/2009 | Woo et al. |
| 2009/0325309 A1 | 12/2009 | Favuzzi et al. |
| 2010/0017030 A1 | 1/2010 | Feingold et al. |
| 2010/0028978 A1 | 2/2010 | Angros |
| 2010/0068757 A1 | 3/2010 | Angros |
| 2010/0089921 A1 | 4/2010 | Ellenkamp-Van Olst et al. |
| 2010/0099133 A1 | 4/2010 | Egle et al. |
| 2010/0178668 A1 | 7/2010 | Elliot et al. |
| 2011/0056991 A1 | 3/2011 | Brown et al. |
| 2011/0079615 A1 | 4/2011 | Ophardt et al. |
| 2011/0167930 A1 | 7/2011 | Feingold et al. |
| 2011/0176977 A1 | 7/2011 | Tseung et al. |
| 2011/0269238 A1 | 11/2011 | Key et al. |
| 2011/0297703 A1 | 12/2011 | Wilson et al. |
| 2012/0003679 A1 | 1/2012 | Haberkorn |
| 2012/0179293 A1 | 7/2012 | Feingold et al. |
| 2012/0309044 A1 | 12/2012 | Ljungmann et al. |
| 2013/0029409 A1 | 1/2013 | Sweet et al. |
| 2013/0084567 A1 | 4/2013 | Buchanan et al. |
| 2013/0203103 A1 | 8/2013 | Feingold et al. |
| 2013/0217108 A1 | 8/2013 | Key et al. |
| 2013/0330252 A1 | 12/2013 | Winther et al. |
| 2014/0038232 A1 | 2/2014 | Key et al. |
| 2015/0031073 A1 | 1/2015 | Lemme et al. |

FOREIGN PATENT DOCUMENTS

| | | |
|---|---|---|
| CN | 1847821 | 10/2006 |
| DE | 385159 | 11/1923 |
| DE | 3902476 | 8/1990 |
| EP | 0185330 | 6/1986 |

(56) References Cited

FOREIGN PATENT DOCUMENTS

| EP | 0557871 | 9/1993 |
|---|---|---|
| EP | 1028320 | 8/2000 |
| GB | 2037255 | 7/1980 |
| JP | 57144061 | 3/1981 |
| JP | 61200966 | 12/1986 |
| JP | 62100634 | 5/1987 |
| JP | 3148067 | 6/1991 |
| JP | 5504627 | 7/1993 |
| JP | 6510860 | 12/1994 |
| JP | 9503060 | 3/1997 |
| JP | 10501167 | 2/1998 |
| JP | 11170558 | 6/1999 |
| JP | 11258243 | 9/1999 |
| JP | 2000167318 | 6/2000 |
| JP | 2001095495 | 4/2001 |
| JP | 2001509727 | 7/2001 |
| JP | 2001512823 | 8/2001 |
| JP | 2001522033 | 11/2001 |
| JP | 2002507738 | 3/2002 |
| JP | 2002510247 | 4/2002 |
| JP | 2002522065 | 7/2002 |
| JP | 2003057246 | 2/2003 |
| JP | 2003519791 | 6/2003 |
| JP | 2004533605 | 11/2004 |
| JP | 2006220654 | 8/2006 |
| JP | 2006220659 | 8/2006 |
| JP | 2009538426 | 11/2009 |
| JP | 2010510430 | 4/2010 |
| WO | WO-9113335 | 9/1991 |
| WO | WO-9508774 | 3/1995 |
| WO | WO-9526796 | 10/1995 |
| WO | WO-9639260 | 12/1996 |
| WO | WO-9908090 | 2/1999 |
| WO | WO-9922867 | 5/1999 |
| WO | WO-0009650 | 2/2000 |
| WO | WO-0012994 | 3/2000 |
| WO | WO-0141918 | 6/2001 |
| WO | WO-02072264 | 9/2002 |
| WO | WO-03054553 | 7/2003 |
| WO | WO-03091710 | 11/2003 |
| WO | WO-03106033 | 12/2003 |
| WO | WO-2004059288 | 7/2004 |
| WO | WO-2004074847 | 9/2004 |
| WO | WO-2004092710 | 10/2004 |
| WO | WO-2005000731 | 1/2005 |
| WO | 1774636 A | 5/2006 |
| WO | WO-2015051295 | 4/2015 |

OTHER PUBLICATIONS

Sakura Finetek, Australian Examination Report dated Mar. 28, 2014, Australian Appln. No. 2012202090, 4 pages.
Sakua Finetek, Final Office Action dated May 1, 2012 for U.S. Appl. No. 11/349,663, 13 pages.
Sakura Finetek, Japanese Office Action dated Apr. 3, 2012 for Divisional Application No. 2006-34571., 3 pages.
Sakura Finetek, Extended Search Report dated Jun. 4, 2012 for European App No 12153210.5, 6 pages.
Sakura Finetek, Japanese Office Action dated Jul. 19, 2012 for Application No. 2009-512152, 2 pages.
Sakura Finetek, Japanese Office Action dated Jul. 19, 2012 for Appln. No. 2009-512152.
Sakura Finetek, CN Notification of Reexamination dated Sep. 18, 2012 for Chinese Appln. No. 200610007366.7.
Sakura Finetek, Australian Office Action dated Sep. 21, 2012 for Application No. 2007267881.
Sakura Finetek, Final Office Action dated Jan. 19, 2011 for U.S. Appl. No. 11/349,663., 24 pages.
Sakura Finetek, Non-final Office Action dated Feb. 18, 2011 for U.S. Appl. No. 11/441,668., 13 pages.
Sakura Finetek, Chinese Office Action dated Mar. 31, 2011 for Appln. No. 200610007366.7, 6 pages.
Sakura Finetek, Non-final Office Action dated Aug. 2, 2011 for U.S. Appl. No. 11/441,668., 17 pages.
Sakura Finetek, Final Office Action dated Aug. 31, 2011 for U.S. Appl. No. 11/349,663, 20 Pages.
Sakura Finetek, Non-Final Office Action dated Jan. 31, 2012 for U.S. Appl. No. 11/349,663, 12 pages.
Sakura Finetek, Australian Office Action dated Jan. 3, 2012 for 2007267881, 5 pages.
Sakura Finetek, Chinese office action dated Jan. 18, 2012 for CN 200780019204.8.
Sakura Finetek, Japanese Office Action dated Mar. 1, 2012 for App No. 2008-141687., 8 pages.
Sakura Finetek, Final Office Action dated Mar. 5, 2012 for U.S. Appl. No. 11/349,663., 11 pages.
Sakura Finetek, Chinese Office Action dated Feb. 16, 2012 for Chinese App 200610004479.1, 23 pages.
Sakura Finetek, Japanese Office Action dated Mar. 12, 2012 for Application No. 2008-141687, 7 pages.
Sakura Finetek, Non-Final Office Action dated Mar. 27, 2012 for U.S. Appl. No. 11/441,668., 15 pages.
Sakura Finetek, Japanese Office Action dated Jan. 30, 2012 for Application No. 2009-512152, 6 pages.
Sakura Finetek U.S.A., First office action dated Mar. 31, 2011 for EP Appln. No. 04780745.8, 3 pgs.
Sakura Finetek U.S.A., Third Office Action dated Jun. 9, 2011 for CN Appln. No. 200610007365.2, 6 pgs.
Sakura Finetek U.S.A., Sixth Office Action dated Mar. 31, 2011 for Chinese Appln. No. 200610007366.7, 6 pgs.
Sakura Finetek U.S.A., Chinese Office Action dated Jun. 9, 2011 for Appln. No. 2006100073652, 6.
Sakura Finetek U.S.A., Japanese office action dated Jul. 6, 2011 for JP Appln. No. 2008-141687.
Sakura Finetek U.S.A., Inc., Office Action dated Feb. 26, 2009 for U.S. Appl. No. 11/441,668.
Sakura Finetek U.S.A. Inc., CN Office Action dated May 10, 2010 for Chinese Appln. No. 200610007366.7.
Sakura Finetek U.S.A. Inc., Final office action dated May 25, 2010 for U.S. Appl. No. 11/441,668.
Sakura Finetek U.S.A., Inc., Office Action dated Jul. 21, 2010; Australian Application No. 2008229802.
Sakura Finetek U.S.A., Inc., Office Action dated Aug. 13, 2010; Australian Appln No. 2006200549.
Sakura Finetek U.S.A., Inc., Office Action dated Oct. 11, 2010; European Appln No. 07795292.7.
Sakura Finetek U.S.A., Inc., CN Office Action dated May 8, 2009 for Chinese Appln. No. 200610007366.7.
Sakura Finetek U.S.A., Inc., European Office Action dated Mar. 18, 2008 for EP Appln No. 06101497.3.
Sakura Finetek U.S.A., Inc., Non-Final Office Action dated Nov. 29, 2012 for U.S. Appl. No. 13/238,511.
Sakura Finetek U.S.A., Inc., Non-Final Office Action dated Oct. 23, 2012 for U.S. Appl. No. 13/018,609.
Sakura Finetek U.S.A., Inc., EP Office Action dated Jun. 27, 2008, EP Appln No. 06101498.1, 9 pages.
Sakura Finetek U.S.A., Inc., EP Search Report dated Jun. 20, 2006, EP Appln No. 06101498.1, 6 pages.
Sakura Finetek U.S.A., Inc., EP Search Report dated Jun. 20, 2006, EP Appln No. 06101497.3, 6 pages.
Sakura Finetek U.S.A., Inc., EP Search Report dated Dec. 18, 2006, EP Appln No. 06101495.7, 10 pages.
Sakura Finetek U.S.A., Inc., JP Office Action dated Dec. 26, 2008, Japanese Appln No. 2006-34547.
Sakura Finetek U.S.A., Inc., JP Office Action dated Feb. 27, 2008, Japanese Appln No. 2006-34571.
Sakura Finetek U.S.A., Inc., JP Office Action dated Feb. 27, 2008, Japanese Appln No. 2006-030350.
Sakura Finetek U.S.A., Inc., JP Office Action dated Nov. 30, 2007, Japanese Appln No. 2006523317 9 pages.
Sakura Finetek U.S.A., Inc., Office Action dated Jul. 23, 2007, EPO Application No. 06101495.7.
Sakura Finetek U.S.A., Inc., PCT Search Report dated Aug. 8, 2006, PCT Appln No. PCT/US04/25960, 10 pages.

(56) References Cited

OTHER PUBLICATIONS

Sakura Finetek U.S.A., Inc., PCT Search Report dated Nov. 16, 2007, PCT Appln No. PCT/US2007/012400, 13 pages.
Sakura Finetek USA Inc., Office Action dated Jun. 25, 2012; European Appln No. 07795292.7, 6 pages.
Sakura Finetek USA Inc., Non-Final Office Action dated Jun. 13, 2014 for U.S. Appl. No. 13/238,511.
Sakura Finetek USA Inc., Non-Final Office Action dated Aug. 21, 2014 for U.S. Appl. No. 14/297,537.
Sakura Finetek USA Inc., Final Office Action dated Oct. 9, 2013 for U.S. Appl. No. 13/018,609.
Sakura Finetek USA Inc., Notice of Allowance dated Feb. 14, 2014, U.S. Appl. No. 13/018,609.
Sakura Finetek USA, Inc., Notice of Allowance dated Nov. 14, 2014, U.S. Appl. No. 13/238,511.
Sakura Finetek USA, Inc., Canadian Office Action dated Feb. 25, 2013 for Appln. No. 2652898.
Sakura Finetek USA, Inc., Final Office Action dated Mar. 14, 2013 for U.S. Appl. No. 13/018,609.
Sakura Finetek USA, Inc., Final Office Action dated Apr. 5, 2013 for U.S. Appl. No. 13/238,511.
Sakura Finetek USA, Inc., Non-Final Office Action dated Jul. 1, 2013 for U.S. Appl. No. 13/018,609.
Shi, Shan-Rong, et al., "Enhancement of immunochemical staining in aldehyde-fixed tissue", U.S. Appl. No. 11/249,180, filed Oct. 11, 2005.
Zhang, Guangrong, et al., "Deparaffinization compositions and methods for their use", U.S. Appl. No. 11/250,142, filed Oct. 13, 2005.
Sakura Finetek U.S.A., Inc., Non final office action dated Jan. 21, 2014 for U.S. Appl. No. 14/057,888.
Sakura Finetek U.S.A., Inc., Japanese Office Action, JP Appln. No. 2012-200405, (dated Aug. 2, 2016).
Sakura Finetek U.S.A., Inc., Japanese Office Action with English-language translation, JP Appln. No. 2012-200390, (dated Aug. 23, 2016).
Sakura Finetek U.S.A., Inc., Chinese Office Action, CN Application No. 2012103596084, with English translation, (dated Aug. 22, 2016), 14 pages.
Sakura Finetek U.S.A., Inc., Chinese Office Action, CN Application No. 2012103596084, with English translation, (dated Jan. 12, 2016), 12 pages.
Sakura Finetek U.S.A., Inc., Notice of Allowance for U.S. Appl. No. 11/349,663, (dated Aug. 8, 2016).
Sakura Finetek U.S.A., Inc., Office Action, BR Application No. PI0602274-0, (dated Aug. 18, 2015).
Sakura Finetek USA Inc., Second Office Action, CN Appln. No. 201210359632.8, with English-language translation, (dated Jul. 6, 2016), 19 pages.
Notice of Allowance dated Dec. 24, 2014, U.S. Appl. No. 14/297,537.
European Office Action dated Jan. 7, 2015 for European App No. 12153210.5, 4 pages.
Sakura Finetek U.S.A., Inc., Japanese Office Action dated Jul. 7, 2015, JP Appln. No. 2012-012269, with English translation, 31 pages.
Sakura Finetek U.S.A., Inc., Chinese Office Action dated Dec. 21, 2016, Appln No. 201210359632.8.

\* cited by examiner

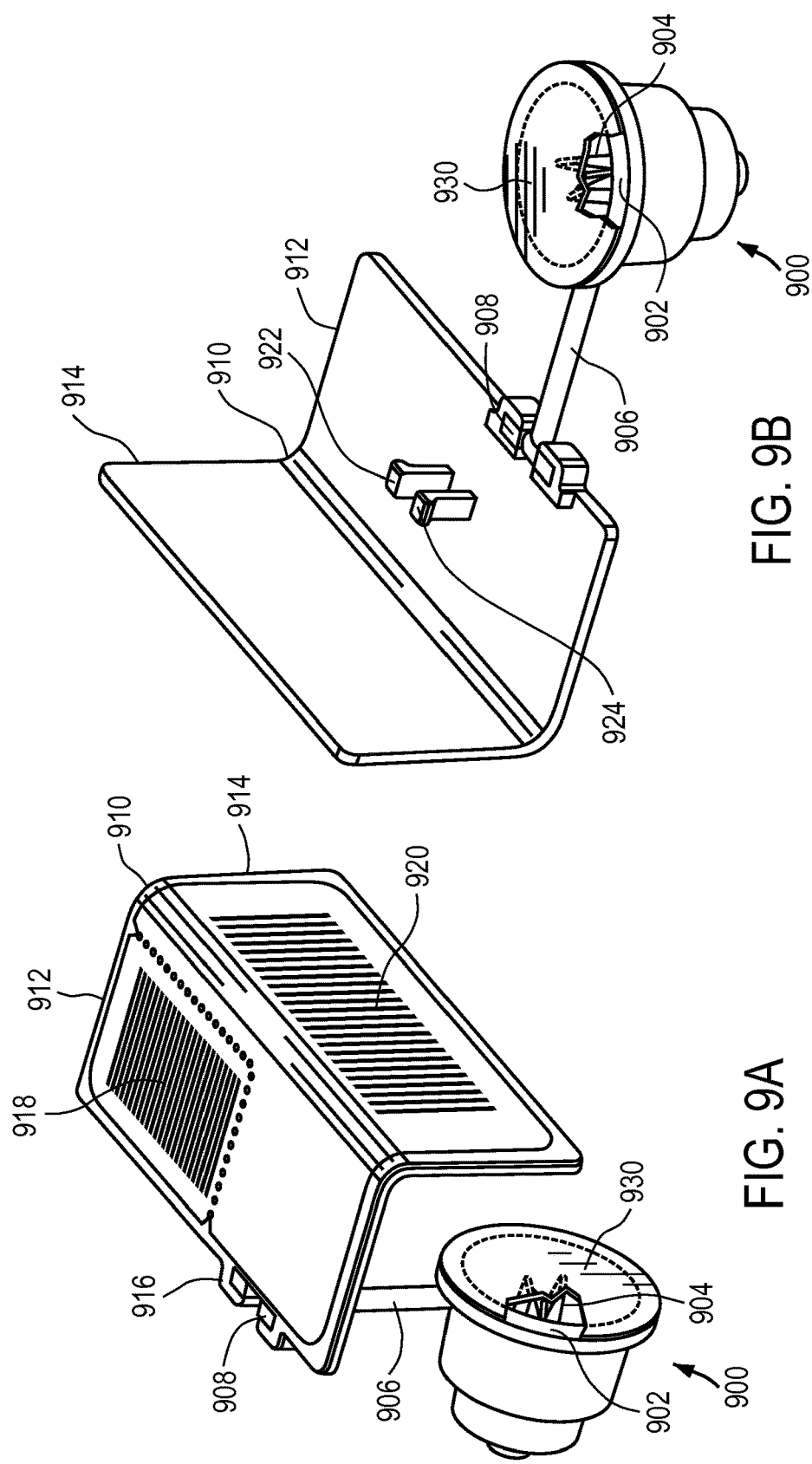

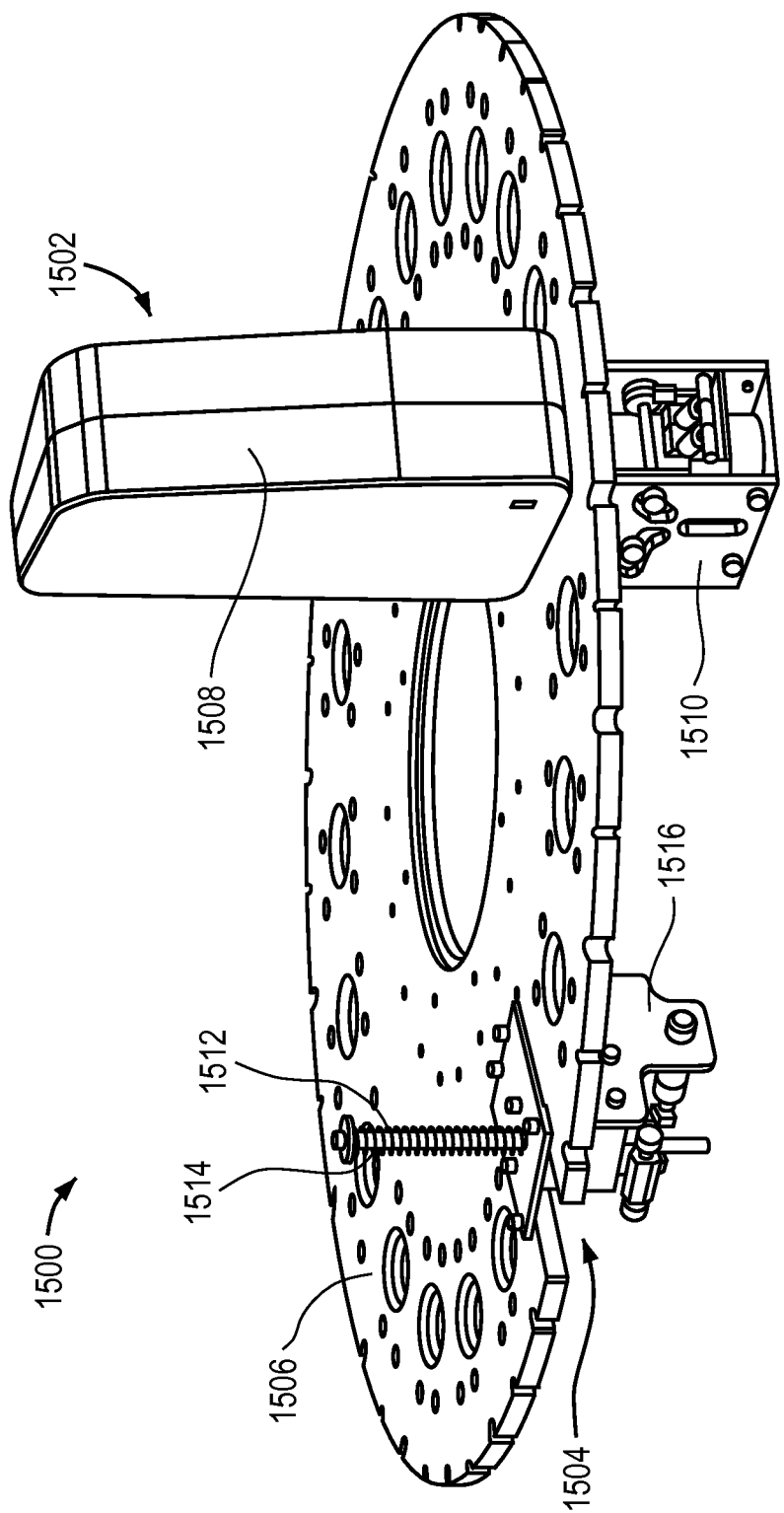

Run Scan Details

| Station No. | SPAD Antibody | Slide Antibody | Station No. |
|---|---|---|---|
| 1 | | | 1 |
| 2 | LCA | LCA | 2 |
| 3 | CD30 | CD30 | 3 |
| 4 | | | 4 |
| 5 | CD30 | CD30 | 5 |
| 6 | | | 6 |
| 7 | | | 7 |
| 8 | | | 8 |
| 9 | Desmin | Desmin | 9 |
| 10 | Cytokeration 7 | Cytokeration 7 | 10 |
| 11 | | | 11 |
| 12 | Vimenitin | Vimenitin | 12 |
| 13 | | | 13 |
| 14 | | | 14 |
| 15 | | | 15 |
| 16 | LCA | LCA | 16 |
| 17 | LCA | LCA | 17 |
| 18 | | | 18 |
| 19 | | | 19 |
| 20 | | | 20 |
| 21 | | | 21 |
| 22 | | | 22 |
| 23 | | | 23 |
| 24 | | | 24 |
| 25 | | | 25 |
| 26 | | | 26 |
| 27 | | | 27 |
| 28 | | | 28 |
| 29 | | | 29 |
| 30 | | | 30 |

[Start Run]  [Re-Scan]  [Cancel]

FIG. 23

Run Scan Details

| Station No. | SPAD Antibody | Slide Antibody | Station No. |
|---|---|---|---|
| 1 | | | 1 |
| 2 | LCA | CD30 | 2 |
| 3 | CD30 | LCA | 3 |
| 4 | | | 4 |
| 5 | CD30 | CD30 | 5 |
| 6 | | | 6 |
| 7 | | | 7 |
| 8 | | | 8 |
| 9 | Desmin | Desmin | 9 |
| 10 | Cytokeration 7 | Cytokeration 7 | 10 |
| 11 | | | 11 |
| 12 | Vimenitin | Vimenitin | 12 |
| 13 | | | 13 |
| 14 | | | 14 |
| 15 | | | 15 |
| 16 | LCA | LCA | 16 |
| 17 | LCA | LCA | 17 |
| 18 | | | 18 |
| 19 | | | 19 |
| 20 | | | 20 |
| 21 | | | 21 |
| 22 | | | 22 |
| 23 | | | 23 |
| 24 | | | 24 |
| 25 | | | 25 |
| 26 | | | 26 |
| 27 | | | 27 |
| 28 | | | 28 |
| 29 | | | 29 |
| 30 | | | 30 |

[Start Run]  [Re-Scan]  [Cancel]

FIG. 24

AUTOMATED STAINING SYSTEM AND REACTION CHAMBER

CROSS-REFERENCE TO RELATED APPLICATION

This application is a divisional of co-pending U.S. patent application Ser. No. 13/238,511, filed Sep. 21, 2011 and incorporated herein by reference.

BACKGROUND

Field

An automated staining system, in particular an automated staining system for processing biological specimens.

Background

In various settings, processing and testing of biological specimens is required for diagnostic purposes. Generally speaking, pathologists and other diagnosticians collect and study samples from patients, and utilize microscopic examination, and other devices to assess the samples at cellular levels. Numerous steps typically are involved in pathology and other diagnostic processes, including the collection of biological samples such as blood and tissue, processing the samples, preparation of microscope slides, staining, examination, re-testing or re-staining, collecting additional samples, re-examination of the samples, and ultimately the offering of diagnostic findings.

Tissue processors can be operated with varying levels of automation to process human or animal tissue specimens for histology or pathology uses. Various types of chemical reagents can be used at various stages of tissue processing and various systems have been developed for delivering reagents to specimen containing slides. Examples of known reagent delivery systems include small quantity release dispensers, manual pouring into reagent vats, or via bulk containers connected with a processor via tubing.

There are various disadvantages of known systems. For example, manually pouring into, or draining, reagent vats is time consuming and requires pouring accuracy, thereby decreasing the overall efficiency of the tissue processing system. Another disadvantage is that manually pouring and draining reagents can be sloppy, requiring clean-up of spills and consequential instrument down-time. A further disadvantage is that manually selecting the correct reagent requires operator attention and accuracy and there is an increased possibility of reagent application errors, resulting in a decrease in test accuracy and operational efficiency.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

FIG. 9A illustrates a perspective view of an embodiment of a reagent dispensing capsule and bracket.

FIG. 9B illustrates a perspective view of the reagent dispensing capsule and bracket of FIG. 9A.

FIG. 15 illustrates a perspective view of an embodiment of an overhead fluid dispensing system and capsule pressing mechanism.

FIG. 23 illustrates an embodiment of a display associated with a sample processing procedure.

FIG. 24 illustrates an embodiment of a display associated with a sample processing procedure.

DETAILED DESCRIPTION

In the following paragraphs, the present invention will be described in detail by way of example with reference to the accompanying drawings. Throughout this description, the preferred embodiments and examples shown should be considered as exemplars, rather than as limitations on the present invention. Furthermore, reference to various aspects of the embodiments disclosed herein does not mean that all claimed embodiments or methods must include the referenced aspects.

Figure 1:
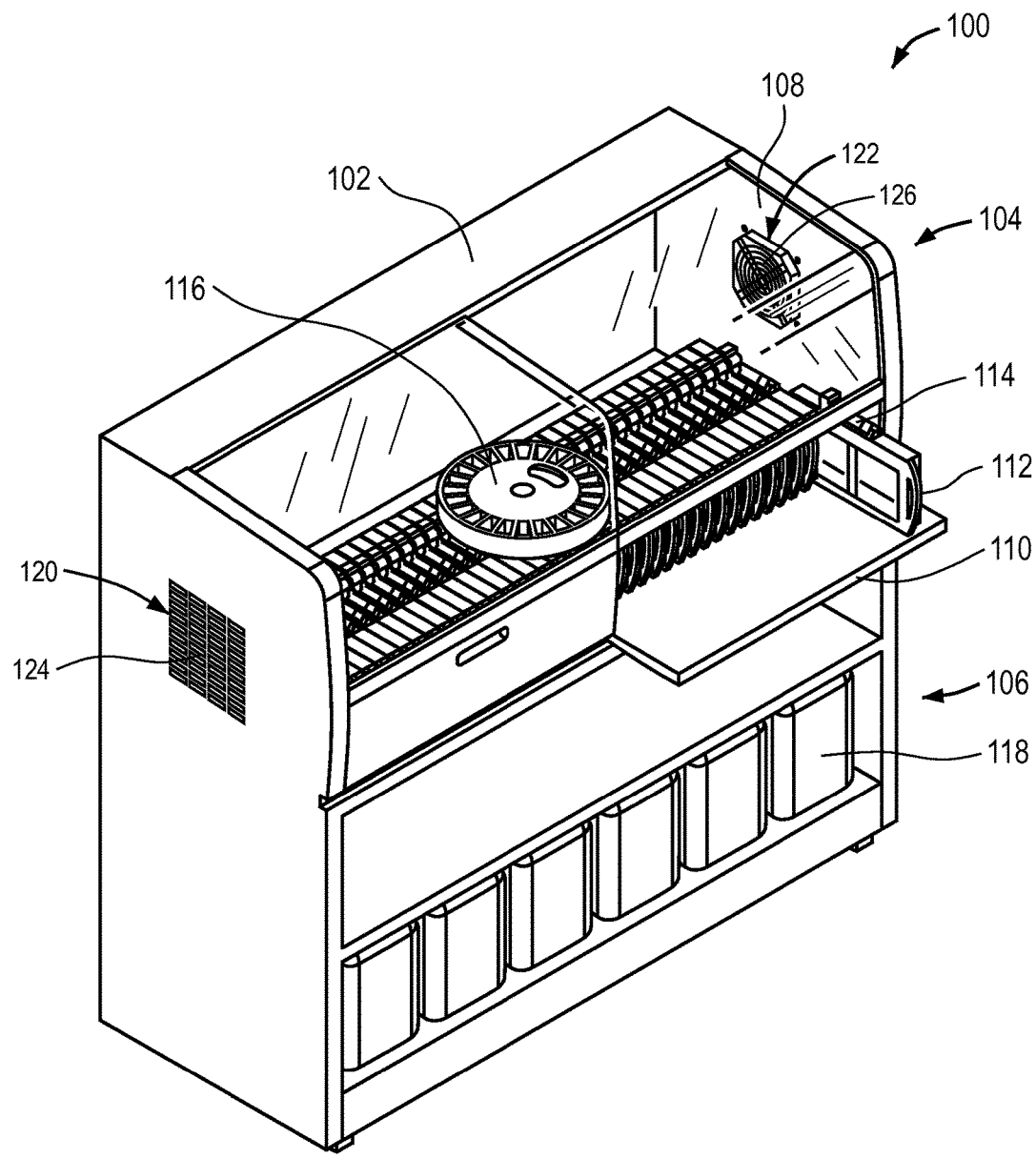
FIG. 1 illustrates a perspective view of an embodiment of a sample processing system.

FIG. 1 illustrates a perspective view of an embodiment of a sample processing system. Sample processing system 100 includes housing 102 for enclosing and storing various components of processing system 100. Housing 102 includes reaction compartment 104 and storage compartment 106. Reaction compartment 104 defines a compartment within which sample processing occurs. Cover member 108 and door member 110 may be used to gain access to components within reaction compartment 104.

Reaction compartment 104 is dimensioned to accommodate a plurality of reaction stations 112. Reaction stations 112 may slide in and out of reaction compartment 104 to facilitate access to reaction chambers 114 mounted thereon. In some embodiments, 30 reaction stations 112 are linearly positioned within reaction compartment 104. In other embodiments, reaction stations 112 are arranged in rows within reaction compartment 104. For example, where 30 reaction stations 112 are provided, each row may include 15 reaction stations 112. Although 30 reaction stations 112 are described, it is contemplated that any number of reaction stations 112 may be positioned within reaction compartment 104 as deemed desirable.

Each of reaction stations 112 includes one of reaction chambers 114 mounted thereon. Reaction chambers 114 are dimensioned to support a slide for further processing. A biological sample may be mounted to the slide for processing. During processing, a stain or other processing fluid is applied to the sample. In some embodiments, the processing fluid may be applied to the sample by a reagent cartridge attached directly to each of reaction stations 112. In other embodiments, sample processing system 100 may include a movable mounting assembly 116 for mounting of fluid dispensing cartridges (not shown) above reaction stations 112. The fluid dispensing cartridges may include a fluid such as a reagent that is to be applied to the sample. In addition, bulk containers 118 may be mounted below reaction stations 112. Bulk containers 118 may be reagent containers, waste containers or any other bulk container found desirable. A reagent from bulk containers 118 may further be dispensed onto the sample during processing.

System 100 may further include air inlet assembly 120 and air outlet assembly 122 to help control a temperature within reaction compartment 104. Processing of the samples within reaction compartment 104 generates heat. As the temperature within reaction compartment 104 increases, so too does the rate of evaporation of any processing fluids used at the reaction stations. In addition, the increased temperature may have a negative impact on reagent stability. To help maintain a desired temperature within reaction compartment 104 (i.e. a temperature that will not speed up evaporation), air inlet assembly 120 and air outlet assembly 122 may be used to circulate air through reaction compartment 104. In this aspect, air inlet assembly 120 may include vent 124 mounted along one side of a wall of housing 102 and one or more fans (not shown) mounted at an opposite side of the wall of housing 102 to help draw ambient air into reaction compartment 104. Air outlet assembly 122 may be mounted to a wall on an opposite side of housing 102 and include one or more fans 126 coupled to an air outlet vent formed through the wall to help draw air out of reaction compartment 104. It is further contemplated that filters may be incorporated into air inlet assembly 120 and/or air outlet assembly 122 to prevent contaminants from entering reaction compartment 104. Circulating ambient air through reaction compartment 104 as described helps to maintain a desired processing temperature within reaction compartment 104.

Figure 2:
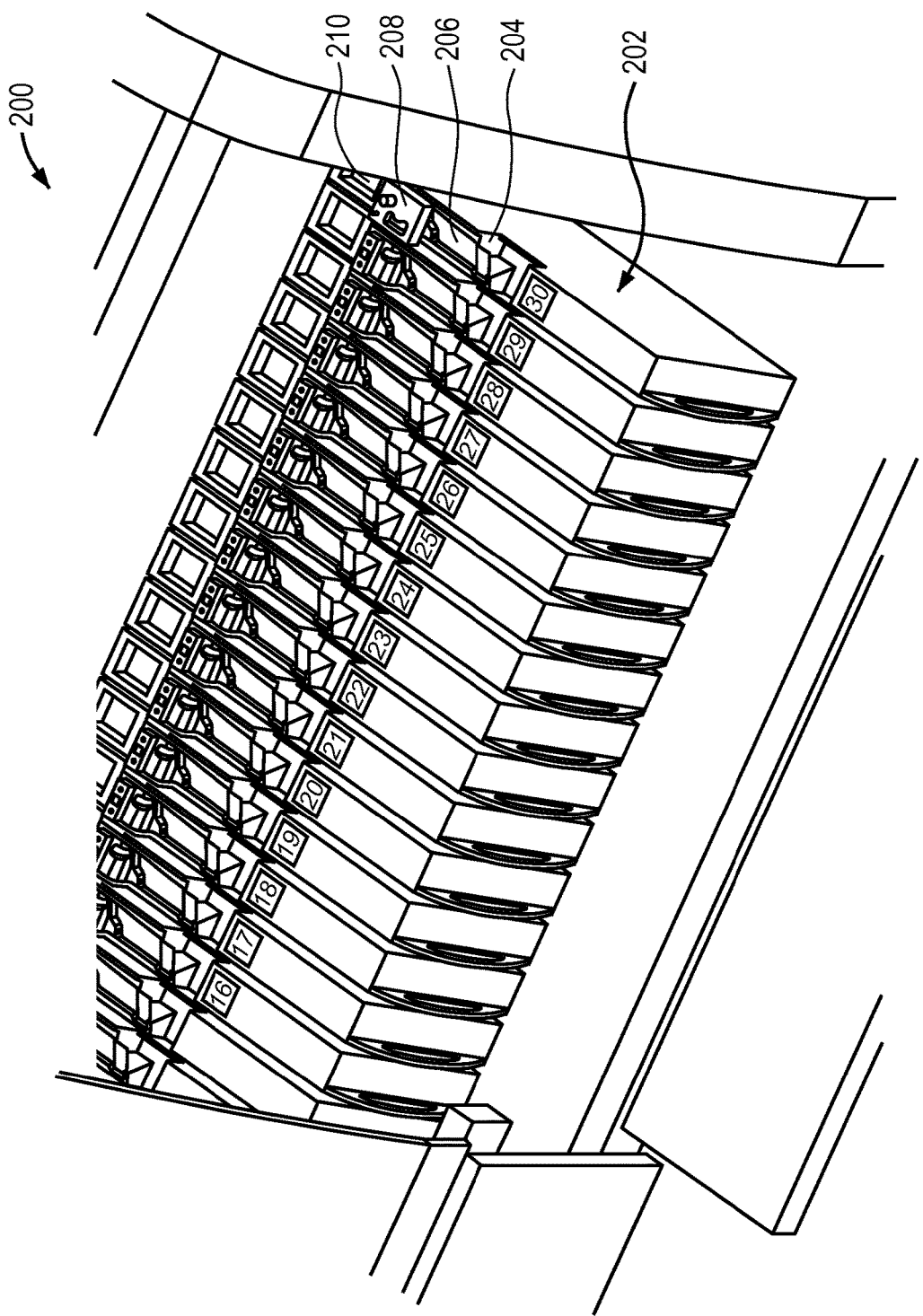
FIG. 2 illustrates a perspective view of an embodiment of a sample processing system with reaction stations.

FIG. 2 illustrates a perspective view of an embodiment of a sample processing system with reaction stations. Processing system 200 includes reaction stations 202. Any number of reaction stations 202 may be positioned within processing system 200. For example, in one embodiment, 30 reaction stations 202 may be positioned within processing system 200. Each of reaction stations 202 may be independent from another. In this aspect, each of reaction stations 202 may slide in and out of processing system 200 separately so that a user may easily access a desired one of reaction stations 202 (e.g., see FIG. 1 with one reaction station 112 slid partially out of processing system 100).

Each of reaction stations 202 of sample processing system 200 may include support member 204. Support member 204 may be mounted to an upper surface of reaction station 202. Support member 204 may be dimensioned to support reaction chamber 206 and reagent cartridge 208. As previously discussed, reaction chamber 206 is dimensioned to support a slide having a biological sample mounted thereon. A fluid may be caused to flow into reaction chamber 206 by virtue of one or a combination of capillarity (i.e., capillary action) (such as where the fluid enters a section in which the slide is positioned adjacent reaction chamber 206), pressure differential applied by an inlet or outlet port of reaction chamber 206, vacuum pulsing and a fixed quantity pump, such as applied via one of the ports, and gravity (such as where the fluid flows from reagent cartridge 208 positioned above reaction chamber 206).

Reagent cartridge 208 may contain a primary reagent that is to be applied to the slide having a sample mounted thereon. Representatively, reagent cartridge 208 may contain reagents suitable for a potentially unlimited variety of procedures, including immunohistochemistry procedures, staining procedures, in situ hybridization procedures, other histochemical procedures etc. Examples of primary reagents (also called probes, markers or controls) that can be contained within reagent cartridge 208 include, without limitation, any type of antibodies, probes, nucleic acids (RNA, DNA or oligonucleotides), ligands, ligand receptors, enzymes or enzyme substrates or any other molecules suitable for a desired use. The reagents can be in a natural form, purified, concentrated, diluted or otherwise conditioned. In an embodiment, the addition of signal molecules such as fluorescent dyes, enzymes, conjugates (e.g., biotin, avidin, streptavidin), metals (such as silver or gold particles), dyes, stains, radioactively tagged molecules, or any other substances such as signaling or reporter molecules.

Reagent cartridge 208 may further be used to facilitate application of one or more secondary reagents onto the slide.

In one embodiment, secondary reagents are dispensed from above onto a drip and flow surface of reagent cartridge 208, for example by a fluid dispensing cartridge, as discussed in greater detail below. Examples of secondary reagents that can be dispensed onto the slide, either alone or in combination with other secondary reagents, or in combination with one or more primary reagents or bulk reagents include, without limitation, any type of antibodies, probes, nucleic acids (RNA, DNA or oligonucleotides), ligands, ligand receptors, enzymes or enzyme substrates or any other molecules suitable for a desired use. The reagents can be in a natural form, purified, concentrated, diluted or otherwise conditioned. In addition, signal molecules such as fluorescent dyes, enzymes, conjugates (e.g., biotin, avidin, streptavidin), metals (such as silver or gold particles), dyes, stains radioactively tagged molecules, or any other substances such as signaling or reporter molecules may also be dispensed.

In still further embodiments, one or more of a bulk type of reagent can be applied to a slide positioned on reaction chamber 206. In some embodiments, bulk reagents are stored in containers and dispensed into reaction chamber 206 via a manifold system directing the fluids into an entry port of reaction chamber 206. In addition, bulk reagents can be dispensed from an overhead bulk reagent dispenser onto reaction chamber 206 via reagent cartridge 208 attached thereto. In still further embodiments, bulk reagents can be dispensed from reagent reservoir 210 onto reaction chamber 206 via plumbing including a pump incorporated into reaction station 202. Examples of bulk reagents that can be dispensed either alone or in combination with other bulk reagents, or in combination with one or more primary reagents or secondary reagents include, without limitation, the following: Tris Buffered Saline (TBS), distilled water or dewaxing solution.

Figure 3A:
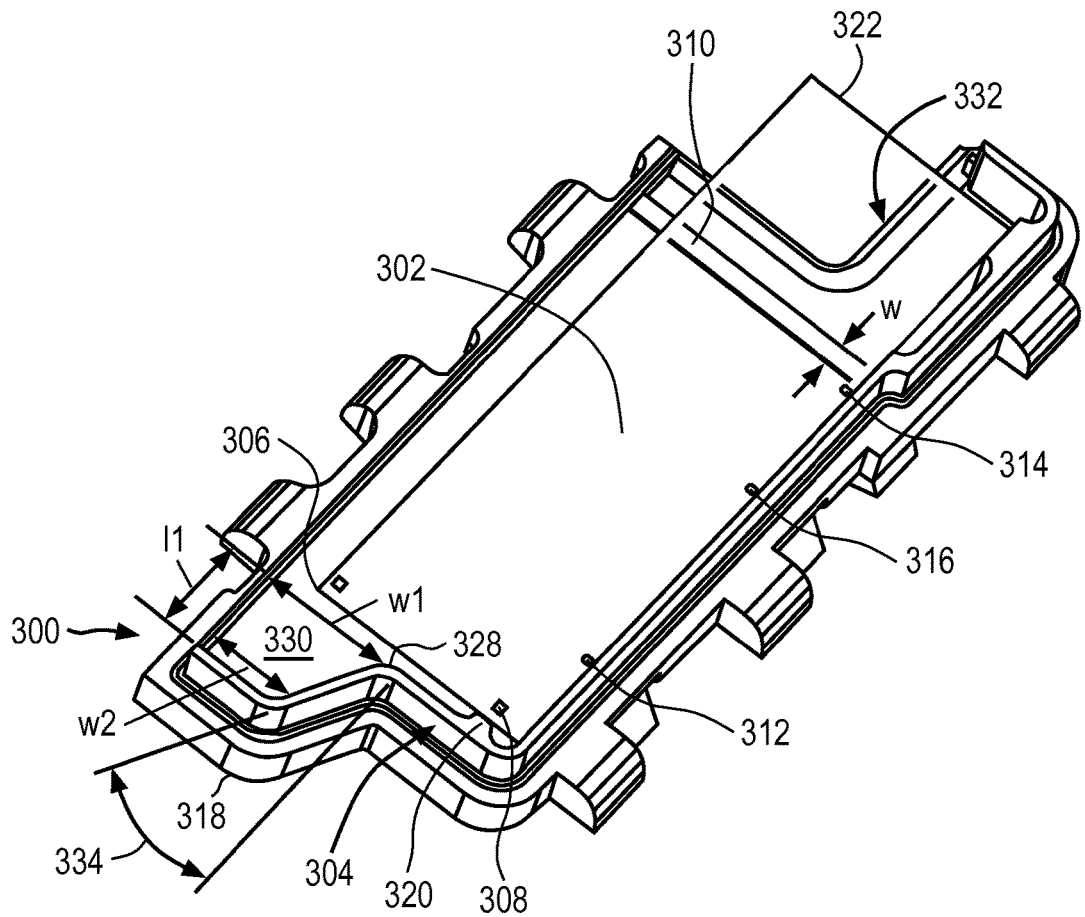
FIG. 3A illustrates a perspective view of an embodiment of a reaction chamber.

FIG. 3A illustrates a perspective view of one embodiment of a reaction chamber. Reaction chamber 300 may be a tray dimensioned to retain a sample and/or slide. As used herein the terms reaction chamber, sample retaining tray and slide retaining tray are used interchangeably for reaction chamber 300. In the illustrated embodiment, reaction chamber 300 is configured to be a microscope slide retaining tray but it shall be appreciated that reaction chamber 300 is not so limited and may be configured to retain any sample or sample container. In accordance with an aspect of the embodiment, reaction chamber 300 functions as a slide positioning and retention system that may be used in processing a substrate such as a tissue sample.

In one embodiment, reaction chamber 300 can be used multiple times. In other embodiments, reaction chamber 300 may be disposable. Reaction chamber 300 can be formed of a material having sufficient structural strength and process neutral properties to support a slide, retain and be compatible with reagents and the temperatures employed during use. Representatively, in one embodiment, reaction chamber 300 may be made of a hydrophilic material to facilitate capillary action as will be discussed in more detail below and have a hardness sufficient to withstand scratching by glass slides placed thereon. In one embodiment, reaction chamber 300 may be made of a metal material. For example, reaction chamber 300 may be made of silver, steel or aluminum. A silver material may be used to impart antimicrobial properties to reaction chamber 300. In the case of an aluminum reaction chamber 300, the surface of the aluminum may be anodized to create a hydrophilic surface. A hydrophilic surface facilitates capillary action of a fluid between the slide and reaction chamber 300. In some embodiments, the anodized surface may be thick, for example greater than 10 µm, still further, between about 10 µm and about 35 µm, for example, about 30 µm. In addition to rendering the surface hydrophilic, it is recognized that the anodized surface may increase corrosion resistance and wear resistance of reaction chamber 300.

Other exemplary materials of reaction chamber 300 may include heat-transferable polymeric materials such as plastics or cellulosic (i.e., cellulose based or comprising) materials, ceramic, TEFLON®, glass etc. Representatively, reaction chamber 300 may be made of a polyoxymethylene thermoplastic such as DELRIN® (a registered trademark of E.I. DuPont de Nemours and Co. of Wilmington, Del.). Reaction chamber 300 can be formed by any process known in the art such as injection molding, machining or any other manufacturing process suitable for generating the desired features of reaction chamber 300. In addition, it should be appreciated that reaction chamber 300 can be composed of more than one of the above discussed materials.

Reaction chamber 300 can optionally include an identifier that is human or machine readable. Representative identifiers may include, but are not limited to, visually readable, magnetically readable, tactilely readable, etc. identifiers. In some embodiments, the identifier identifies a reagent to be used in connection with a slide positioned on reaction chamber 300, for example a primary reagent. In still further embodiments, the identifier identifies the sample within reaction chamber 300 or a processing protocol to be performed on the sample.

Specific features of reaction chamber 300 may include platen 302. Platen 302 may be a substantially planar surface dimensioned to support slide 322 thereon. Slide 322 may have a length dimension of 75 millimeters (mm) and a width dimension of 25 mm and a thickness of 1 mm. Processing of the sample (e.g. biological specimen) on slide 322 may take place between slide 322 and platen 302. In this aspect, slide 322 may be positioned on platen 302 so that a surface of slide 322 containing the specimen faces platen 302. Platen 302 may be dimensioned so that an entire processing area of the slide (i.e. unfrosted slide area) is positioned on platen 302. In this aspect, where a sample occupies the entire slide processing area, the entire sample may be processed. Platen 302 may include drip surface 330 at one end for receiving a reagent applied to platen 302 from above. An opposite end of platen 302 may include cut out portion 332 to facilitate grasping of slide 322 positioned on platen 302.

Fluid inlet port 316 may be formed through platen 302 along a length dimension for applying a fluid to platen 302 from below (e.g. from a bulk reagent reservoir). Fluid outlet ports 312, 314 may further be formed through platen 302 to facilitate removal of fluids from platen 302. Fluid may be supplied or removed from platen 302 using fluid inlet port 316 or fluid outlet ports 312, 314 via a fluid delivery system such as a manifold and plumbing including passageways, a pump and valves positioned below reaction chamber 300.

Wall 304 may be formed around a portion of platen 302 to help retain a processing fluid applied to platen 302. As illustrated in FIG. 3A, wall 304 is formed around the ends and one side forming a length dimension of platen 302. It is contemplated, however, that wall 304 may be formed around any portions of platen 302 necessary to facilitate retention of a processing fluid. Wall 304 may have a height sufficient to retain fluids that may pool within a corner of platen 302 and adjacent wall 304. Representatively, wall 304 should have a height sufficient to retain from about 25 microliters (µl) to about 200 µl in reaction chamber 300, representatively from about 25 µl to about 35 µl. In this aspect, wall 304 may have a height of from about 4 mm to about 7 mm, for example, from 4.8 mm to 6.5 mm.

Wall 304 may form bend 328 along an end of platen 302 having reagent drip surface 330. Bend 328 defines angle 334 along the end of platen 302 to help direct a fluid dispensed onto reagent drip surface 330 along the end of platen 302 and between slide 322 and platen 302. Angle 334 of bend 328 not only helps to direct the fluid toward slide 322 but further helps to slow the flow of a fluid dispensed onto reagent drip surface 330 of platen 302 so that the fluid does not flow over the top of slide 322. Representatively, angle 334 may be from about 15 degrees to about 35 degrees, preferably from about 20 degrees to about 30 degrees. In one embodiment where reaction chamber 300 is configured to contain a slide (e.g., a microscope slide), drip surface 330 has a length dimension (l1) on the order of 10.5 mm and a width dimension (w1) of 13 mm, and a width dimension (w2) of 7.8 mm.

Wall 304 may also include protrusion 320 to help distance slide 322 from wall 304. Spacing slide 322 a distance from wall 304 helps with introducing and draining of fluids between slide 322 and platen 302. In particular, if the edge of slide 322 is flush with the portion of wall 304 near the point of fluid introduction (e.g. reagent drip surface 330), the fluid cannot flow freely along the edge of slide 322 and capillary action cannot draw the fluid under the edge of slide 322. In this aspect, protrusion 320 may be dimensioned to space slide 322 a distance of from about 1 mm to about 2 mm, for example 1.5 mm, from wall 304.

Reaction chamber 300 may further include spacer nodules 306, 308 and spacer bar 310 to facilitate fluid movement between slide 322 and platen 302. Spacer nodules 306, 308 and spacer bar 310 may extend from a surface of platen 302 and create a gap between platen 302 and slide 322. The gap allows fluids (e.g. a reagent dispensed onto platen 302) to be drawn between slide 322 and platen 302 by capillary action. It is to be understood that the smaller the gap, the greater the capillary action. In this aspect, in some embodiments, spacer nodules 306, 308 have a height different from a height of spacer bar 310. This height difference causes slide 322 to be supported at an angle with respect to platen 302. Capillary action is therefore stronger near the end of slide 322 closest to platen 302 then the other.

Representatively, a height of spacer nodules 306, 308 may be greater than a height of spacer bar 310 so that a gap near an end of slide 322 where a fluid is applied from above reaction chamber 300 will be larger. In this aspect, a large volume of fluid may be applied to platen 302 at drip surface 330 and initially drawn between the slide and platen 302 by capillary action. The decrease in gap height towards the opposite end of slide 322 (opposite from drip surface 330) will help draw the fluid across the entire surface of slide 322. This gap further helps to draw a fluid introduced through fluid inlet port 316 of platen 302 across an entire surface of slide 322. In other embodiments, spacer nodules 306, 308 and spacer bar 310 may have the same height. It is noted that the height may be adjusted depending upon the desired capillary action. For example, where a greater capillary force is desired, the height of spacer nodules 306, 308 and/or spacer bar 310, may be decreased in order to increase the capillary force.

Fluid inlet port 316 may be used to introduce a fluid directly between slide 322 and platen 302. Fluid outlet ports 312, 314 may be used to drain a fluid between slide 322 and platen 302. In some embodiments, fluid outlet ports 312, 314 and fluid inlet port 316 are positioned along one side of the length dimension of platen 302. Fluid inlet port 316 may be between fluid outlet ports 312, 314. The positioning of fluid outlet ports 312, 314 and fluid inlet port 316 is important for controlling the dispersion of fluids between slide 322 and platen 302. Representatively, it is preferred that outlet ports 312, 314 be a sufficient distance from their respective edges of platen 302 so as not to suck air from along the edge of slide 322. In addition, it is preferred that at least one of outlet ports 312, 314 is within an area of high surface tension (e.g. near spacer bar 310) so that an optimal amount of fluid may be withdrawn. In addition, it is preferred that outlet ports 312, 314 are positioned at opposite ends of platen 302 so that fluids can be withdrawn across a length of platen 302 at substantially the same rate. This is in comparison to the funneling effect that would occur if fluid was removed through a single outlet port positioned at, for example, the middle of platen 302. Funneling of the fluid into a single outlet port is not desirable because it results in large areas of the slide and platen 302 drying out. Although one fluid inlet port 316 and two fluid outlet ports 312, 314 are illustrated in FIG. 3A, it is contemplated that any number of outlet and inlet ports may be formed through platen 302 depending upon, for example, the desired fluid dispersion and/or platen 302 size. Further details regarding the dispersion of fluid between slide 322 and platen 302 will be discussed in reference to FIG. 6A and FIG. 6B.

In some embodiments, reaction chamber 300 may be positioned within casing 318. Casing 318 may be dimensioned to attach to the bottom portion of platen 302 and/or wall 304. Casing 318 may be used to help seal reaction chamber 300 to an underlying support member (e.g. support member 404 illustrated in FIG. 4A) and prevent reagent leakage below reaction chamber 300. Casing 318 may be made of the same or different material than reaction chamber 300. Representatively, in some embodiments, casing 318 may be made of a silicon material, or any other similar material, suitable for creating a seal between reaction chamber 300 and the support member (e.g. support member 404 illustrated in FIG. 4A).

Figure 3B:
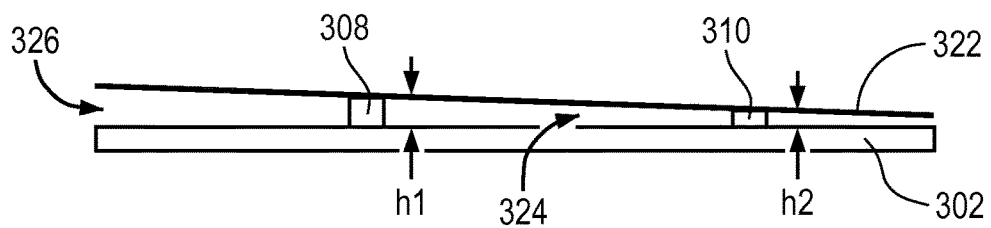
FIG. 3B illustrates a side view of the reaction chamber of FIG. 3A.

FIG. 3B illustrates a side view of the reaction chamber of FIG. 3A. As can be seen from FIG. 3B, height, h1, of spacer nodule 308 may be greater than height, h2, of spacer bar 310. In this aspect, slide 322 is positioned at an angle with respect to platen 302. Gap 324 formed between slide 322 and platen 302 is therefore greater at one end than another. In some embodiments gap 324 is greater between an end of slide 322 and platen 302 where fluid 326 is introduced (e.g. near reagent drip surface 330). Representatively, in one embodiment, height, h1, of spacer nodule 308 may be approximately 0.23 millimeters (mm) and height, h2, of spacer bar 310 may be approximately 0.18 mm. In still further embodiments, height, h1, may be from about 0.15 mm to about 0.3 mm and height, h2, may be from about 0.1 mm to about 0.25 mm.

Spacer nodule 308 may have any shape and dimensions sufficient to create a gap between slide 322 and platen 302. Representatively, spacer nodule 308 may have a substantially square shape. Spacer nodule 306 may have a substantially similar shape.

Spacer bar 310 may have any shape and dimensions sufficient to create a gap between slide 322 and platen 302 and further to prevent flow of a liquid past spacer bar 310. In one embodiment, spacer bar 310 may have an elongated rectangular shape with a width dimension, w. It is important that spacer bar 310 have a length and width, w, sufficient to prevent a fluid between slide 322 and platen 302 from passing beyond spacer bar 310. In this aspect, spacer bar 310 has a length dimension equal to a width of platen 302. A width, w, of spacer bar 310 may be from about 1 mm to about 3 mm, preferably about 2 mm. In addition to blocking fluid flow, spacer bar 310 helps to eliminate air bubbles between platen 302 and slide 322 by directing air bubbles toward an edge of slide 322. As will be discussed in more detail in reference to FIGS. 5A and 5B, platen 302 may be positioned at an angle such that platen 302 has a vertical and horizontal slant. In this aspect, a side of platen 302 at one end of spacer bar 310 may be higher than a side of platen 302 at the opposite end of spacer bar 310. Air bubbles trapped between platen 302 and slide 322 will want to rise toward the higher side of platen 302. Spacer bar 310 can help to guide any air bubbles toward the higher side and out from between slide 322 and platen 302.

Figure 4A:
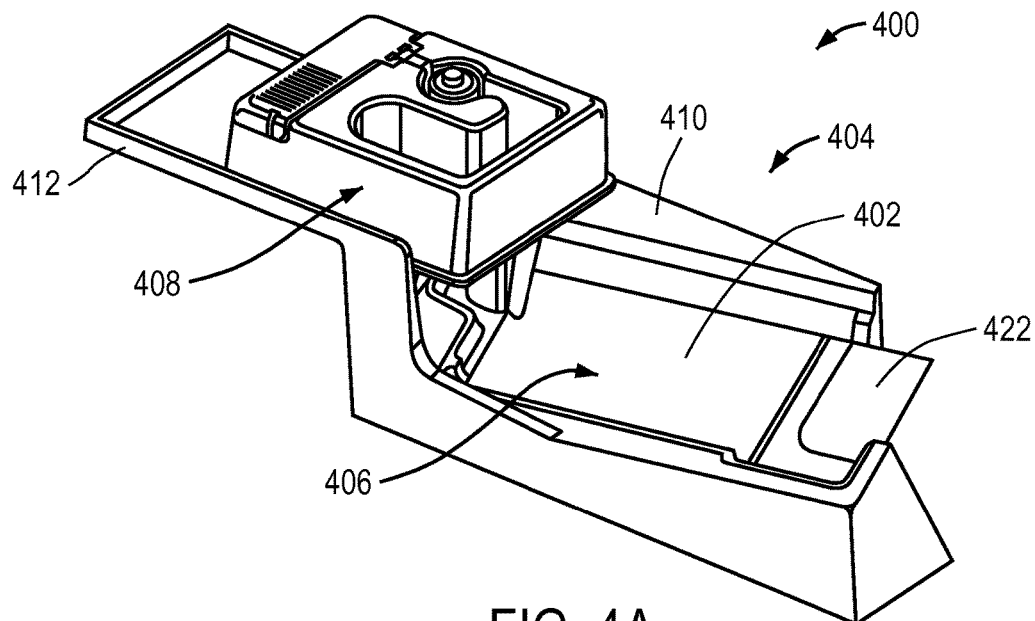
FIG. 4A illustrates a perspective view of an embodiment of a reaction chamber and reagent cartridge of a sample processing system.
Figure 4B:
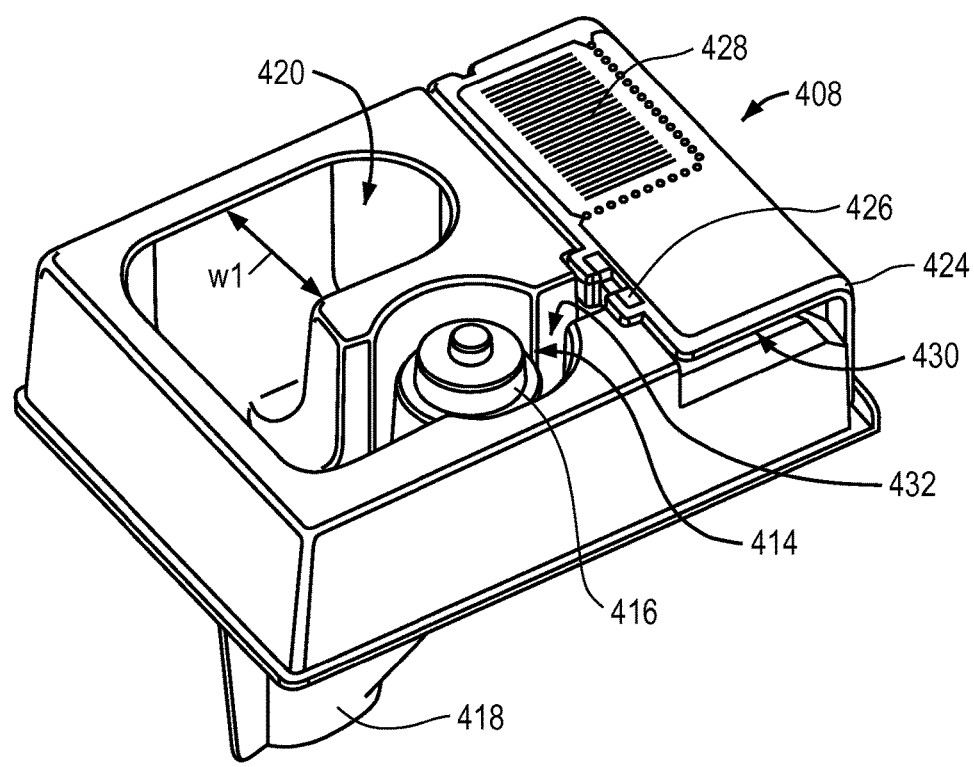
FIG. 4B illustrates a perspective view of an embodiment of a reaction chamber and reagent cartridge of a sample processing system.

FIGS. 4A and 4B illustrate a perspective view of a reaction chamber and reagent cartridge of a sample processing system. Sample processing system 400 includes support member 404 for supporting reaction chamber 406 and reagent cartridge 408. Support member 404 is fixedly attached to a reaction station of system 400 and includes lower portion 410 and upper portion 412. Lower portion 410 is dimensioned to support reaction chamber 406 at horizontal and vertical angles as will be discussed in more detail below. Reaction chamber 406 may be fixedly mounted to lower portion 410. Upper portion 412 is dimensioned to support reagent cartridge 408 above a reagent drip surface of reaction chamber 406. Reagent cartridge 408 may be removably attached to upper portion 412 so that reagent cartridge 408 may be removed and/or replaced as desired by a user. A reagent contained within reagent cartridge 408 or applied to reagent cartridge 408 may flow through reagent cartridge 408 and onto reaction chamber 406.

In some embodiments, lower portion 410 and upper portion 412 may be integrally formed pieces which form a substantially Z shaped profile. Support member 404 may be formed of any material having a sufficient strength to support reaction chamber 406 and reagent cartridge 408 and processing within reaction chamber 406. Representatively, support member 404 may be made of a metal or plastic material. Support member 404 can be formed by any process known in the art such as injection molding, machining or any other manufacturing process suitable for generating the desired features of support member 404.

Reaction chamber 406 may be substantially the same as reaction chamber 300 described in reference to FIG. 3A. Slide 422 may be positioned on reaction chamber 406 as illustrated in FIG. 4A. During operation, a reagent is dispensed from reagent cartridge 408 onto the reagent drip surface (see reagent drip surface 330 illustrated in FIG. 3A) of reaction chamber 406. Capillary action causes flow of reagent between slide 422 and platen 402.

FIG. 4B illustrates further details of reagent cartridge 408 previously discussed in reference to FIG. 4A. Reagent cartridge 408 may be a cartridge that contains a reagent or other processing fluid to be applied to slide 422. In this aspect, reagent cartridge 408 may include reagent recess 414. Reagent recess 414 may be of any shape, depth or orientation as desired such that reagent(s) contained therein are directed into reaction chamber 406. In one embodiment, the reagent is contained within capsule 416 inserted within reagent recess 414. Where capsule 416 is cylindrical in shape, reagent recess 414 may further include a cylindrical shape. Reagent recess 414 includes an open bottom such that it is in fluid communication with outlet channel 418 extending from a bottom of reagent cartridge 408. When capsule 416 within reagent recess 414 is punctured, a reagent (e.g., liquid reagent) within capsule 416 is expelled into reagent recess 414 and down through outlet channel 418 onto a drip surface of reaction chamber 406 where it flows to platen 402.

Reagent cartridge 408 may further help to direct a fluid dispensed from an overhead fluid dispensing cartridge onto a drip surface of reaction chamber 406. In this aspect, reagent cartridge 408 may include channel 420 in fluid communication with outlet channel 418. Channel 420 extends from a top surface of reagent cartridge 408 through reagent cartridge 408 to outlet channel 418. A fluid (e.g. a reagent) dispensed into channel 420 from an overhead fluid dispenser travels through reagent cartridge 408 and out outlet channel 418 onto reaction chamber 406. Since both channel 420 and reagent recess 414 are in fluid communication with outlet channel 418, fluids dispensed from each are mixed within outlet channel 418 prior to being dispensed onto reaction chamber 406. In this aspect, outlet channel 418 serves as a mixing chamber for two or more fluids dispensed from reagent cartridge 408.

In some embodiments, two or more fluids may be dispensed into channel 420 from an overhead fluid dispenser. In this aspect, channel 420 may have a width dimension (w1) sufficient to receive two or more fluids. Representatively, channel 420 may have a width of from about 10 mm to about 15 mm, preferably about 12.5 mm. In addition, it is contemplated that a shape of the bottom of channel 420 may have an unreflecting curve to minimize splashing of fluids dispensed into channel 420.

Capsule 416 may be attached to reagent cartridge 408 with bracket 424. Bracket 424 may include an elongated connector 426 such as a strap which attaches to capsule 416. In one embodiment, capsule 416 is removably attached to connector 426 of bracket 424. In other embodiments, capsule 416 is fixedly attached to connector 426. Reagent cartridge 408 may include indentation 430 dimensioned to receive bracket 424. In addition, furrow 432 may be formed within reagent cartridge 408 between indentation 430 and reagent recess 414. Connector 426 may be inserted within furrow 432 when bracket 424 is attached to reagent cartridge 408 so that capsule 416 is securely aligned within reagent recess 414 by a reaction force of connector 426.

Identifier 428 may be placed on bracket 424 as illustrated in FIG. 4B. Identifier 428 will be discussed in more detail in reference to FIG. 9A. Reagent cartridge 408 and capsule 416 will be discussed in more detail in reference to FIGS. 7-9.

Reagent cartridge 408 may be made of the same or different material as reaction chamber 406. Representatively, reagent cartridge 408 may be made of a plastic, metal or ceramic material and formed by any process known in the art such as injection molding, machining or any other manufacturing process suitable for generating the desired features.

Figure 5A:
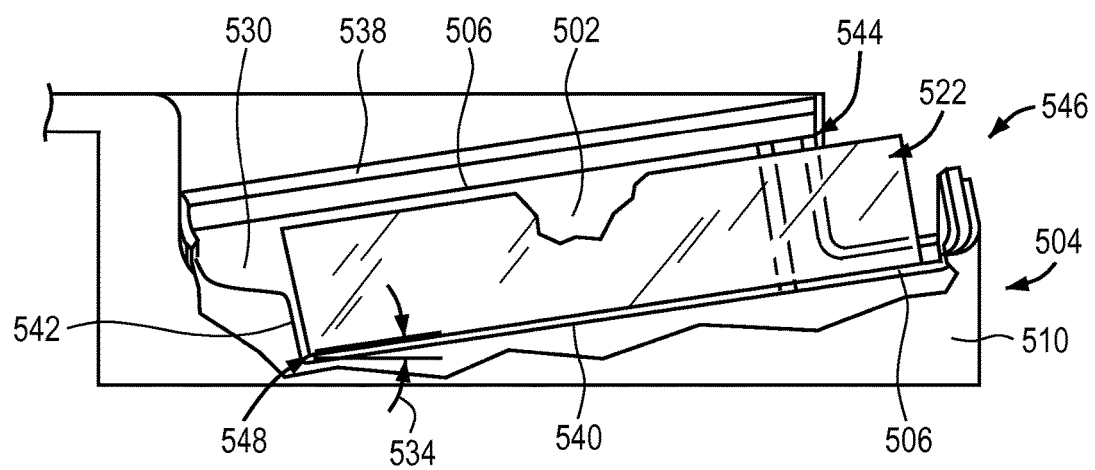
FIG. 5A illustrates a perspective view of an embodiment of a reaction chamber.
Figure 5B:
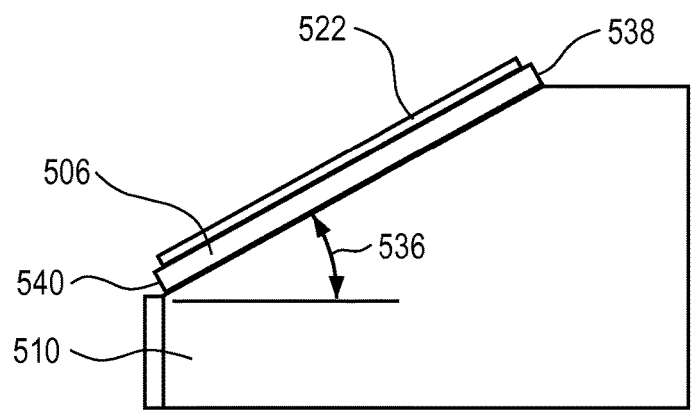
FIG. 5B illustrates a side perspective view of an embodiment of a reaction chamber.

FIGS. 5A and 5B are perspective views illustrating the horizontal and vertical angles of one embodiment of a reaction chamber. Reaction chamber 506 is positioned at horizontal angle 534 and vertical angle 536 to facilitate movement of fluid (e.g. reagent) between slide 522 and platen 502. FIGS. 5A and 5B illustrate reaction chamber 506 positioned on lower portion 510 of support member 504. Lower portion 510 is dimensioned to receive and position reaction chamber 506 at horizontal angle 534 and vertical angle 536. Horizontal angle 534 refers to the angle of an edge of reaction chamber 506 defining a length dimension of reaction chamber 506 with respect to the level ground. Vertical angle 536 refers to the angle of a surface of reaction chamber 506 defining platen 502 to the level ground. Horizontal angle 534 is illustrated in FIG. 5A and vertical angle 536 is illustrated in FIG. 5B. Horizontal angle 534 may be from about 5 degrees to about 15 degrees, for example from 6 degrees to 8 degrees, and in another example, about 7 degrees. Vertical angle 536 may be from about 15 degrees to about 45 degrees, for example from 20 degrees to 30 degrees, and in another example, about 29 degrees.

As previously discussed, horizontal angle 534 and vertical angle 536 of reaction chamber 506 help to direct fluid dispersion or movement between platen 502 and slide 522. In particular, vertical angle 536 causes edge 538 of platen 502 forming the length dimension and adjacent reagent drip surface 530 to be positioned higher than an opposite edge 540 of platen 502. Horizontal angle 534 causes end 542 of platen adjacent reagent drip surface 530 to be positioned lower than opposite end 544 of platen 502. Since corner 546 of platen 502 is higher than the diagonally opposed corner 548, air bubbles trapped between slide 522 and platen 502 can rise toward the higher edge/end of slide 522 and escape. In addition, when a fluid (e.g. reagent) is dispensed onto reagent drip surface 530, gravity draws the fluid downward toward the corner 548 of platen 502. As the fluid flows toward corner 548, it flows along end 542 of platen and the adjacent end of slide 522 and is drawn between slide 522 and platen 502 by capillary action. Once the fluid is between slide 522 and platen 502, capillary action further draws the fluid against gravity along the length of slide 522 toward the upper most corner 546 of platen 502.

Horizontal angle 534 of platen 502 also facilitates draining of reaction chamber 506 by preventing fluid from pooling along the bottom edge of slide 522. Instead, the fluid is drawn toward bottom corner 548 of platen 502 where a fluid outlet port is positioned so that the fluid can be removed through the outlet port. In addition, any overflow fluids are contained along bottom corner 548, preventing them from flowing over the top of slide 522.

Figure 6A:
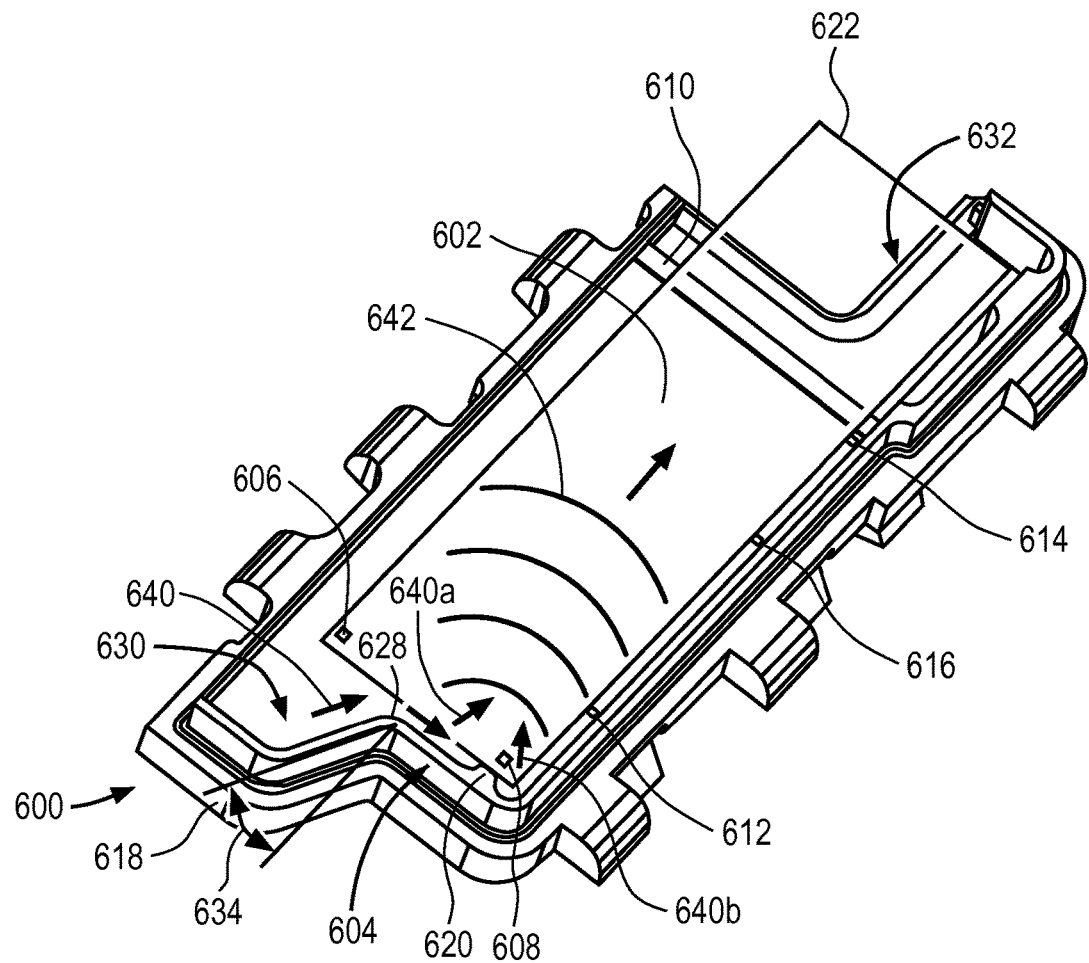
FIG. 6A illustrates a perspective view of an embodiment of a reaction chamber.
Figure 6B:
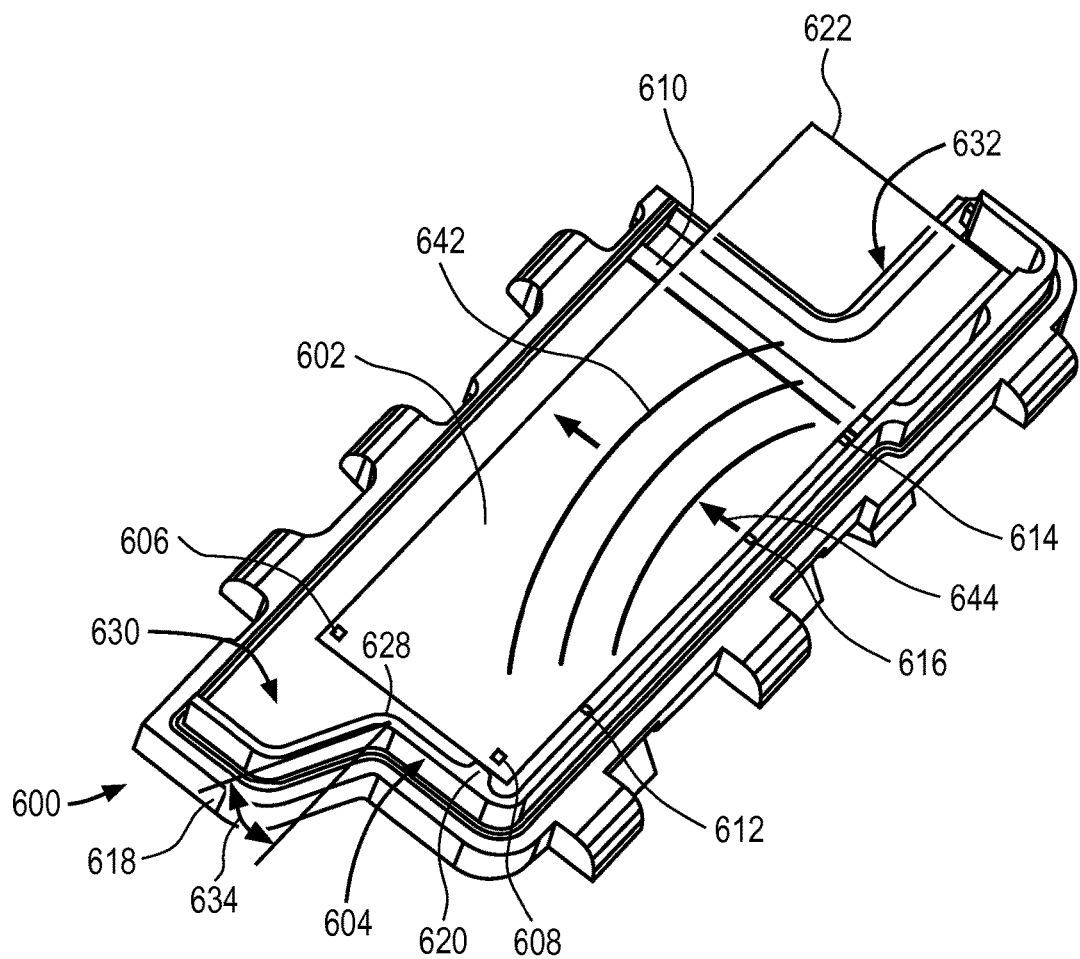
FIG. 6B illustrates a perspective view of an embodiment of a reaction chamber.

FIGS. 6A and 6B illustrate a perspective view of one embodiment of a reaction chamber. Reaction chamber 600 may be substantially the same as reaction chamber 300 described in reference to FIG. 3A. Reaction chamber 600 may include platen 602 dimensioned to support slide 622 thereon. Platen 602 may include reagent drip surface 630 at one end for receiving a reagent applied to platen 602 from above. An opposite end of platen 602 may include cut out portion 632 to facilitate grasping of slide 622 positioned on platen 602.

Wall 604 may be formed around a portion of platen 602 to retain a reagent placed on platen 602. Wall 604 may have a height sufficient to retain fluids that may pool within a corner formed by platen 602 and wall 604. Wall 604 may form bend 628 having angle 634 along an end of platen 602. Wall 604 may also include protrusion 620 to help distance slide 622 from wall 604.

Spacer nodules 606, 608 and spacer bar 610 may extend from a surface of platen 602 and create a gap between platen 602 and slide 622. Fluid outlet ports 612, 614 and fluid inlet port 616 may be formed through platen 602.

FIG. 6A illustrates a flow path of fluid between slide 622 and platen 602 when fluid is introduced from a fluid dispensing cartridge positioned above reaction chamber 600. In particular, the fluid (e.g. reagent) may be dispensed onto reagent drip surface 630. Due to the horizontal and vertical angles of reaction chamber 300 as well as bend 628 of wall 604 as previously discussed, the fluid follows flow path 640 along bend 628 of wall 604 and an edge of slide 622. Bend 628 of wall 604 provides a slope (angle 634) which slows the flow of the fluid flowing from reagent drip surface 630 toward slide 622. In particular, in the absence of bend 628, fluid would flow directly from reagent drip surface 630 down the edge of slide 622. Such a large amount of fluid would flow at such a speed that some of the fluid would flow over a side of slide 622 opposite platen 602. Angle 634 of bend 628 of wall 604 and the horizontal and vertical angles of reaction chamber 600 help to slow the fluid down and spread it along the edge of slide 622 to prevent such overflow.

Some of the fluid continues along wall 604 to the bottom corner of slide 622 while some of the fluid is immediately drawn between slide 622 and platen 602 by capillary action. The fluid that pools between wall 604 and the bottom corner of slide 622 is also drawn between slide 622 and platen 602 by capillary action. The fluid that is immediately drawn between slide 622 and platen 602 flows along flow path 640a while the fluid that initially pools at the corner of slide 622 follows flow path 640b. Flow path 640a and 640b eventually converge to form a single wave front 642 that travels across the length of slide 622 toward an opposite end of slide 622. Introducing the fluid between slide 622 and platen 602 at two different points allows the fluid to cover a substantial width of slide 622 across the entire length of slide 622. In this aspect, wave front 642 of the fluid is substantially even across an entire length of slide 622 thereby maximizing fluid coverage.

FIG. 6B illustrates a flow path of fluid between slide 622 and platen 602 when fluid is introduced through fluid inlet port 616. Fluid inlet port 616 is positioned off center with respect to a distance between spacer bar 610 and an opposite end of reaction chamber 600. Positioning of fluid inlet port 616 in this manner achieves a desired balance between the velocity with which the fluid introduced through fluid inlet port 616 travels across slide 622, the fluid coverage and the amount of air bubbles trapped between slide 622 and platen 602. In particular, it has been found that when the fluid is introduced through an inlet port positioned a greater distance from spacer bar 610 (e.g. 20 mm), the fluid travels across slide 622 at a slower speed and more air bubbles remain trapped between slide 622 and platen 602 then where fluid is introduced through an inlet port positioned closer to spacer bar 610 (e.g. 5 mm). Introducing the fluid at a slower speed (e.g. where inlet port 616 is a greater distance from spacer bar 610) allows for a more even wave front to travel across the slide and therefore better slide coverage. When the inlet port is positioned closer to spacer bar 610, the fluid flows at a higher velocity and there are fewer air bubbles but the fluid fills starting from spacer bar 610 and continues across slide 622 at an undesirable angle.

As illustrated in FIG. 6B, when fluid is introduced through inlet port 616 positioned off center (e.g. 15 mm to about 20 mm from spacer bar 610), fluid follows flow path 644 in a vertical direction across a width of slide 622. Flow path 644 has a substantially even wave front 642 allowing for optimal slide coverage.

Figure 7:
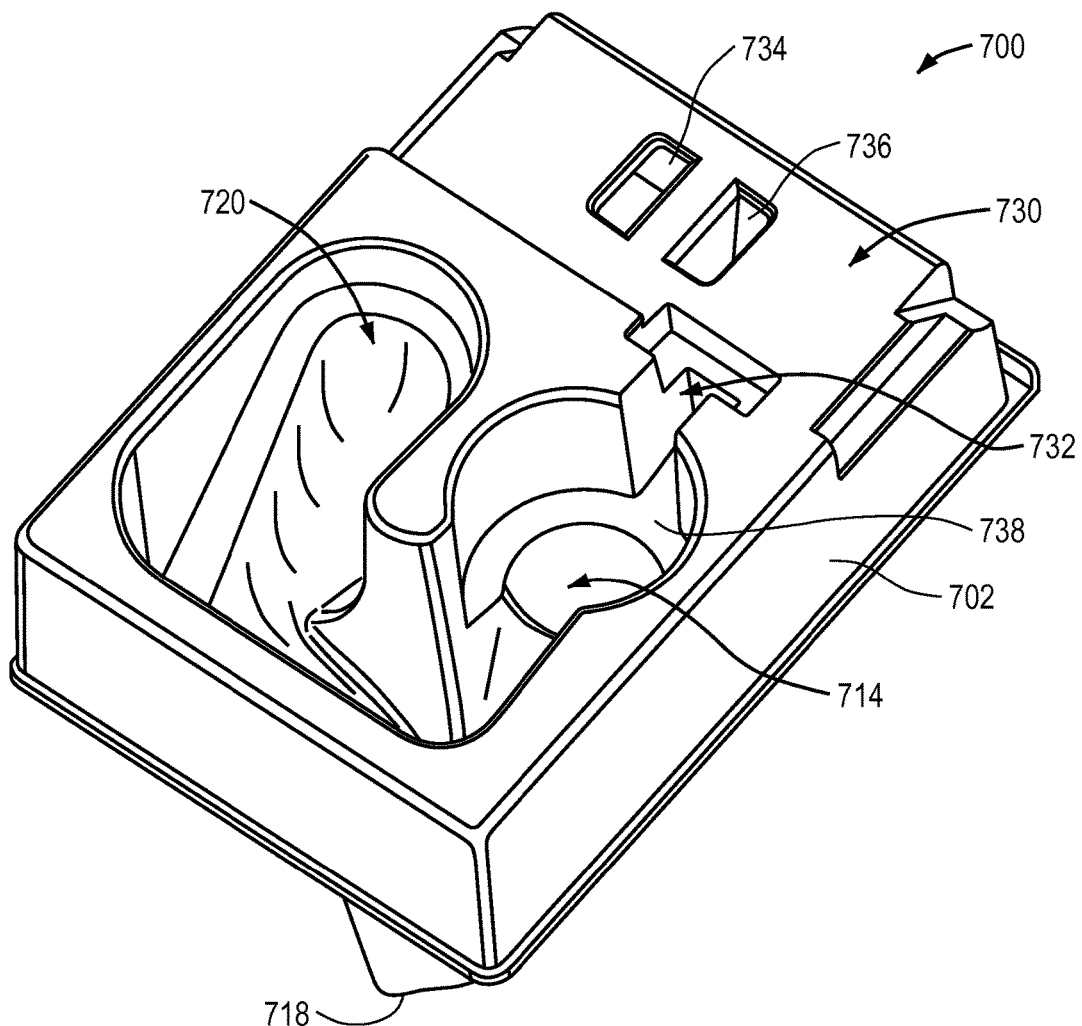
FIG. 7 illustrates a top perspective view of an embodiment of a reagent cartridge.

FIG. 7 illustrates a top perspective view of an embodiment of a reagent cartridge. Reagent cartridge 700 is substantially the same as reagent cartridge 408 described in reference to FIG. 4B except that in this embodiment the reagent capsule is removed so that features of reagent recess 714 can be more clearly seen. In this aspect, reagent cartridge 700 includes housing 702 which attaches to a support member such as that described in reference to FIG. 4A. Housing 702 includes reagent recess 714, channel 720 and indentation 730. Reagent recess 714 and channel 720 converge to form outlet channel 718.

As previously discussed, indentation 730 is dimensioned to receive a bracket (see bracket 424 of FIG. 4B) that is connected to the reagent capsule. FIG. 7 shows indentation 730 having slots 734, 736 dimensioned to receive bracket arms (see arms 922, 924 of FIG. 9A) extending from an underside of the bracket. The bracket arms are inserted into slots 734, 736 to position and hold the bracket on indentation 730 and, in turn, reagent capsule within reagent recess 714. Reagent recess 714 includes ledge 738 formed within reagent recess 714 to support a reagent capsule positioned therein. As can be seen from FIG. 7, ledge 738 extends from the wall of reagent recess 714 but does not close the opening of recess 714 so as to allow a reagent dispensed from the capsule to travel through reagent recess 714 to outlet channel 718.

Housing 702 further defines furrow 732 extending between indentation 730 and reagent recess 714. Furrow 732 is dimensioned to receive the connector connecting the bracket to the reagent capsule as previously discussed. Positioning of a bracket within indentation 730 and a connector within furrow 732 facilitates alignment of the reagent capsule within recess 714.

Figure 8:
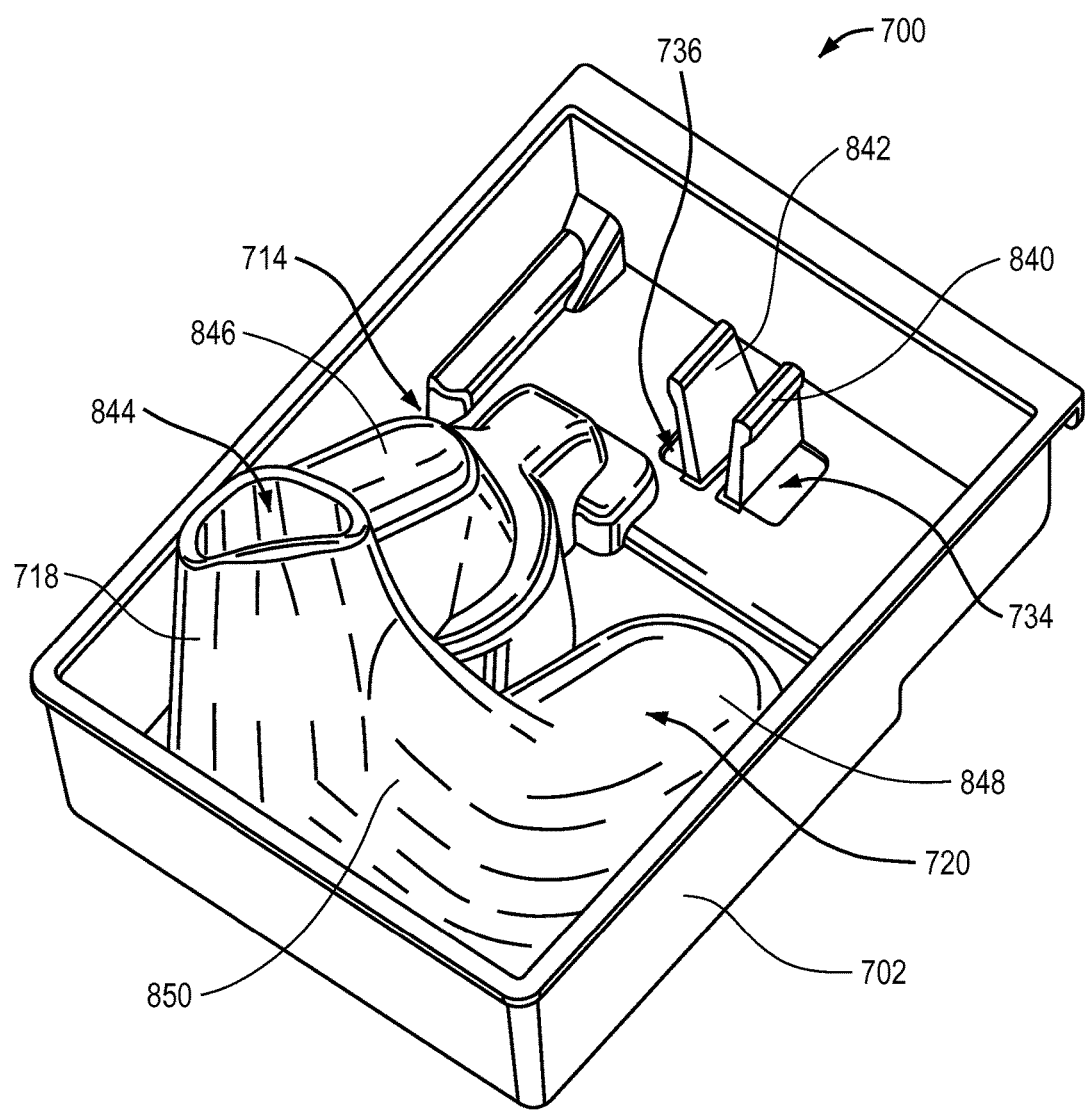
FIG. 8 illustrates a bottom perspective view of the reagent cartridge of FIG. 7.

FIG. 8 illustrates a bottom perspective view of the reagent cartridge of FIG. 7. From this view it can be seen that tabs 840, 842 extend from housing 702 below slots 734, 736, respectively. Tabs 840, 842 are dimensioned to position and hold reagent cartridge 700 on the upper portion of the support member (see upper portion 412 of support member 404 of FIG. 4A.) In this aspect, the support member may include slots within which tabs 840, 842 may be removably inserted. Tabs 840, 842, and in turn reagent cartridge 700, may be removed from the upper portion by pulling reagent cartridge in a direction away from the support member.

Slots 734, 736 may be dimensioned to receive arms extending from a bottom side of the bracket as illustrated in FIG. 9B. In this aspect, slots 734, 736 help to secure the bracket to reagent cartridge 700. The arms of the bracket may be removed from slots 734, 736 by pulling the bracket in a direction away from housing 702. Alternatively, the bracket may snap fit within slots 734, 736 such that to release the bracket from slots 734, 736.

Reagent recess 714 connects to outlet channel 718 via reagent recess channel 846. Reagent recess channel 846 provides a sloped surface along which a reagent from, for example, a capsule positioned within reagent recess 714 can travel in a direction toward outlet channel 718. Reagent recess channel 846 converges with channel 720.

Channel 720 includes first inclined portion 848 and second inclined portion 850. First inclined portion 848 is at a slope of approximately 30 degrees with respect to horizontal. Second inclined portion 850 extends from first inclined portion at a right angle toward reagent recess channel 846 and is further at a slope of approximately 30 degrees. The dimensions of channel 720 and reagent recess channel 846 are selected so that fluids traveling along the channels converge with one another and mix prior to being dispensed onto an underlying reaction chamber. In this aspect, multiple fluids may be mixed together and dispensed from outlet 844 of outlet channel 718. In addition, it is preferred that the various flow paths of reagent cartridge 700 (e.g. recess channel 846, channel 720 and outlet channel 718) have a tubular, rounded dimension to inhibit trapping of fluids traveling through the flow paths and minimize splashing when fluid is dispensed within the flow paths.

FIG. 9A illustrates a perspective view of an embodiment of a reagent dispensing capsule and bracket. Capsule 900 includes container 902 dimensioned to hold a reagent therein. Seal 930 may be positioned across the opening of container 902 to retain the reagent. Within capsule 900 is plunger 904. Plunger 904 may be an elongated structure having one end attached to the closed end of container 902 and an opposite end extending toward the opening of container 902. The end of plunger 904 positioned at the opening of container 902 may be adapted for piercing through seal 930 formed across the opening of container 902. Representatively, the end of plunger 904 may have one or more spikes extending from the end. During operation, a force is applied to the closed end of container 902 causing container 902 to collapse and push plunger 904 in a direction of seal 930. Plunger 904 contacts and punctures seal 930, thereby opening the end of container 902 to allow for release of the reagent contained therein.

Reagent capsule 900 may be attached to bracket 910 by connector 906 as previously discussed. In this aspect, connector 906 may have attachment end 908 which fits into receiving slot 916 formed by bracket 910. Bracket 910 may have top side 912 and back side 914 which are formed at right angles to one another. In this aspect, when bracket 910 is attached to the reagent cartridge (e.g. reagent cartridge 700 of FIG. 7), top side 912 is positioned within the indentation (e.g. indentation 730 of FIG. 7) formed along a top side of the reagent cartridge. Back side 914 of bracket 910 overlaps a back side of the reagent cartridge.

Identifiers 918, 920 may be positioned on bracket 910. Identifiers 918, 920 may contain machine understandable codes, such as provided by radio frequency identification (RFID) tags, shape identifiers, color identifiers, numbers or words, other optical codes, barcodes etc. Identifiers 918, 920 may be used to identify, for example, the contents of capsule 902 and/or a processing protocol. Still further, one or more of identifiers 918, 920 may contain patient information and history, information regarding biological sample(s) on the slides, arrival and departure times of biological samples, tests performed on the samples, diagnoses made and so on. Identifiers 918, 920 may contain the same or different information.

In some embodiments, one or more of identifiers 918, 920 may be removable so that the identifier can be attached to another article of the system. For example, identifier 918 may contain information identifying a reagent contained within capsule 902 and/or a processing protocol. Identifier 920 may contain the same information. Prior to processing a slide using the contents (e.g. reagent) of capsule 902, identifier 918 may be removed from bracket 910 and positioned on the slide. Alternatively, identifier 918 can be positioned on the slide after processing. The reagent and/or process performed on the slide can then be readily determined from identifier 918 on the slide. The ability to transfer identifiers in this manner helps to prevent processing and identification errors.

FIG. 9B illustrates a perspective view of the reagent dispensing capsule and the bracket of FIG. 9A. From this view, bracket arms 922, 924 extending from a bottom surface of bracket 910 can be seen. When bracket 910 is positioned within the indentation (e.g. indentation 730 of FIG. 7) of the reagent cartridge (e.g. reagent cartridge 700 of FIG. 7), bracket arms 922, 924 fit within the slots (e.g. slots 734, 736 of FIG. 7) formed in the indentation of the reagent cartridge to hold bracket 910, and in turn, capsule 900, in place. Bracket arms 922, 924 catch on the wall of the reagent cartridge forming slots 734, 736 (see FIG. 8), respectively to lock bracket 910 in place. In this aspect, bracket arms 922, 924 may have any size or dimensions complimentary to slots 734, 736 of reagent cartridge 700.

Figure 10A:
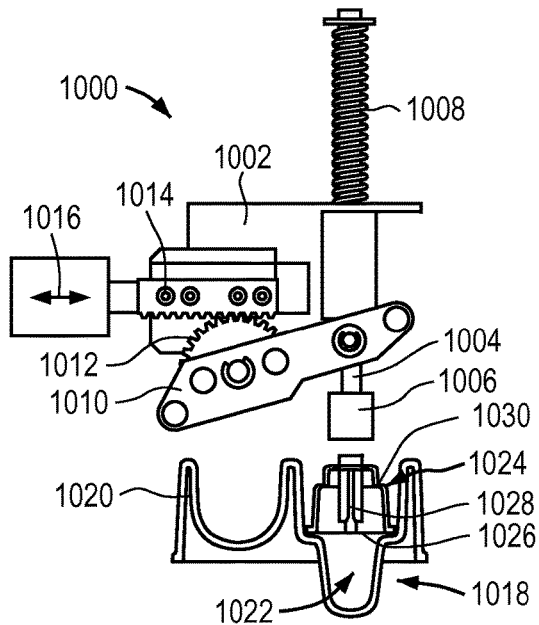
FIG. 10A illustrates a cross sectional side view of an embodiment of a capsule pressing mechanism during operation.

FIGS. 10A-10D illustrate a cross sectional side view of a capsule pressing mechanism during operation. FIG. 10A illustrates capsule pressing mechanism 1000 in a raised position such that it does not contact the underlying reagent capsule 1024. Capsule pressing mechanism 1000 includes housing 1002 for supporting components of pressing mechanism 1000. The components of pressing mechanism 1000 may include piston 1004 having head member 1006 positioned at one end. Spring member 1008 may further be positioned around an opposite end of piston 1004 to bias piston 1004 in a raised position.

Crank shaft 1010 may be attached to piston 1004 to drive vertical movement of piston 1004. Crank shaft 1010 may be rotatably attached to piston 1004 at one end and gear 1012 at an opposite end. Gear 1012 may be rotated by lateral movement of slide arm 1014. Slide arm 1014 may include teeth along one side which are complimentary to the teeth of gear 1012. Lateral movement of slide arm 1014 causes the teeth of slide arm 1014 to engage with the teeth of gear 1012 and rotate gear 1012 in a clockwise or counter clockwise direction. Rotation of gear 1012 in turn causes the end of crank shaft 1010 attached to piston 1004 to move vertically. When the end of crank shaft 1010 moves in an upward direction, piston 1004 is raised and when crank shaft 1010 moves in a downward direction, piston 1004 is lowered. Lateral movement of slide arm 1014 may be driven by actuator 1016. Actuator 1016 may be any type of actuating mechanism capable of driving lateral movement of slide arm 1014. Representatively, actuator 1016 may be a unit including a motor and a gear which may be engaged with a gear located on an opposite side of slide arm 1014.

Reagent cartridge 1018 may be positioned below capsule pressing mechanism 1000. Reagent cartridge 1018 may be substantially the same as reagent cartridge 408 described in reference to FIG. 4B. In this aspect, reagent cartridge 1018 includes reagent recess 1022 for holding reagent capsule 1024. Reagent cartridge 1018 further includes channel 1020. Reagent capsule 1024 includes container 1030 having one end sealed with seal 1026. Seal 1026 may be any type of seal capable of being punctured by plunger 1028 to release contents within reagent capsule 1024. Representatively, seal 1026 may be a heat seal made of a metal foil or plastic material.

Figure 10B:
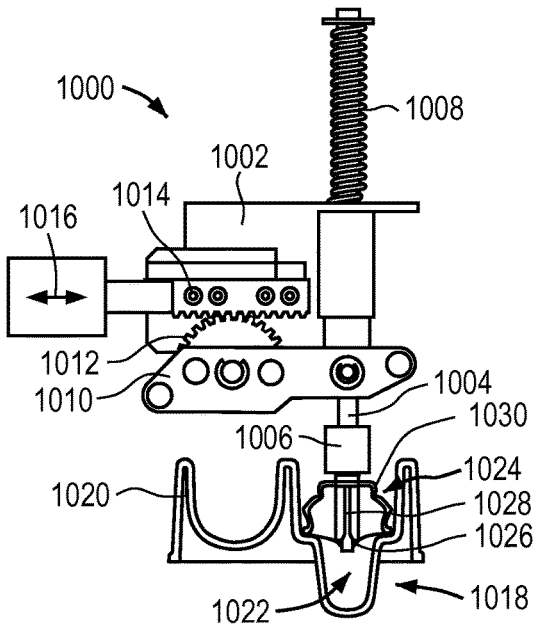
FIG. 10B illustrates a cross sectional side view of an embodiment of a capsule pressing mechanism during operation.
Figure 10C:
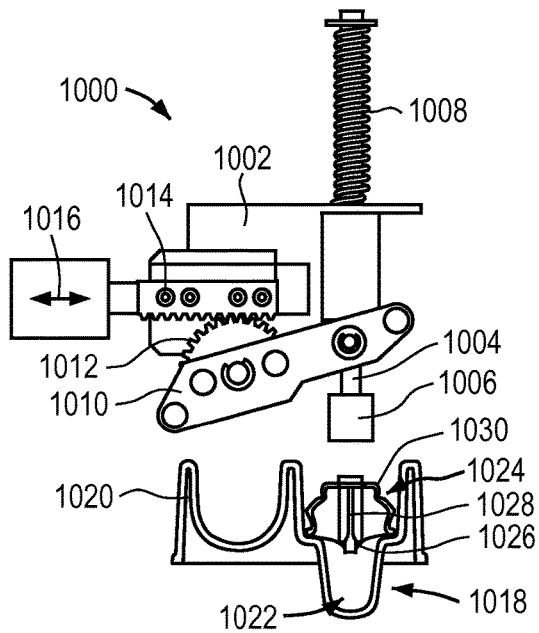
FIG. 10C illustrates a cross sectional side view of an embodiment of a capsule pressing mechanism during operation.
Figure 10D:
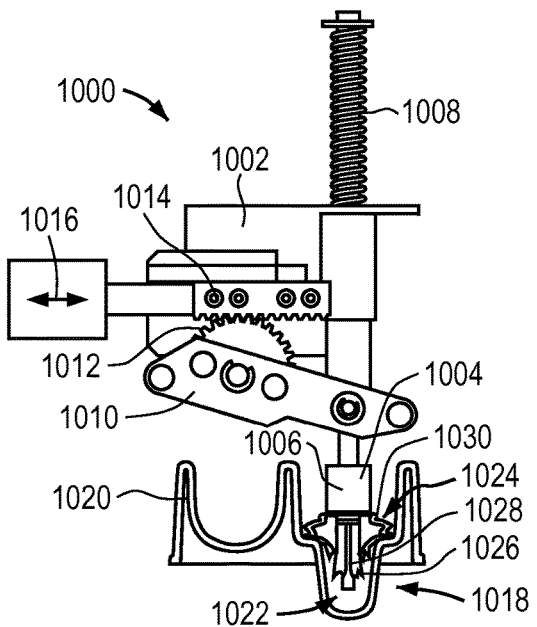
FIG. 10D illustrates a cross sectional side view of an embodiment of a capsule pressing mechanism during operation.

In some embodiments, breaking of seal 1026 and release of a reagent from reagent capsule 1024 is accomplished by a two step process as illustrated by FIGS. 10B, 10C and 10D. In particular, during operation, pressing mechanism 1000 drives piston 1004 vertically in a direction toward reagent capsule 1024. Head 1006 of piston 1004 presses on reagent capsule 1024, collapsing capsule 1024 and driving plunger 1028 through seal 1026 as illustrated in FIG. 10B. A stroke length of piston 1004 is controlled so that once seal 1026 is broken, vertical movement of piston 1004 is reversed and piston 1004 is raised as illustrated in FIG. 10C. During the initial downward piston stroke, only a small amount of reagent from capsule 1024 is released. Raising of piston 1004 allows a small amount of air into capsule 1024. The downward vertical movement of piston 1004 is then recommenced and head 1006 of piston 1004 completely collapses capsule 1024 causing ejection of the entire contents held within capsule 1024 as illustrated in FIG. 10D.

It has been found that breaking of the seal and releasing the entire contents of capsule 1024 with one stroke of piston 1004 causes some of the reagent held within capsule 1024 to splash out of capsule 1024 resulting in loss of some of the reagent. Such splashing can be reduced or eliminated using a first piston stroke to puncture seal 1026, allowing some air to enter capsule 1024 and then a second piston stroke to eject the remaining contents of capsule 1024. Once all the reagent is ejected from capsule 1024, piston 1004 is raised back to its initial position as illustrated in FIG. 10A.

Figure 11:
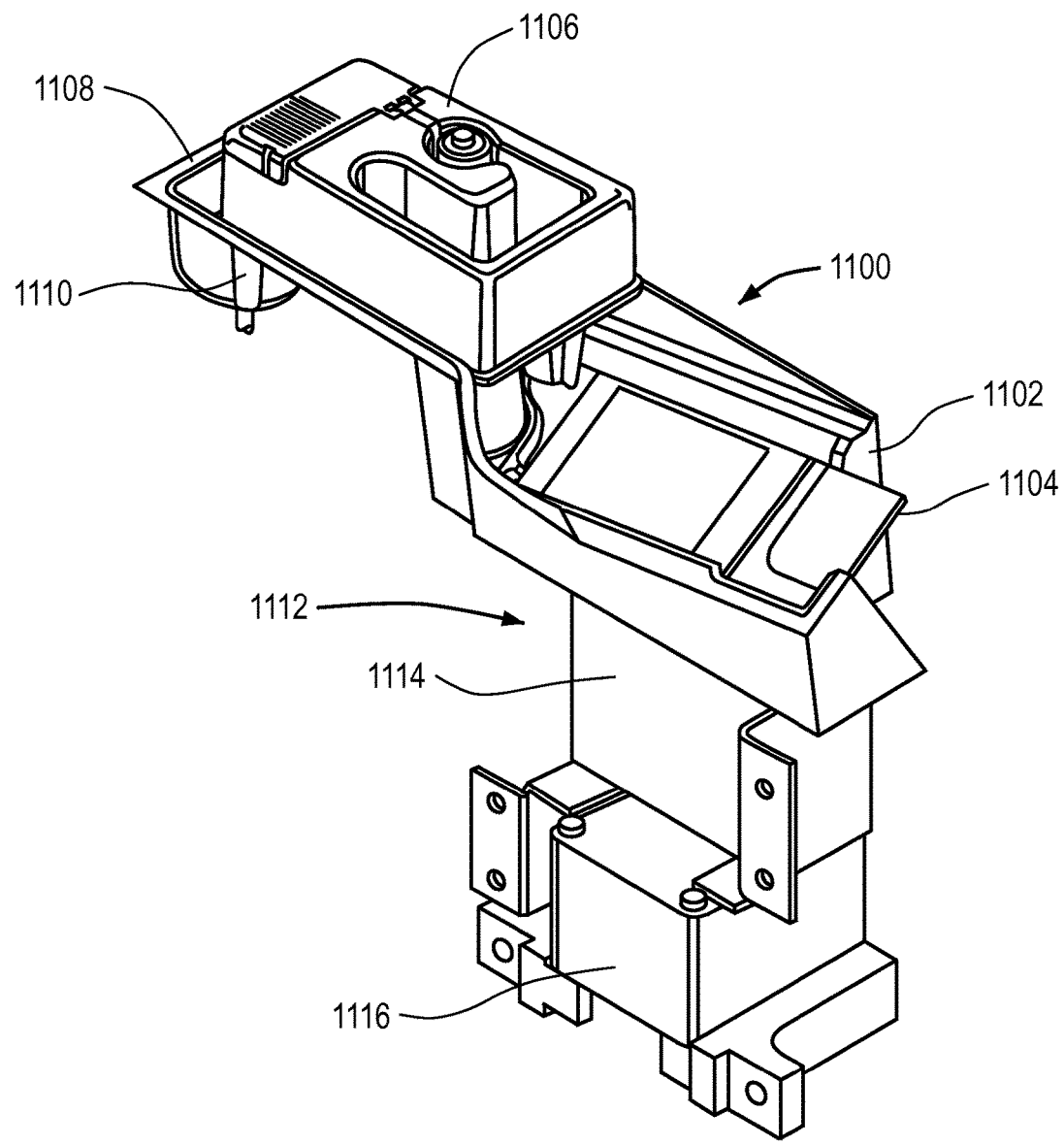
FIG. 11 is a perspective view of an embodiment of a reaction station of a sample processing system.

FIG. 11 is a perspective view of a reaction station of a sample processing system. Reaction station 1100 includes support member 1102 having reaction chamber 1104 and reagent cartridge 1106 positioned thereon. Support member 1102, reaction chamber 1104 and reagent cartridge 1106 may be substantially the same as support member 404, reaction chamber 406 and reagent cartridge 408 described in reference to FIG. 4A.

As can be seen from this view, reaction station 1100 further includes reservoir 1108. Reservoir 1108 may be used to hold a bulk reagent that is to be supplied to reaction chamber 1104 during processing. In this aspect, reservoir 1108 is attached to support member 1102 and is in fluid communication with reaction chamber 1104. Typically in sample processing systems, there are several reagents that must be applied to the reaction chamber at various times during processing. Such reagents are normally contained in bulk containers and separate supply lines must run from the container to each reaction chamber. Reservoir 1108, however, eliminates the need for multiple supply lines. Instead, as will be described in more detail in reference to FIG. 16A, FIG. 16B and FIG. 17, supply lines from each bulk container run to a single bulk dispenser. The bulk dispenser may then be positioned over reservoir 1108 to dispense the desired bulk reagent into reservoir 1108. Aliquots of the fluid contained within reservoir 1108 may then be removed and applied to reaction chamber 1104 according to the processing protocol. Such configuration is particularly advantageous where multiple reaction chambers are present in the system because it allows the desired fluid to be applied to each reaction chamber at any time. This is in contrast to typical processing systems in which application of a fluid from the bulk container to one reaction chamber may be delayed until application of the fluid to another reaction chamber is completed.

Reservoir 1108 may have dimensions suitable for holding a volume of liquid needed to complete processing within the reaction chamber 1104. For example, reservoir 1108 may hold a volume of, for example, up to 10 ml, in some embodiments about 6 ml. Aliquots in the amount of, for example, 500 microliters (µl), may be transferred from reservoir 1108 to reaction chamber 1104 at desired times during processing. A supply line (not shown) may run from reservoir 1108 to reaction chamber 1104 along support member 1102 to transfer the fluid from reservoir 1108 to reaction chamber 1104.

Waste line 1110 may be connected to reservoir 1108. Waste line 1110 may facilitate removal of excess fluids from reservoir 1108 and/or changing of a fluid held within reservoir 1108.

Reaction station 1100 may further include a temperature modifying assembly 1112 to heat and cool reaction chamber 1104. It is important during processing of a sample within reaction chamber 1104 that the platen of reaction chamber 1104 is able to be heated and cooled as desired. Rapid cooling is important during, for example, antigen retrieval, particularly after steps involving heating of reaction chamber 1104. In this aspect, temperature modifying assembly 1112 is positioned below reaction chamber 1104. Temperature modifying assembly 1112 may include a thermoelectric cooler (TEC) (see TEC 1206, 1204 described in reference to FIG. 12), heat sink 1114 and fan 1116 as will be discussed in more detail in reference to FIG. 12.

Figure 12:
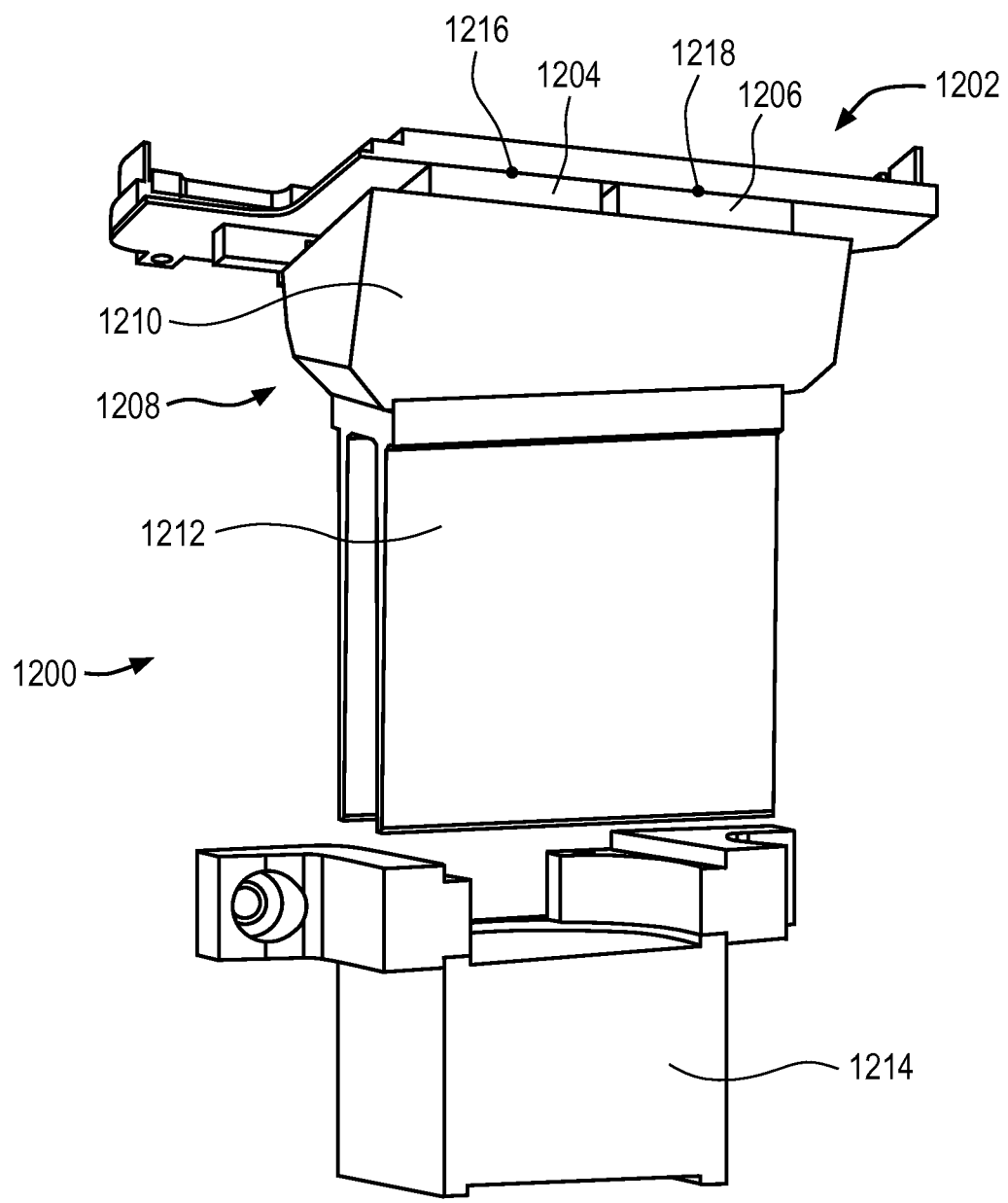
FIG. 12 illustrates a perspective view of an embodiment of a temperature modifying assembly.

FIG. 12 illustrates a perspective view of one embodiment of a temperature modifying assembly. Temperature modifying assembly 1200 may include reaction chamber 1202, TEC 1204 and 1206, heat sink 1208 and fan 1214. TEC 1204 and 1206 may be positioned in a side by side configuration along an underside of reaction chamber 1202. TEC 1204 and 1206 may be used to either heat or cool reaction chamber 1202. To cool reaction chamber 1202, heat from a side of TEC 1204 and 1206 contacting reaction chamber 1202 is transferred to an opposite side of TEC 1204 and 1206. To heat reaction chamber 1202, transfer of heat is reversed in that it is transferred from the side of TEC 1204 and 1206 opposite reaction chamber 1202 to the side contacting reaction chamber 1202. TEC 1204 and 1206 may be any TEC device such as that commercially available from Ferrotec Corporation under the model number 9501/071/040BS/L300.

Heat sink 1208 and fan 1214 may facilitate heat transfer within TEC 1204 and 1206. In particular, heat sink 1208 may include base portion 1210 attached to a surface of TEC 1204 and 1206 and fin portion 1212. Base portion 1210 may be a solid block made of a heat transferring material, for example, aluminum. In this aspect, base portion 1210 may be used to increase a heat capacity of heat sink 1208. Fin portion 1212 extends from base portion 1210. Heat from TEC 1204 and 1206 is absorbed by base portion 1210 and dissipated into the air through fin portion 1212. TEC 1204 and 1206 and heat sink 1208 allow for direct cooling and/or heating of reaction chamber 1202.

Fan 1214 is positioned so that it blows air onto fin portion 1212 to facilitate heat dissipation. A speed of fan 1214 may be fixed or controlled by a user and modified depending upon the level of heat dissipation desired. Representatively, where rapid cooling of TEC 1204 and 1206, and in turn reaction chamber 1202, is desired, a speed of fan 1214 may be increased in order to increase a circulation of air throughout fin 1212. In this aspect, temperature modifying assembly 1200 may be capable of rapidly cooling reaction chamber 1202 from a temperature of 98 degrees Celsius to 10 degrees Celsius within 5 minutes, for example, in less than 3 minutes.

In some embodiments, temperature modifying assembly 1200 may further include one or more thermistors. Representatively, thermistors 1216 and 1218 may be sandwiched between reaction chamber 1202 and TEC 1204 and 1206, respectively. Thermistors 1216 and 1218 may be used for monitoring and/or controlling a temperature of temperature modifying assembly 1200. In particular, thermistors 1216 and 1218 may measure a temperature of reaction chamber 1202. This temperature may be used to determine whether a temperature of TEC 1204 and 1206 should be maintained or modified.

Figure 13:
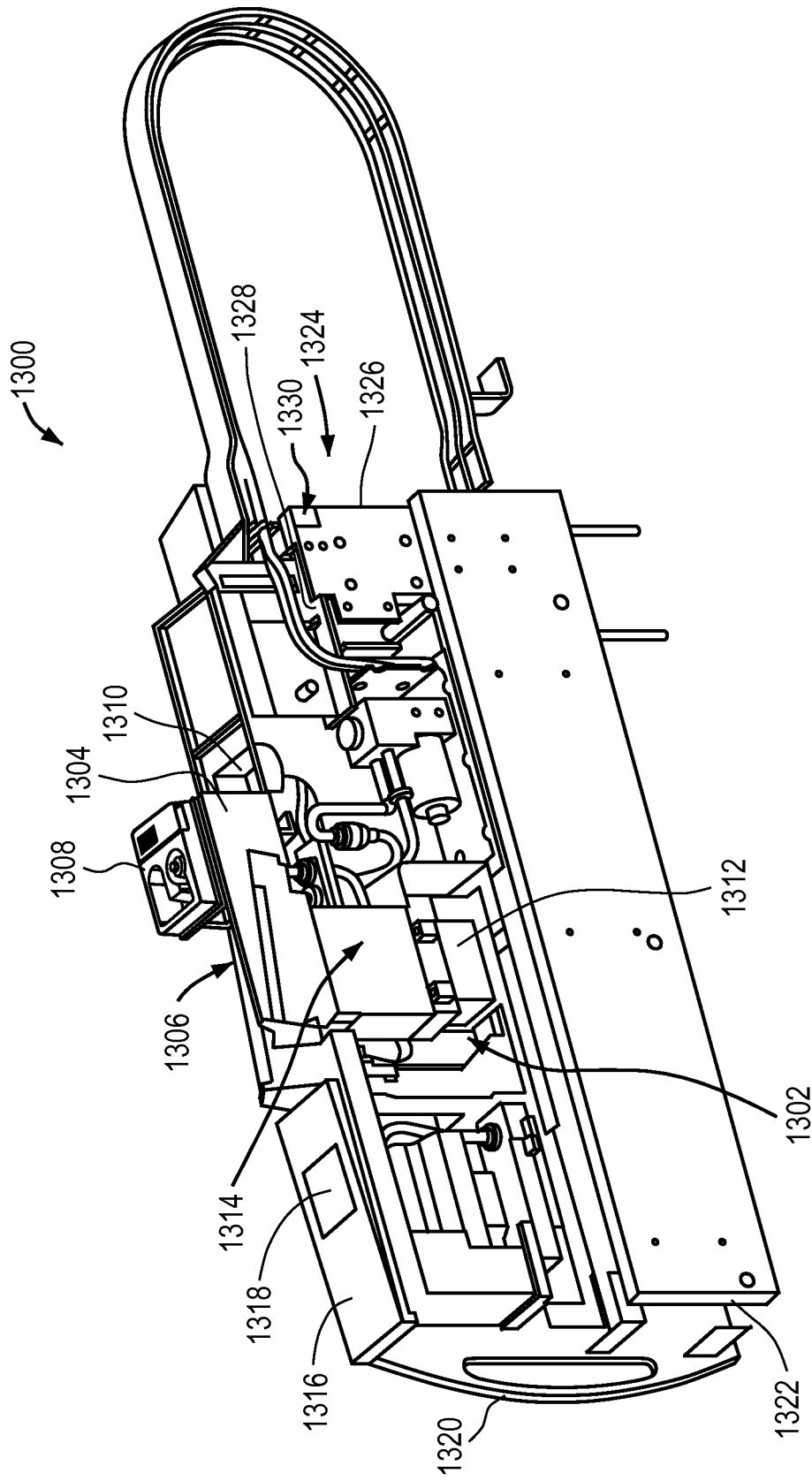
FIG. 13 illustrates a perspective view of an embodiment of an entire reaction station.

FIG. 13 illustrates a perspective view of an embodiment of an entire reaction station. Reaction station 1300 includes a reaction station similar to reaction station 1100 previously discussed in reference to FIG. 11 and includes temperature modifying assembly 1302 similar to temperature modifying assembly 1200 previously discussed in reference to FIG. 12. Reaction station 1300 includes support member 1304 having reaction chamber 1306 and reagent cartridge 1308 positioned therein. Reaction station 1300 further includes reservoir 1310. A TEC device (not illustrated), heat sink 1314 and fan 1312 such as that previously discussed in reference to FIG. 12 are positioned beneath reaction chamber 1306.

Reaction station 1300 further includes identification platform 1316 and handle portion 1320. Identification platform 1316 is positioned at an end of reaction station 1300 that is viewable by a user. Identification platform 1316 may include identifier 1318 which identifies reaction station 1300. As previously discussed, the sample processing system may include more than one reaction station 1300 so that processing of multiple samples may occur at one time. It is therefore desirable to identify each reaction station 1300 with identifier 1318 so that the user and/or system can identify the reaction station processing a particular sample and/or a location of the sample. Identifier 1318 may be any of the previously discussed types of identifiers, for example, radio frequency identification (RFID) tags, shape identifiers, color identifiers, numbers or words, other optical codes, barcodes, etc.

As previously discussed in reference to FIG. 1, reaction station 1300 may slide in and out of a reaction compartment (see reaction compartment 104 illustrated in FIG. 1) formed by a housing (see housing 102 illustrated in FIG. 1) to facilitate access to reaction chamber 1306 mounted therein. Rail member 1322 may be connected to the housing and provide a surface along which reaction station 1300 may slide. Representatively, rail member 1322 may include a channel to guide reaction station 1300 in and out of the reaction compartment. Handle 1320 extending from an end of reaction station 1300 may be used to slide reaction station 1300 in and out of the reaction compartment.

Interlock assembly 1324 may be connected to an end of reaction station 1300 opposite handle 1320. FIG. 13 illustrates a back side view of interlock assembly 1324. Interlock assembly 1324 may be any type of interlocking system capable of locking reaction station 1300 within the reaction compartment and preventing its removal. In some embodiments, interlock assembly 1324 may include an electromechanical locking system. Representatively, interlock assembly 1324 may include a bistable solenoid. It is desirable that interlock assembly 1324 remains locked in the event of a power failure in order to prevent improper removal of reaction station 1300. Representatively, in the event of a power failure, interlock assembly 1324 remains in the locked position until a user purposely unlocks interlock assembly 1324. Interlock assembly 1324 may serve as a secondary locking system for each individual reaction station 1300 while a primary locking system may be provided for locking the system housing (e.g. cover member 108 and door member 110 of reaction compartment 104 discussed in reference to FIG. 1). The primary locking system may unlock the system in the event of a power failure to allow a user access to each reaction station 1300, however, removal of reaction station 1300 may still be prevented by interlock assembly 1324.

Figure 14:
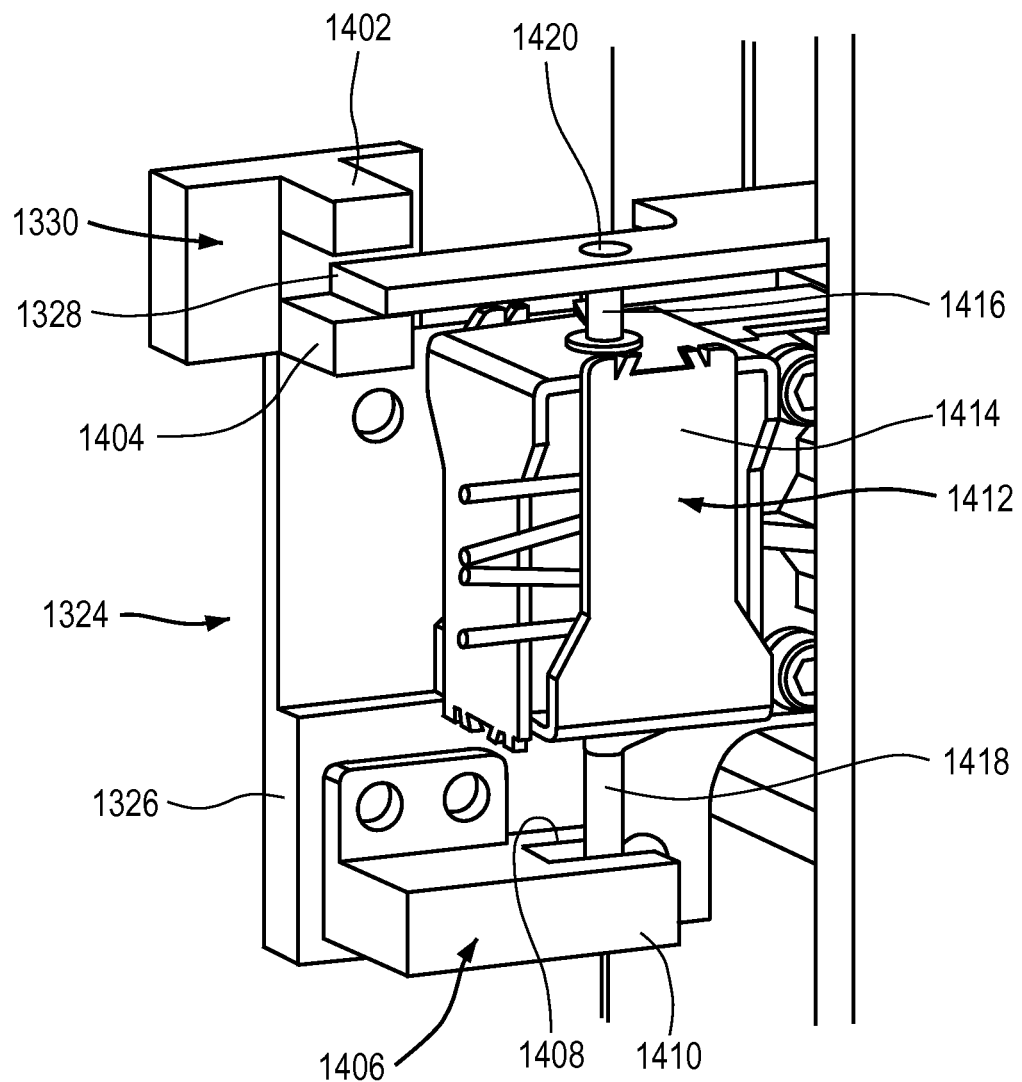
FIG. 14 illustrates a front perspective view of an embodiment of an interlock assembly.

FIG. 14 illustrates a front perspective view of the interlock assembly described in reference to FIG. 13. Interlock assembly 1324 may include electromechanical locking system 1412. In some embodiments, electromechanical locking system 1412 may be a bistable solenoid such as that available commercially from Takano Co., LTD under product number TSB-0805-SS1. Frame member 1326 for supporting bistable solenoid 1412 may be attached to rail member 1322 of the reaction compartment. Bistable solenoid 1412 may generally include solenoid housing 1414 attached to frame member 1326. Thrust pin 1416 may extend from an upper end of housing 1414 and plunger 1418 may extend from a lower end of housing 1414. Thrust pin 1416 and plunger 1418 are connected and move simultaneously in a vertical direction. Thrust pin 1416 is used for locking or unlocking reaction station 1300 and plunger 1418 is used for detecting locking or unlocking of reaction station 1300.

Lock arm 1328 of reaction station 1300 may include aperture 1420 dimensioned to receive thrust pin 1416. Aperture 1420 is positioned within lock arm 1328 such that when reaction station sensor 1330 detects the presence of lock arm 1328, aperture 1420 is aligned with thrust pin 1416. Thrust pin 1416 may then be advanced toward lock arm 1328 and through aperture 1420 to lock reaction station 1300 in place. Bistable solenoid 1412 allows thrust pin 1416 to be held in the locked position even after power is disconnected. Where power is lost and unlocking of interlock assembly 1324 is desired, a tool may be used to dislodge thrust pin 1416 from within aperture 1420.

Reaction station sensor 1330 may be used to detect the presence of reaction station 1330 within the reaction compartment. Reaction station sensor 1330 including detection arms 1402 and 1404 is attached to frame member 1326. A space may be provided between detection arms 1402 and 1404 on reaction station sensor 1330 for receiving lock arm 1328. Detection arms 1402 and 1404 may include sensor elements to detect the presence or absence of lock arm 1328. Representatively, arm 1402 may emit a laser beam toward a beam detector on arm 1404. When the laser beam is interrupted by lock arm 1328, the detector on arm 1404 no longer detects the beam from arm 1402. The system is then alerted that reaction station 1300 is in position and may be locked in place. Similarly, when the laser beam is detected by the laser beam detector on arm 1404 (i.e. lock arm 1328 is not between arms 1402, 1404), interlock assembly 1324 remains in the unlocked position. Reaction station sensor may include a variety of types of sensors and/or switches, including, but not limited to, optical sensors and read switches.

Interlock sensor 1406 to detect the position (locked or unlocked) of interlock assembly 1324 may further be attached to frame member 1326. Similar to reaction station sensor 1330, interlock sensor 1406 may include detection arms 1408 and 1410. Detection arm 1408 may include a laser beam directed toward a laser beam detector on arm 1410. In this aspect, detection arms 1408 and 1410 can detect the position (lock or unlock) of interlock assembly 1324.

The reaction station position information obtained from reaction station sensor 1330 and/or interlock sensor 1406 may be used to detect the introduction of a new slide to the system during processing. For example, in an embodiment where there are 30 reaction stations 1300 within the system, a user may initially position slides at 20 reaction stations 1300. The remaining 10 reaction stations may be empty. Each of reaction stations 1300 are initially scanned to determine whether a slide and corresponding reagent cartridge are positioned thereon. The appropriate processing protocols will then be performed at only stations having slides and reagent cartridges therein. If, during processing, a user wants to add a slide to one of the empty reaction stations, the user opens the reaction chamber and slides an empty reaction station out, places the slide and reagent cartridge on the station and then slides it back in. The sensors detect that one of reaction stations 1300 has been removed and slid back into a locked position. Based on this information, the system then knows to scan the station and process the new slide.

FIG. 15 illustrates a perspective view of one embodiment of an overhead fluid dispensing system and capsule pressing mechanism. Fluid dispensing system 1500 generally includes fluid dispensing assembly 1502 used to dispense a fluid onto a reaction chamber of an underlying reaction station. Fluid dispensing assembly 1502 is attached to mounting assembly 1506. Capsule pressing mechanism 1504 for facilitating release of a reagent from a reagent capsule within a reagent cartridge of reaction station may further be attached to mounting assembly 1506. Fluid dispensing assembly 1502 and capsule pressing mechanism 1504 may be positioned within mounting stations (see mounting stations 1618 of FIG. 16A) of mounting assembly 1506. Although one fluid dispensing assembly 1502 and capsule pressing mechanism 1504 are illustrated in FIG. 15, it is contemplated that any number of fluid dispensing assembly 1502 and capsules pressing mechanism 1504 may be mounted to mounting assembly 1506. Representatively, in one embodiment, mounting assembly 1506 may include at least 20 mounting stations having at least 19 fluid dispensing assemblies 1502 and at least one capsule pressing mechanism 1504 mounted thereto. In some embodiments which have two capsule pressing mechanisms, capsule pressing mechanism 1504 may be mounted at a side of mounting assembly 1506 opposite a second capsules pressing mechanism.

Mounting assembly 1506 may be substantially the same as mounting assembly 116 disclosed in reference to FIG. 1. In one embodiment, mounting assembly 1506 may be a carousel that is rotatable about a central axis so as to align fluid dispensing assembly 1502 and/or capsule pressing mechanism 1504 with a reagent cartridge or reagent capsule positioned below mounting assembly 1506. Mounting assembly 1506 may also be linearly translatable such that fluid dispensing assembly 1502 and capsule pressing mechanism 1504 may move from one reaction station to the next.

Fluid dispensing assembly 1502 may be any fluid dispensing assembly 1502 suitable for dispensing a fluid onto an underlying reagent cartridge. Representatively, in one embodiment, fluid dispensing assembly 1502 may include fluid dispensing cartridge 1508 connected to cartridge pump assembly 1510. Fluid dispensing cartridge 1508 may include a container for holding a fluid (e.g. a reagent) connected to a tube member for dispensing the fluid onto an underlying reagent cartridge. Cartridge pump assembly 1510 may be a pump mechanism dimensioned to pump the fluid from fluid dispensing cartridge 1508.

Capsule pressing mechanism 1504 may also be mounted to mounting assembly 1506. Capsule pressing mechanism 1504 may be substantially the same as capsule pressing mechanism 1000 described in reference to FIGS. 10A-10D. In this aspect, capsule pressing mechanism 1504 may include housing 1516 and piston 1512. Spring member 1514 may further be positioned around piston 1512 to bias piston 1512 in a raised position. An actuator (not shown) as previously discussed in reference to FIGS. 10A-10D may be positioned concentrically inward from capsule pressing mechanism 1504 to drive movement of piston 1512.

During operation, mounting assembly 1506 moves from one reaction station to the next and may further rotate to align fluid dispensing assembly 1502 and capsule pressing mechanism 1504 with the desired station. In some embodiments, mounting assembly 1506 having fluid dispensing cartridges therein may complete a cycle (e.g. complete a pass by each reaction station) every 3 minutes. In this aspect, where there are 30 reaction stations, mounting assembly 1506 passes by each reaction station every 6 seconds, with approximately 2-3 seconds at each reaction station for dispensing of the reagent.

Figure 16A:
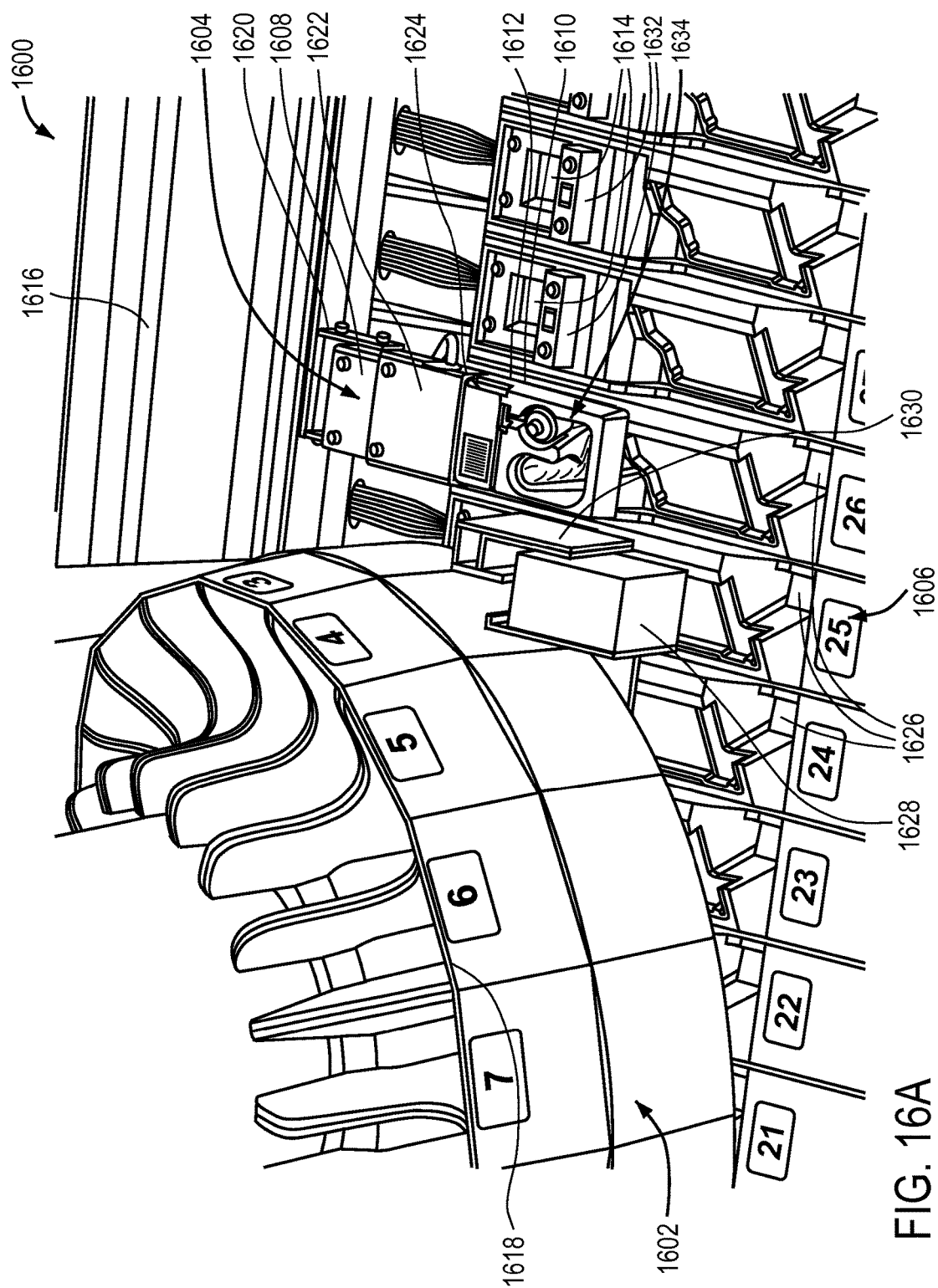
FIG. 16A illustrates a perspective view of an embodiment of an overhead fluid dispensing system.
Figure 16B:
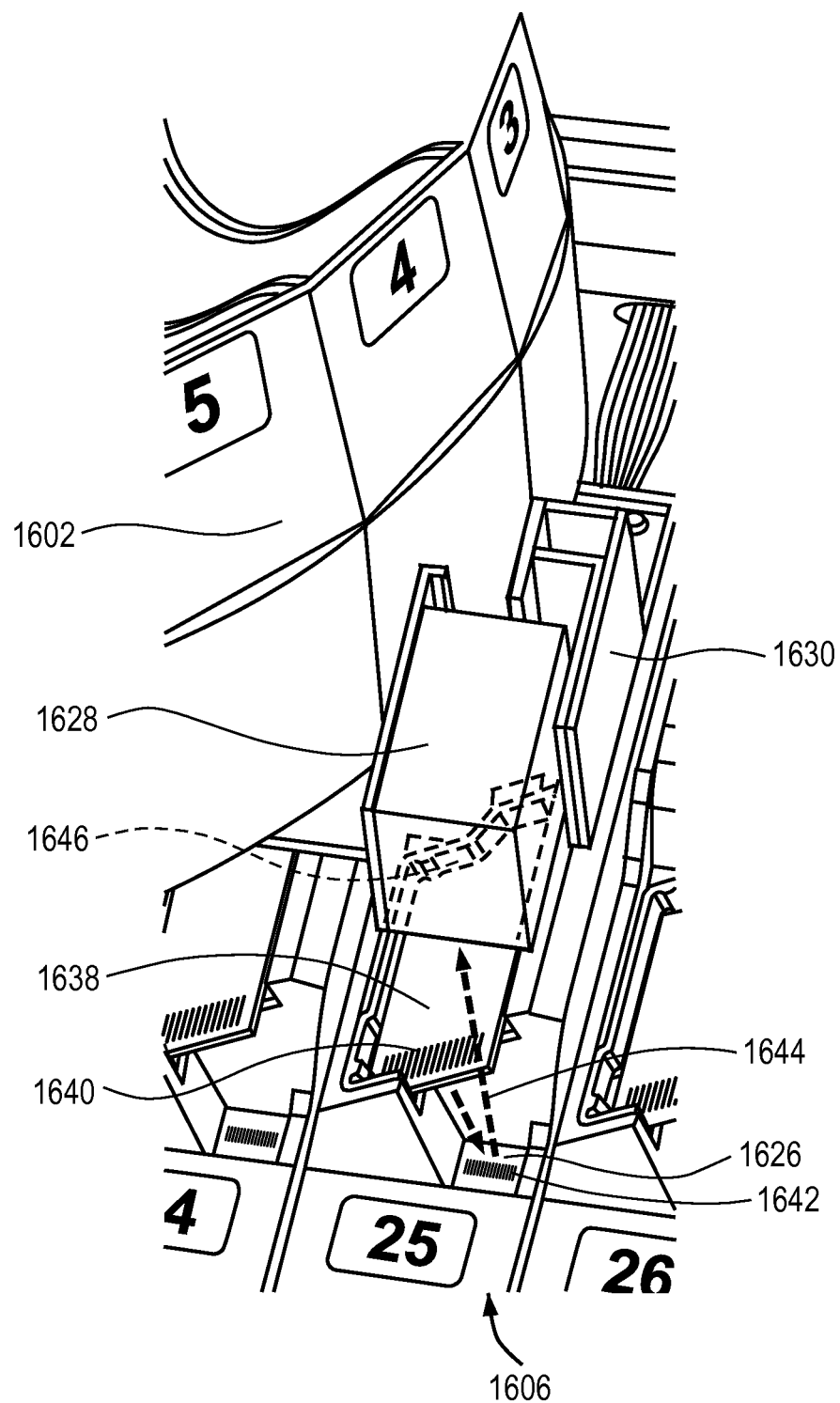
FIG. 16B illustrates a perspective view of an embodiment of an overhead fluid dispensing system.

FIGS. 16A and 16B illustrate perspective views of one embodiment of an overhead fluid dispensing system. Referring to FIG. 16A, fluid dispensing system 1600 generally includes fluid dispensing assembly 1602 and bulk reagent dispenser 1604. Fluid dispensing assembly 1602 is substantially similar to fluid dispensing assembly 1502 described in reference to FIG. 15. In this aspect, fluid dispensing assembly 1602 includes a mounting assembly that is rotatable and linearly translatable across the underlying reaction stations 1606. Mounting stations 1618 are provided on the mounting assembly for mounting of reagent dispensing cartridges and/or capsule pressing mechanisms.

Fluid dispensing system 1600 further includes bulk fluid dispensing assembly 1604. Bulk fluid dispensing assembly 1604 is used to dispense bulk fluids into bulk fluid reservoirs 1614 of reaction stations 1606 as discussed in reference to FIG. 11. In this aspect, bulk fluid dispensing assembly 1604 includes nozzle bracket 1608 for supporting nozzles 1610. Nozzles 1610 are connected to supply lines 1612. Each of supply lines 1612 are connected to a respective bulk container. As previously discussed in reference to FIG. 11, a single supply line 1612 from a desired bulk container may be used to fill bulk fluid reservoirs 1614. In this aspect, each of supply lines 1612 may be fluidly connected to a different bulk container. The number of nozzles 1610 and associated supply lines 1612 may vary depending upon the number of different bulk fluids desired. Representatively, in one embodiment, six nozzles 1610 and six supply lines 1612 extending from six different bulk containers may be connected to nozzle bracket 1608.

Nozzle bracket 1608 may be linearly translatable across the underlying reaction stations 1606. In this aspect, nozzle bracket 1608 may be movably connected by support arms 1620 to bracket rail 1616. Bracket rail 1616 may extend along a back end of reaction stations 1606. Nozzle bracket 1608 extends from bracket rail 1616 over reaction stations 1606. Nozzle bracket 1608 and the associated supply lines 1612 and nozzles 1610 may be moved along bracket rail 1616 by another x axis and positioned over the desired bulk fluid reservoir 1614. Once nozzle bracket 1608 is positioned over the desired bulk fluid reservoir 1614, one of nozzles 1610 associated with the desired bulk fluid may be actuated to dispense the desired bulk fluid into bulk fluid reservoir 1614. Bulk fluid dispensing assembly 1604 moves independently from fluid dispensing assembly 1602. In this aspect, during operation, bulk fluid dispensing assembly 1604 may be one or more stations ahead of fluid dispensing assembly 1602.

Fluid dispensing system 1600 may further include reagent cartridge scanner 1622 attached to nozzle bracket 1608. Reagent cartridge scanner 1622 may be any type of scanner suitable for reading identifiers such as radio frequency identification (RFID) tags, shape identifiers, color identifiers, numbers or words, other optical codes, barcodes etc. associated with reagent cartridges positioned on reaction stations 1606 (e.g. identifier 920 illustrated in FIG. 9A). In this aspect, reagent cartridge scanner 1622 includes a reading window at end 1624. When reagent cartridge 1634 is positioned on one of mounting bases 1632, an identifier positioned along an end of reagent cartridge 1634 is aligned with the reading window at end 1624. The identifier may be read by reagent cartridge scanner 1622 through the reading window. Reagent cartridge scanner 1622 moves horizontally along bracket rail 1616 from one reaction station 1606 to the next reading an identifier associated with a reagent cartridge mounted at each reaction station 1606. Although reagent cartridge scanner 1622 is shown mounted to nozzle bracket 1608, it is further contemplated that reagent cartridge scanner 1622 and nozzle bracket 1608 may be mounted to different bracket assemblies such that they are independently movable.

Figure 18:
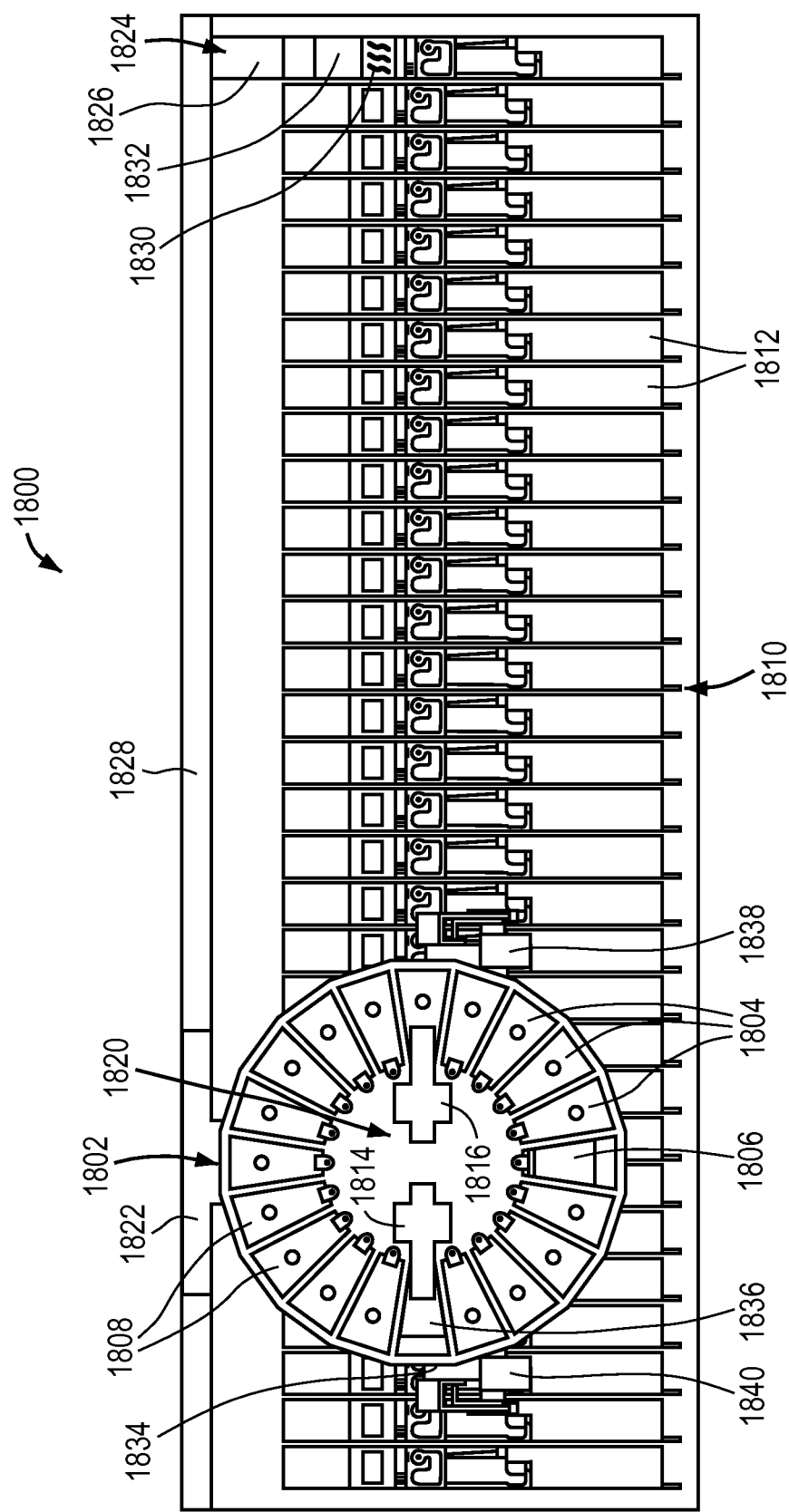
FIG. 18 illustrates a top view of an embodiment of a fluid dispensing system.

In addition to reagent cartridge scanner 1622, fluid dispensing system 1600 may include slide scanner 1628. Although only one slide scanner 1628 is illustrated in FIG. 16A, it is to be understood that fluid dispensing system 1600 includes a second slide scanner as illustrated in FIG. 18 that is substantially the same as slide scanner 1628. Slide scanner 1628 may be any type of scanner suitable for reading identifiers such as radio frequency identification (RFID) tags, shape identifiers, color identifiers, numbers or words, other optical codes, barcodes etc. associated with slide 1638 positioned on reaction station 1606. Slide scanner 1628 may be attached to fluid dispensing assembly 1602 positioned above reaction station 1606 by scanner bracket 1630. Scanner bracket 1630 may be attached to a non-rotatable support member of fluid dispensing assembly 1602 such that it moves linearly along with fluid dispensing assembly 1602 but does not rotate. In this aspect, slide scanner 1628 can be moved from one reaction station 1606 to the next along with fluid dispensing assembly 1602. Alternatively, slide scanner 1628 may be linearly and rotatably translatable along with fluid dispensing assembly 1602. In still further embodiments, scanner bracket 1630 of slide scanner 1628 may be directly attached to rail 1616 such that it may be moved independently from fluid dispensing assembly 1602.

Mirror 1626 may be positioned within each reaction station 1606 to facilitate reading of identifier 1640 associated with slide 1638 (see FIG. 16B) positioned within reaction station 1606. As illustrated in FIG. 16B, identifier 1640 is located at an end of slide 1638, preferably on a frosted region of slide 1638. Slide 1638 is positioned within reaction chamber 1646 of reaction station 1606 so that the sample mounted on slide 1638 and identifier 1640 are face down. Mirror 1626 is positioned below the end of slide 1638 including identifier 1640 such that image 1642 of identifier 1640 is reflected in mirror 1626. Mirror 1626 is positioned so that image 1642 is reflected in a direction of slide scanner 1628 as illustrated by arrow 1644. Slide scanner 1628 reads identifier 1640 by scanning image 1642 of identifier 1640 from mirror 1626. In some embodiments, mirror 1626 may be a disposable mirror that can be removed and replaced with a new mirror by a user. As such, if mirror 1626 becomes scratched or otherwise unsuitable for use, the user can immediately replace it without the need to call for service. Alternatively, mirror 1626 may be fixedly mounted within reaction station 1606. As will be discussed in more detail in reference to FIGS. 22-24, information obtained by reagent cartridge scanner 1622 from the identifier on the reagent cartridge and by slide scanner 1628 from identifier 1640 on slide 1638 may be used to verify a processing protocol performed on the sample mounted on slide 1638.

Figure 17:
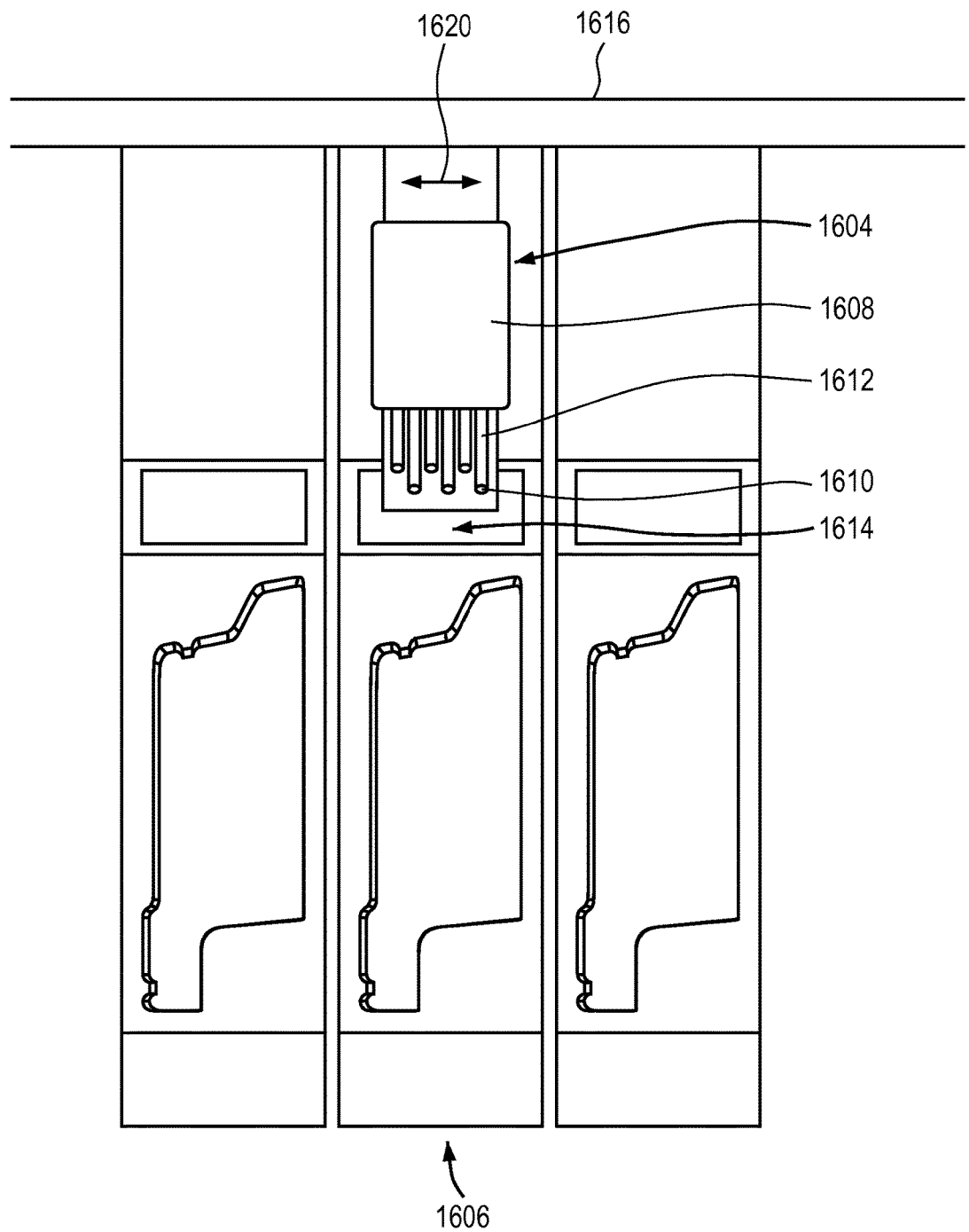
FIG. 17 illustrates a top view of an embodiment of a bulk fluid dispensing assembly.

FIG. 17 illustrates a top view of an embodiment of bulk fluid dispensing assembly. Bulk fluid dispensing assembly 1604 is substantially the same as the bulk fluid dispensing assembly described in reference to FIG. 16A. From this view, the positioning of nozzles 1610 over bulk fluid reservoir 1614 of reaction station 1606 can be seen. It is noted that reagent cartridge scanner 1622 and reagent cartridge mounting member 1632 are omitted so that the relationship between nozzles 1610 and bulk fluid reservoir 1614 can be more clearly seen. Once positioned as illustrated, a desired fluid from the bulk reagent container may be pumped through supply line 1612 and out nozzle 1610 to the desired reservoir 1614. Once the desired amount of fluid is pumped into reservoir 1614, bulk fluid dispensing assembly 1604 may be moved in a direction of arrow 1620 to the next reaction station for dispensing of a same or different reagent into the reservoir.

FIG. 18 illustrates a top view of an embodiment of a fluid dispensing system. The geometry and mechanism of fluid dispensing system 1800 is variable depending on the operation of the fluid dispensing assembly selected for use with system 1800. System 1800 includes mounting assembly 1802 having a plurality of mounting stations 1804 at which fluid dispensing cartridge 1806 may be mounted. Mounting assembly 1802 may be substantially the same as mounting assembly 1506 described in reference to FIG. 15. Fluid dispensing cartridge 1806 may be substantially the same as fluid dispensing cartridge 1502 described in reference to, for example, FIG. 15.

Mounting stations 1804 preferably include mounting apertures 1808 for selectively positioning a plurality of fluid dispensing cartridges 1806. In one embodiment, one or more of mounting stations 1804 may include mounting aperture 1834 dimensioned for positioning of capsule pressing mechanism 1836. A cartridge pump assembly such as cartridge pump assembly 1510 previously discussed in reference to FIG. 15 is mounted to each of stations 1804 holding fluid dispensing cartridges 1806. Actuators 1814 and 1816 of actuator assembly 1820 may be aligned with the pump assembly of cartridges 1806 to activate the pump assembly when desired. In addition, one of actuators 1814 or 1816 may be aligned with capsule pressing mechanism 1836. Since there are two actuators 1814 and 1816, reagent from two different fluid dispensing cartridges 1806 can be dispensed at the same time at different locations. Alternatively, one of actuators 1814 and 1816 may be aligned with a fluid dispensing cartridge 1806 while the other is aligned with capsule pressing mechanism 1836 to facilitate delivery of the reagent from both cartridge 1806 and a capsule mounted on one of reaction stations 1812. In still further embodiments, two capsule pressing mechanisms 1836 may be mounted to mounting assembly 1802 and actuators 1814 and 1816 aligned with each capsule pressing mechanism 1836.

System 1800 further includes bulk fluid dispensing assembly 1824. Bulk fluid dispensing assembly 1824 may be substantially the same as bulk fluid dispensing assembly 1604 described in reference to FIG. 16A. In this aspect, bulk fluid dispensing assembly 1824 includes nozzle bracket 1826 having nozzles 1830 and reagent cartridge scanner 1832 positioned thereon. Nozzle bracket 1826 slides along bracket rail 1828 as previously discussed in reference to FIG. 16A.

Fluid dispensing system 1800 also includes receiving assembly 1810 having a plurality of reaction stations 1812. Reaction stations 1812 may be similar to the reaction stations previously discussed. Generally speaking, receiving assembly 1810 is positioned beneath mounting assembly 1802 and bulk fluid dispenser 1824 taking advantage of gravity to deliver fluids dispensed from fluid dispensing cartridges 1806 and bulk fluid dispenser 1824. Preferably, mounting assembly 1802, bulk fluid dispenser 1824 and receiving assembly 1810 are movable with respect to one another so that the plurality of cartridges 1806 and bulk fluid dispenser 1824 can be positioned to dispense fluids onto any of the desired reaction stations 1812. Any combination of movability of mounting assembly 1802, bulk fluid dispenser 1824 and reaction stations 1812 may be selected. For example, each of mounting assembly 1802 and bulk fluid dispenser 1824 may be movable while reaction stations 1812 are stationary. Alternatively, reaction stations 1812 may be movable and mounting assembly 1802 and bulk fluid dispenser 1824 stationary. In addition, as previously discussed, mounting assembly 1802 may be a carousel that is rotatable about a central axis so as to align cartridges 1806 with the desired reaction station 1812. Mounting assembly 1802 may also be linearly translatable such that it may move from one reaction station 1812 to the next. Bulk fluid dispenser 1824 may further be linearly translatable such that it may move from one reaction station 1812 to the next ahead or behind mounting assembly 1802. Reaction stations 1812 may all be the same type of items, such as slides or alternatively may include different types of items such as slides and containers.

In one example of operation of dispensing system 1800, mounting assembly 1802 is rotated so that individual cartridges 1806 or capsule pressing mechanism 1836 are selectively positioned adjacent one or both of actuator assembly 1820. In some embodiments, system 1800 may include a plurality of actuator assemblies 1820 which are positioned adjacent to each cartridge 1806 and capsule pressing mechanism 1836 such that rotation of mounting assembly 1802 to align each cartridge 1806 and capsule pressing mechanism 1836 with actuator assembly 1820 is not required.

Actuator assembly 1820 can be any activation device that triggers cartridge 1806 to emit a controlled amount of fluid. Representatively, actuator assembly 1820 may include a piston mechanism that aligns with, for example, an actuator of the cartridge pump assembly or capsule pressing mechanism.

Mounting assembly 1802 may be both translated and rotated with respect to receiving assembly 1810 so that an individual cartridge 1806 can be selectively positioned above any reaction station 1812. Once cartridge 1806 is positioned above one of receiving members 1812, actuator assembly 1820 triggers cartridge 1806 to emit a controlled amount of fluid onto reaction station 1812.

As seen in FIG. 18, in one embodiment, mounting assembly 1802 is rotatably attached to support member 1822 while actuator assembly 1820 is fixedly attached to support member 1822 such that cartridges 1806 and capsule pressing mechanism 1836 can be rotated with respect to actuator assembly 1820. Actuator assembly 1820 is fixedly attached to support member 1822, optionally beneath mounting assembly 1802. Preferably, support member 1822 can be translated horizontally such that the cartridges 1806 and capsule pressing mechanism 1836 can be both rotated and translated with respect to the receiving members 1812. In this manner, a chosen cartridge 1806 can be selectively positioned above any reaction station 1812. Similarly, a chosen capsule pressing mechanism 1836 can be positioned above a desired reaction station 1812.

Slide scanners 1838, 1840 may also be attached to support member 1822 such that they may be moved from one reaction station 1812 to the next along with mounting assembly 1802. In one embodiment, slide scanners 1838, 1840 may be positioned along opposite sides of mounting assembly 1802. In still further embodiments, slide scanners 1838 may be positioned within dispensing system 1800 in any matter suitable for reading identifiers on slides positioned within dispensing system 1800.

Although reaction stations 1812 are shown linearly positioned within receiving assembly 1810, it is further contemplated that reaction stations 1812 may be divided into two or more rows. In this aspect, actuator assembly 1820 may optionally include two or more actuators, for example, two actuators 1814, 1816 used to dispense fluid onto two rows of receiving members. In operation, actuator 1814 is adapted to dispense fluids onto reaction stations 1812 in one row and actuator 1816 is adapted to dispense fluids onto reaction stations 1812 in another row. It is further contemplated that any number of actuators and/or receiving members can be employed.

Figure 19:
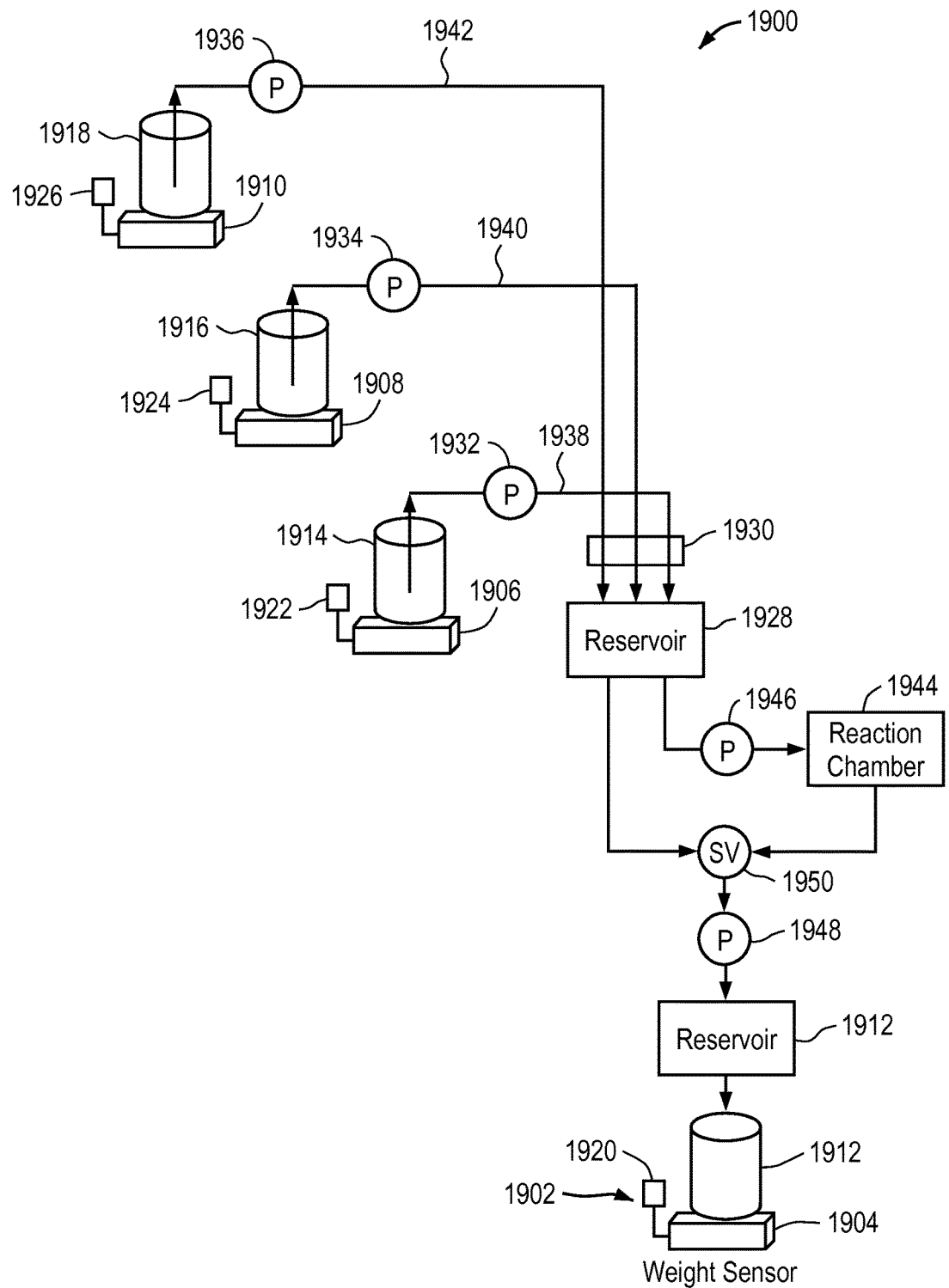
FIG. 19 illustrates a schematic diagram of an embodiment of a sample processing system including a bulk reagent sensing assembly.

FIG. 19 illustrates a schematic diagram of a sample processing system including a bulk reagent sensing assembly. During sample processing, there may be several reagents that are required in large quantities. For example, processing may require reagents to rinse antibodies or detection reagents such as distilled water and buffer solutions. Such reagents are stored in bulk containers within the system. In addition, reagent waste is disposed into bulk containers. It is often difficult for a user to determine the amount of reagent remaining within each of the bulk containers or whether a bulk waste container is full. This can result in the user failing to replace (or refill) a bulk container. System operation may in turn be delayed because the desired reagent is not available or a waste container is too full to accept more waste.

In this aspect, sample processing system 1900 may include bulk reagent sensing assembly 1902. Bulk reagent sensing assembly 1902 may include sensors 1904, 1906, 1908 and 1910 for detecting the amount of liquid (e.g. reagent) within bulk containers 1912, 1914, 1916 and 1918, respectively. In some embodiments, sensors 1904, 1906, 1908 and 1910 may be sensors which are capable of measuring a weight of bulk containers 1912, 1914, 1916 and 1918 positioned thereon. Representatively, one or more of sensors 1904, 1906, 1908 and 1910 may be a load cell weight sensor that converts a force applied to the sensor by the weight of the container into an electrical signal such as that available from Minebea Co., Ltd of Miyota-machi, Kitasaku-gun, Nagano, Japan.

A weight and volume of each of bulk containers 1912, 1914, 1916 and 1918 may be known. In addition, the type of liquid within bulk containers 1912, 1914, 1916 and 1918 and the density of the liquid may also be known. To determine a volume of the liquid within, for example, bulk container 1912, the weight of bulk container 1912 (in the absence of liquid) may be subtracted from the weight measured by sensor 1904 (mass of bulk container and liquid). The weight of the liquid within container 1912 and the density of the liquid may then be used to calculate the volume of fluid within container 1912. A determination of how full or empty the container is may then be determined by subtracting the volume of liquid in container 1912 from the known container volume. Although measuring of a liquid within bulk container 1912 is described herein, a similar calculation may be performed using bulk containers 1914, 1916 and 1918 and sensors 1906, 1908 and 1910, respectively, to measure a volume of liquid within bulk containers 1914, 1916 and 1918. In addition, although four weight sensors 1904, 1906, 1908 and 1910 are illustrated in FIG. 19, it is contemplated that the number of sensors may vary depending upon the number of desired bulk containers in the system.

In still further embodiments, system 1900 may include light source 1920, 1922, 1924 and 1926 to facilitate visual inspection of a liquid level inside of containers 1912, 1914, 1916 and 1918, respectively. One or more of light source 1920, 1922, 1924 and 1926 may be a light-emitting diode (LED) positioned next to a respective container. Alternatively, one or more of light source 1920, 1922, 1924 and 1926 may be any light source capable of illuminating containers 1912, 1914, 1916 and 1918 so that that a liquid level therein can be visualized. It is further contemplated that a material of containers 1912, 1914, 1916 and 1918 may be selected to facilitate visual inspection of a liquid within the container. Representatively, containers 1912, 1914, 1916 and 1918 may be made of a semi-transparent or transparent material.

Operation of processing system 1900 and bulk reagent sensing assembly 1902 will now be described. According to one embodiment, bulk container 1912 may be a waste container and each of bulk containers 1914, 1916 and 1918 may hold a reagent. A reagent from one or more of bulk containers 1914, 1916 and 1918 may be dispensed into reservoir 1928 of a desired reaction station by bulk reagent dispenser 1930. Pumps 1932, 1934, 1936 may be associated with each supply line 1938, 1940, 1942, respectively, of bulk reagent dispenser 1930 to pump the reagent from the respective bulk container. Once a desired reagent is within reservoir 1928, the reagent may be pumped to reaction chamber 1944 with the aid of pump 1946. After processing with the reagent in reaction chamber 1944 is completed, the reagent may be pumped from reaction chamber 1944 to waste bulk container 1912 with the aid of pump 1948 through solenoid valve 1950. In addition, once the reagent within reservoir 1928 is no longer needed, it may be drained into bulk container 1912 with the aid of pump 1948 by switching the line of solenoid valve 1950.

Sensor 1904 may continuously or periodically calculate a volume of waste within bulk container 1912. When the volume of liquid within bulk container 1912 is above a predetermined level (e.g. the container is full), the system alerts the user. Similarly, sensors 1906, 1908, 1910 may continuously or periodically calculate a volume of liquid within bulk containers 1914, 1916, 1918, respectively. When the volume of liquid is below a predetermined level (e.g. the container is empty), the system alerts the user. Upon receiving the alert, the user may refill, replace or empty the bulk container. In addition, the system may automatically switch from an empty reagent container to one that has a sufficient amount of the desired liquid. The system may also automatically switch from a waste bulk container that is full to one that is empty. In this aspect, where the user is not able to immediately attend to the bulk containers, processing may continue uninterrupted.

Figure 20:
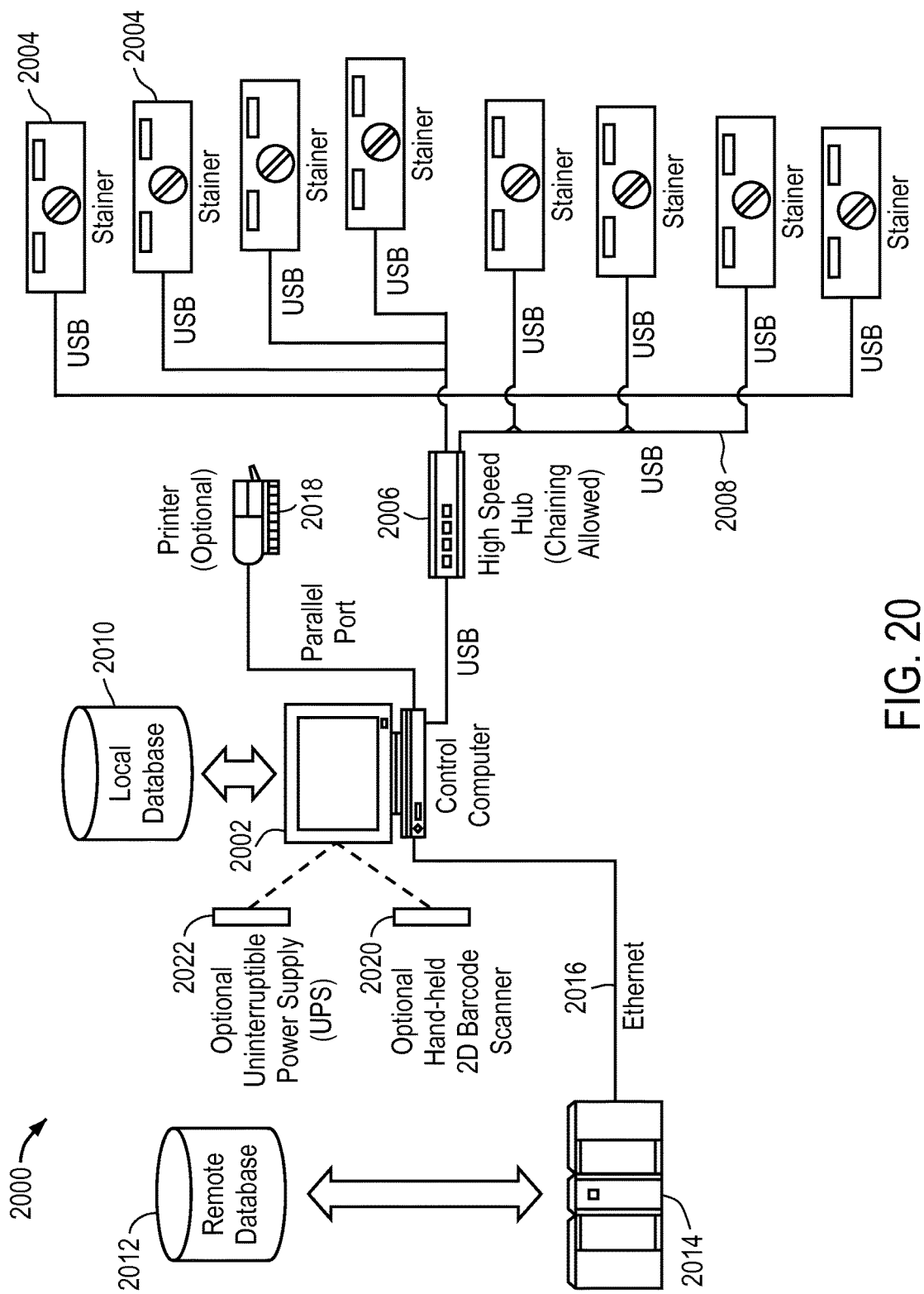
FIG. 20 is an illustration of an embodiment of an automated sample processing system.

FIG. 20 is an illustration of one embodiment of an automated sample processing system. Automated sample processing system 2000 includes a control computer 2002 in communication with a plurality of stainers 2004 and may provide a centralized user interface for controlling the plurality of stainers 2004. Stainers 2004 may be used to process biological specimens as previously discussed. Control computer 2002 may communicate with stainers 2004 in any manner known in the art, for example control computer 2002 may communicate with stainers 2004 via a high-speed hub 2006. High-speed hub 2006 enables system 2000 to quickly convey information between the plurality of stainers 2004 and the other components such as control computer 2002. For example, stainers 2004 may download staining protocols to be applied to slides placed in the reaction stations on stainers 2004 over a network formed by data lines 2008 and high-speed hub 2006. It shall be appreciated that control computer 2002 and stainers 2004 may be configured to communicate through hardwires or wirelessly, for example, the system may utilize data lines 2008, as described above, which may be conventional conductors or fiber optics. Additionally, the components may communicate wirelessly using radio frequency communication, such as BLUETOOTH® (a registered trademark of Bluetooth SIG, Inc., of Bellevue, Wash.), or any other wireless technology.

Control computer 2002 may also communicate with one or more local databases 2010 so that data may be transferred to or from local databases 2010. For example, local database 2010 may store a plurality of staining protocols that are designed to be performed by reaction stations on stainers 2004. The staining protocols may include a series of staining operations that are to be performed on slides positioned within the reaction stations. The staining protocols implemented by reaction stations on stainers 2004 may be chosen based on information obtained from identifiers (e.g., barcodes, radio frequency identification devices (RFID), etc.) associated with the system components (e.g., on microscope slides, reagent cartridges, fluid dispensing cartridges, reagent containers, etc.). Control computer 2002 may process identification data received from the reaction stations on stainers 2004 and retrieve staining protocols from local database 2010 and transmit the staining protocols to the reaction stations on stainers 2004. Furthermore, control computer 2002 may use local databases 2010 for storage of information received from reaction stations on stainers 2004, such as reports and/or status information.

Control computer 2002 may also communicate with one or more remote databases 2012 and/or a server 2014. Control computer 2002 may communicate with remote database 2012 directly or through server 2014, which may be a laboratory information system (LIS). Control computer 2002 may communicate with server 2014 via a network 2016. As noted above, server 2014 may communicate with remote database 2012. Server 2014 and remote database 2012 may be used to provide staining protocols to be used by the reaction stations on stainers 2004 in a similar fashion as local database 2010 or to supplement the protocols provided by local database 2010.

Automated processing system 2000 may optionally include one or more printers 2018. Printer 2018 may communicate directly with control computer 2002, as shown, or directly with stainers 2004. Furthermore, stainers 2004 may each have a dedicated printer 2018 that may be integrated into the stainer or free-standing, or multiple stainers 2004 may share one or more printers.

Automated reagent dispensing system 2000 may also include a hand-held or desktop scanner 2020 for reading identifiers that may be included throughout the system components (e.g., on microscope slides, reagent cartridges, fluid dispensing cartridges, reagent containers, etc.). Any type of scanner 2020 may be utilized that is capable of interpreting the identifiers. For example, scanner 2020 may be an RFID scanner, a 1D or 2D barcode scanner, or any other type of scanner known in the art. Scanner 2020 may communicate directly with control computer 2002 or stainers 2004 and each component may have a dedicated scanner.

The system may also be powered by an uninterruptible power supply 2022. Uninterruptible power supply 2022 may be used to limit the susceptibility of the system to general power failures that may invalidate tests that are interrupted. Such an interruption in power could also result in the tissue samples becoming unusable which could require gathering additional specimens. Power supply 2022 may be used to power any or all of the components of automated processing system 2000.

Although control computer 2002 is shown networked with multiple stainers 2004 in FIG. 20, it shall be appreciated that the stainers 2004 may be combined in a single unit with an onboard control computer, in addition to any other component described above in the automated reagent dispensing system. Such a combination may provide a compact, stand-alone unit that may be used to process lower volumes of biological specimens.

As previously discussed, one or more processing protocols may be downloaded to stainers 2004. Reaction stations on stainers 2004 may then implement the processing protocol on slides placed in the reaction stations on stainers 2004 independent of control computer 2002. In this aspect, if control computer 2002 stops (e.g. crashes or freezes), the processing protocol being run on a slide within reaction stations on stainers 2004 may continue uninterrupted.

In addition, a processing protocol performed at the reaction stations on stainers 2004 may be monitored by control computer 2002. For example, once a staining operation designated by the processing protocol is completed at a reaction station on one or more of stainers 2004, a staining status report may be sent to control computer 2002 notifying control computer 2002 that the staining operation has been completed. In some embodiments, a report is sent to control computer 2002 at regular intervals (e.g. every 2-3 seconds). All staining operations completed between intervals may be reported to control computer 2002. In this aspect, a staining operation that takes more than 3 seconds, for example 5 seconds, will not be reported to control computer 2002 in the report sent while the operation is still pending (i.e., the report sent 2-3 seconds into the 5 second operation). Instead, performance of the staining operation will be reported to control computer 2002 with the subsequent report issued after the staining operation has been completed. Alternatively, a staining operation may be reported at any time prior to completion. In addition, if stainer 2004 is unable to send the staining status report at the regular interval (e.g., control computer 2002 loses power), the reports that were not sent will be compiled at stainer 2004 and sent together to control computer 2002 when reporting is resumed (e.g., power is restored).

A staining log of each of the operations performed on strainers 2004 may be created by control computer 2002 based on the status report and displayed on control computer 2002. In this aspect, control computer 2002 can display all necessary staining logs to the user when desired. In some embodiments, in addition to the staining operations completed on strainers 2004, the staining log may include, for example, identification information relating to the system components (e.g., microscope slides, reagent cartridge, fluid dispensing cartridges, bulk reagent containers, etc.). Representatively, the staining log may include information relating to the fluid dispensing cartridges or bulk reagent containers such as a listing of the reagents within the system that may be used during operation of strainers 2004. Information relating to the reagent cartridges may include, for example, the identity of an antibody (e.g. a primary antibody) within the reagent cartridge attached to a reaction chamber. Information relating to the slides may include, for example, a patient identification number or information relating to an agent such as an antibody that is to be applied to the slide.

Figure 21:
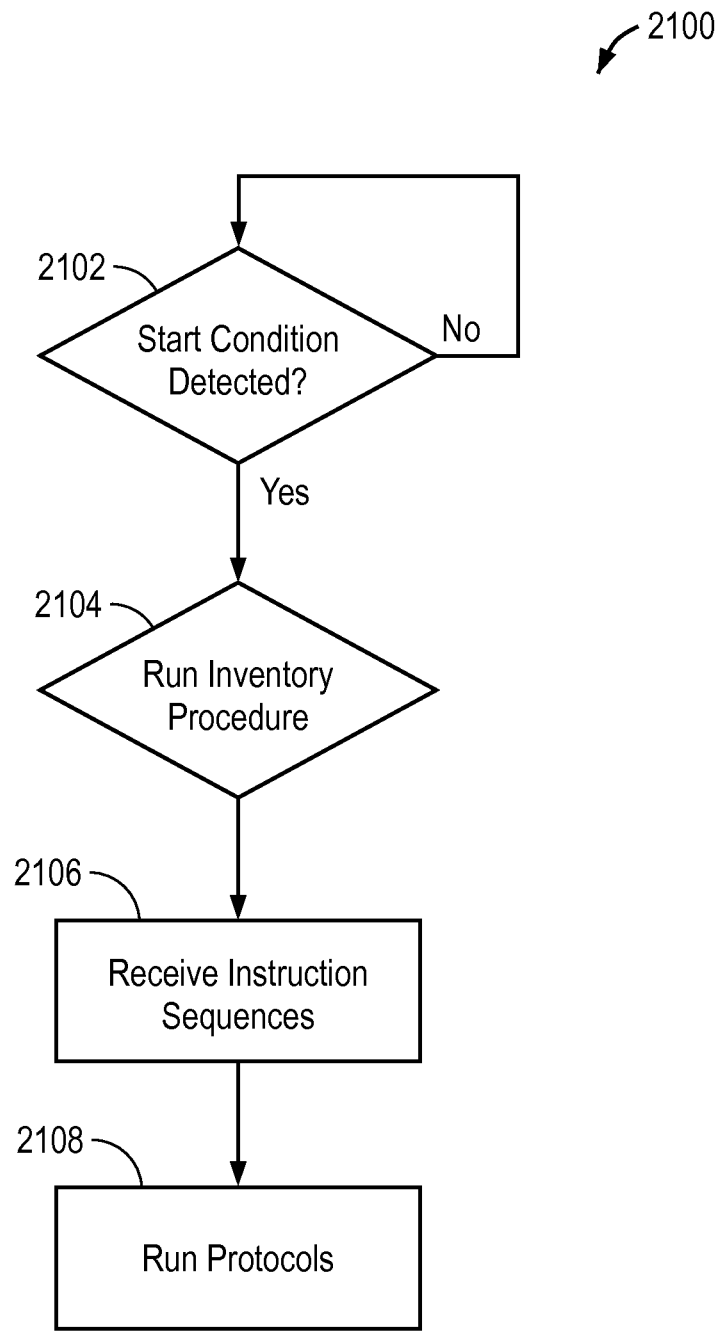
FIG. 21 illustrates a flow chart of an embodiment of a sample processing procedure.

FIG. 21 illustrates a flow chart of one embodiment of a sample processing procedure. Sample processing is initiated once a start condition is detected. Sample processing procedure 2100 may include an initialization procedure that occurs once a start condition is detected (block 2102). A start condition may be, for example, closing the cover on the housing of a stainer included in the automated reagent dispensing system, receiving a start signal from a control computer, or any other condition. If a start condition is not detected, the automated reagent dispensing system may continually check whether a start condition is detected until a start condition is detected.

The initialization procedure occurs after a start condition is detected and may include taking an inventory of system components, for example, the reaction stations, reaction chambers, reagent cartridges, fluid dispensing cartridges and/or bulk reagent containers (block 2104). Inventory of the fluid dispensing cartridges, reagent cartridges and bulk containers may be taken by scanning identifiers located on the reaction stations, cartridges and containers within the system. Representatively, scanning may be performed by reagent cartridge scanner 1608 and/or slide scanner 1628 located on the linearly translatable mounting assembly as illustrated in FIG. 16A. In the case of slide scanner 1628, slide scanner 1628 may move with mounting assembly along the reaction stations and scan identifiers located on the slides associated therewith. This enables the system to determine which reaction stations include specimens and may further allow the system to identify the proper agent (e.g., primary antibody) to be applied to the slide. After scanning the identifiers, the mounting assembly returns to a home position. In addition, by scanning the reagent cartridges using, for example reagent cartridge scanner 1608, the system may identify the type and quantity of a reagent present in each reagent cartridge. A determination as to the proper processing protocol to apply to the slide may be made using this information.

In addition, assessing the fluid volume level of, for example the bulk containers, obtained from the sensors may be part of the inventory procedure. Maintaining a history of the quantity of a liquid that has been dispensed from the bulk containers may further assist in making the determination regarding the fluid volume level within the containers. After determining the fluid volume level, a signal may be output to provide the user with an indication regarding how much and what types of fluids are stored in the containers. Where the system determines that a container is empty or contains an insufficient amount of fluid to perform a predetermined staining process, the system may initiate a replacement signal indicating that one or more containers have an insufficient amount of fluid and need to be replaced or refilled. The system may further automatically select a different container which contains a sufficient volume of the desired fluid, if available, so that processing may continue uninterrupted.

Once the inventory procedure is completed, instruction sequences are received by the reaction stations (block 2106) and the staining protocols downloaded to each reaction station are run (block 2108). A staining protocol may include a sequence of processing operations including, in any order and at various times, dispensing a primary reagent from a reagent cartridge associated with a reaction station, dispensing a secondary reagent from a fluid dispensing cartridge mounted in the overhead mounting assembly, dispensing a further reagent from a bulk fluid dispensing assembly positioned above the reaction station and/or dispensing a reagent into the reaction station through inlet ports within the reaction station.

Figure 22:
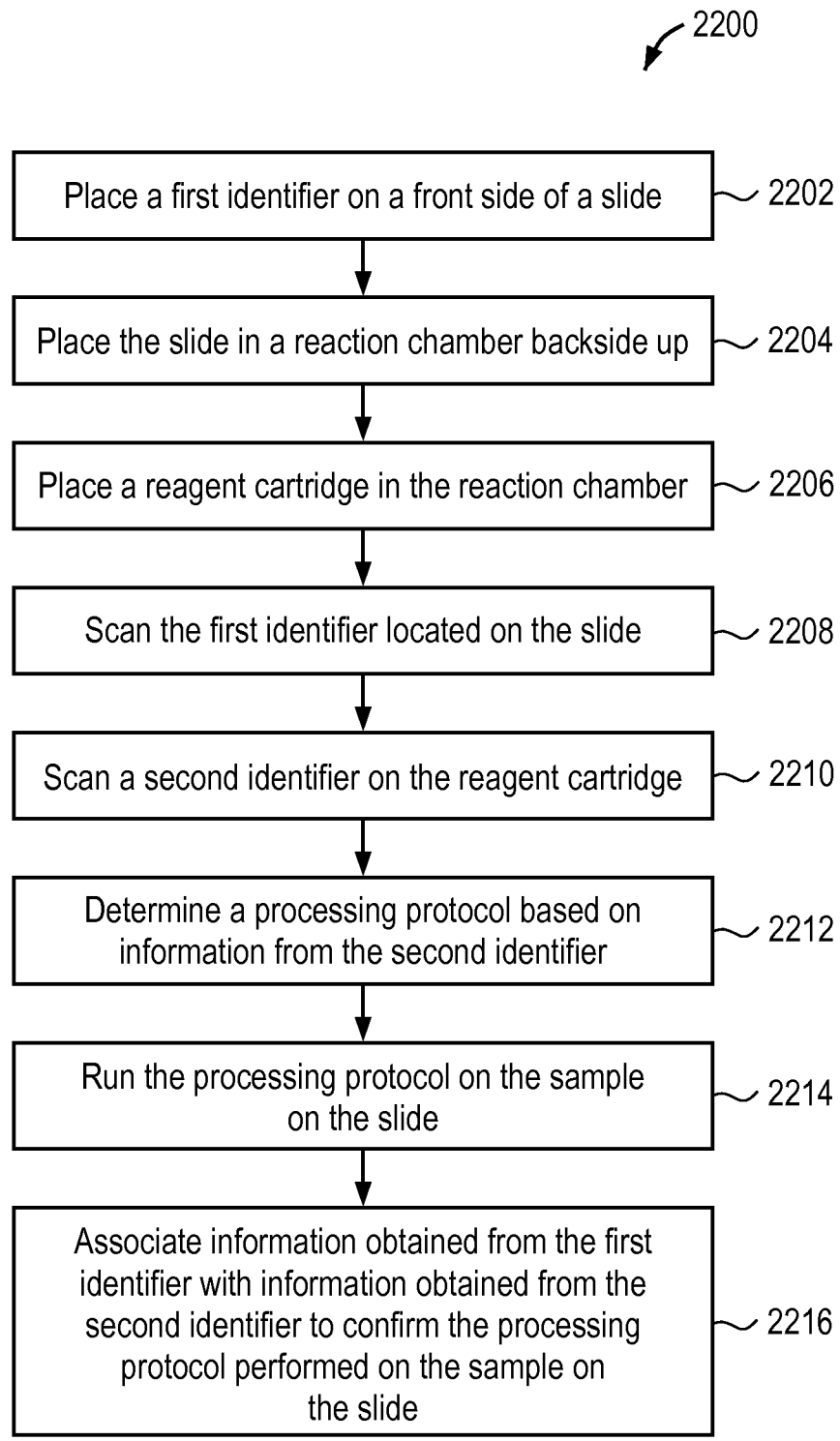
FIG. 22 illustrates a flow chart of an embodiment of a sample processing procedure.

FIG. 22 illustrates a flow chart of an embodiment of a sample processing procedure. Typically, an operator, such as a lab technician, is entrusted with the responsibility of ensuring that a slide having a sample mounted thereon has been placed within the correct reaction station and processed according to a processing protocol assigned to that station. If, however, the operator mistakenly places the slide in the wrong station, the wrong processing protocol may be performed on the sample on the slide. Such mistake may not be discovered until the slide has been removed from the station and analyzed by, for example, the pathologist days or in some cases weeks later. Since the slide is no longer in the station, it may be difficult to determine the processing protocol performed on the slide and in turn whether the slide should be processed again or whether processing must be performed on a new slide having a new sample. Such error, may therefore cause significant delays in result analysis and reporting. Still further, where the error in processing is not detectable by the pathologist upon review of the sample, the mistake may go unnoticed leading to an incorrect recommendation or diagnosis.

The sample processing procedure illustrated in FIG. 22 may be used to verify a processing protocol performed on a sample mounted on a slide. In this aspect, procedure 2200 may include placing a first identifier on a front side of a slide (i.e., side with sample mounted thereon)(block 2202). The first identifier may be, for example, an identifier such as identifier 1640 described in reference to FIG. 16B. The identifier may include information such as patient information and/or the name of an agent, for example, an antibody, to be applied to the slide. The slide is then placed back side up (i.e., side opposite the sample) in a reaction chamber mounted to a reaction station for processing (block 2204). Once the slide is in place, a reagent cartridge is mounted to the reaction chamber (block 2206). The reagent cartridge may be a reagent cartridge such as reagent cartridge 408 described in reference to FIG. 4A. The reagent cartridge may have a second identifier, such as identifier 920 described in reference to FIG. 9A, positioned thereon. The second identifier may identify, for example, an antibody associated with the reagent cartridge. The antibody, may be, for example, found within a capsule (see, reagent capsule 900 of FIG. 9A) attached to the reagent cartridge.

The first identifier located on the slide is scanned (block 2208) and the second identifier located on the reagent cartridge is scanned (block 2210). A processing protocol to be applied to the sample on the slide is determined based on information obtained from the second identifier (block 2212). Representatively, the second identifier may identify a reagent within the reagent cartridge. Alternatively, the processing protocol to be applied to the sample on the slide may be determined based on information from the first identifier. The control computer may then use this information to select a processing protocol that may be run using the identified reagent. It is further contemplated that an operator may select a protocol based on the identified reagent. The selected processing protocol may be performed on the sample found on the slide (block 2214). Information obtained from the first identifier located on the slide may be associated with information obtained from the second identifier located on the reagent cartridge to confirm the processing protocol performed on the sample on the slide (block 2216). The information from the first identifier and the second identifier may be associated during processing of the sample according to the processing protocol or upon completion of the processing. The associated information may be displayed on the control computer so that the operator may determine whether the correct processing protocol was assigned to the correct slide.

FIG. 23 illustrates an embodiment of a display associated with a sample processing procedure. Display 2300 illustrates the information obtained from the first identifier and the information obtained from the second identifier. In this aspect, display 2300 includes reagent cartridge identification table 2302 and slide identification table 2304. Reagent cartridge identification table 2302 includes station identification column 2306 and reagent identification column 2308. Station identification column 2306 identifies the reaction station that the reagent cartridge is located on. Reagent identification column 2308 identifies a reagent located in the reagent cartridge. Representatively, upon review of reagent identification table 2302 illustrated in FIG. 23 an operator will understand that a reagent cartridge having antibody LCA is located at stations 2, 16 and 17, a reagent cartridge holding antibody CD30 is located at stations 3 and 5, a reagent cartridge holding antibody Desmin is located at station 9, a reagent cartridge holding antibody Cytokeratin7 is located at station 10 and a reagent cartridge holding antibody Vimentin is located at station 12.

Similarly, slide identification table 2304 includes slide identification column 2312 and reagent identification column 2310. Upon review of slide identification table 2304 illustrated in FIG. 23, an operator will understand that antibody LCA is to be applied to a slide located at stations 2, 16 and 17, antibody CD30 is to be applied to a slide located at stations 3 and 5, antibody Desmin is to be applied to a slide located at station 9, antibody Cytokeratin7 is to be applied to a slide located at station 10 and antibody Vimentin is to be applied to a slide located at station 12.

Reagent identification table 2302 and slide identification table 2304 are juxtaposed so that rows having the same station number are aligned. As a result, the operator can easily review reagent identification table 2302 and slide identification table 2304 and determine whether the proper antibody was applied to the proper slide. For example, slide identification table 2304 provides that the slide located at station 2 should receive antibody LCA. Reagent identification table 2306 indicates that the antibody located at station 2 was LCA. Based on this information, the operator can confirm that a processing protocol using LCA was properly assigned to the slide at station 2.

Reagent identification table 2302 and slide identification table 2304 may be saved and associated with other run information to provide traceability information. In other words, reagent identification table 2302 shows which reagent was associated with a particular station and slide identification table 2304 shows which reagent was desired to be dispensed on the slide. Saving this information (e.g., data of the generated tables before processing) is an indication of the processing performed on a slide. A staining log, such as that previously disclosed in reference to FIG. 20, may include the traceability information.

Based on the information provided by display 2300, the operator can choose to reload the stations and start another run by clicking on start run button 2314. Alternatively, the operator can choose to re-scan the existing samples again by clicking on the re-scan button 2316. Finally, an operator may choose to cancel the run or display by clicking on cancel button 2318.

FIG. 24 illustrates an embodiment of a display associated with a sample processing procedure. Display 2400 illustrates an embodiment where there is a mismatch of reagent information. Display 2400 is substantially similar to display 2300 in that it includes reagent identification table 2402 having station identification column 2406 and reagent identification column 2408. In addition, display 2400 includes slide identification table 2404 having slide identification column 2412 and reagent identification column 2410. Display 2400 further includes start-run button 2414, re-scan button 2416 and cancel button 2418.

As can be seen from slide identification table 2404, the slide located at station 2 requires antibody CD30 and the slide located at station 3 requires antibody LCA. Reagent identification table 2402, however, indicates that the antibody located at station 2 was LCA and the antibody located at station 3 was CD30. Thus, the wrong antibody, and in turn processing protocol, was assigned to the slide at station 2 and the slide at station 3. Based on this information, the operator can replace the slide at station 2 with a slide requiring LCA and the slide at station 3 with a slide requiring CD30 and re-scan the slides. Alternatively, the operator may replace the reagent cartridges with reagent cartridges having the proper antibody. Still further, the operator may replace the identifier on the slide with an identifier that properly identifies the reagent applied to the slide sample. Other mismatch variations are further contemplated that may be displayed on display 2400, for example a slide may be placed at a station with no reagent cartridge such as station 1.

It is further contemplated that in some embodiments, control computer 2002 may automatically alert a user to a mismatch. Representatively, control computer 2002 may be programmed to detect mismatches between reagent identification table 2402 and slide identification table 2404. When a mismatch is detected, an alarm may sound to alert the user that the reagent identified by the identifier on the slide has not been applied to the slide.

A device, such as control computer 2002, for performing the operations herein may be specially constructed for the required purposes or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, Flash memory devices including universal serial bus (USB) storage devices (e.g., USB key devices) or any type of media suitable for storing electronic instructions, each of which may be coupled to a computer system bus.

Figure 25A:
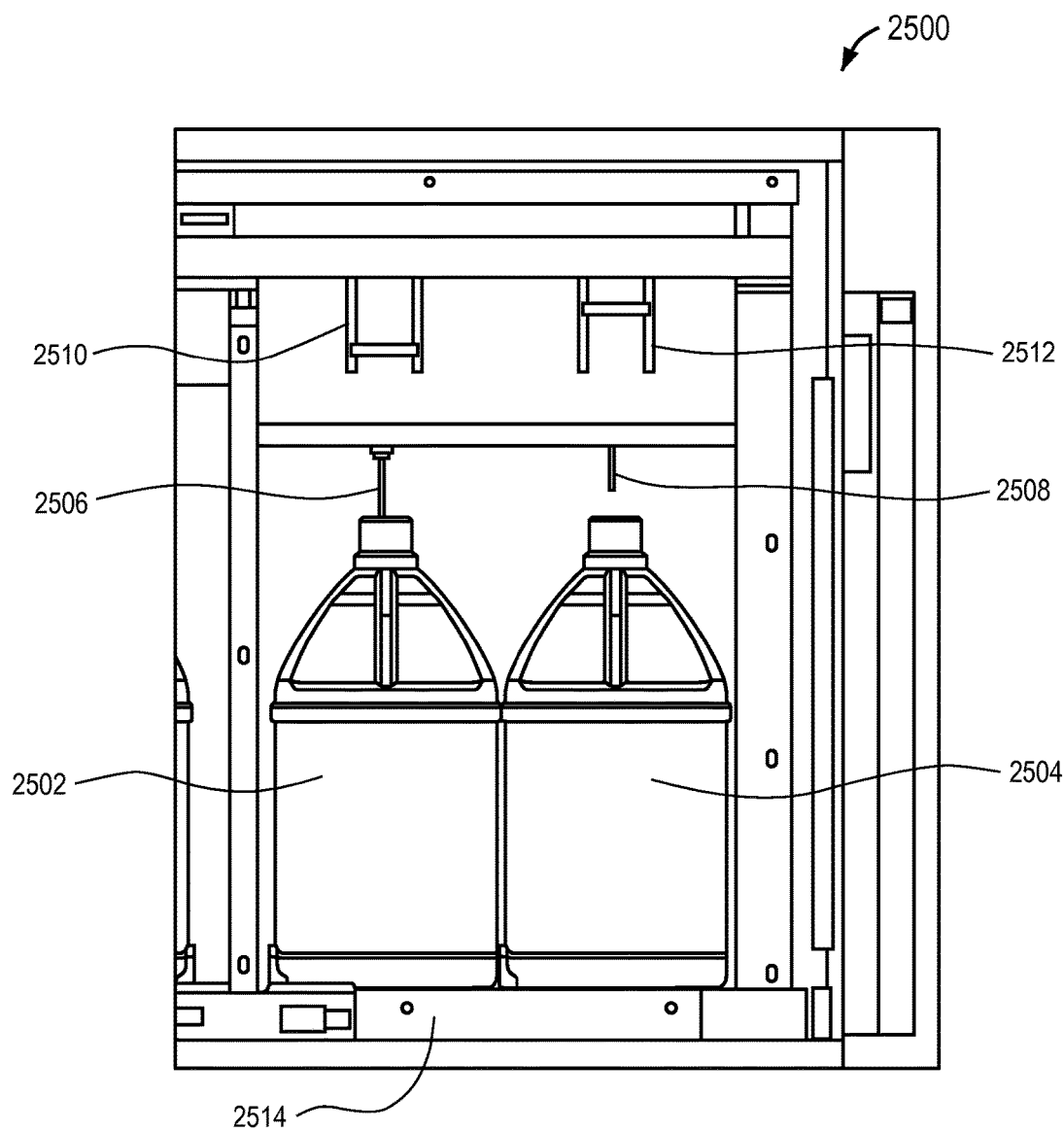
FIG. 25A illustrates a perspective view of an embodiment of a waste drain system of the sample processing system.
Figure 25B:
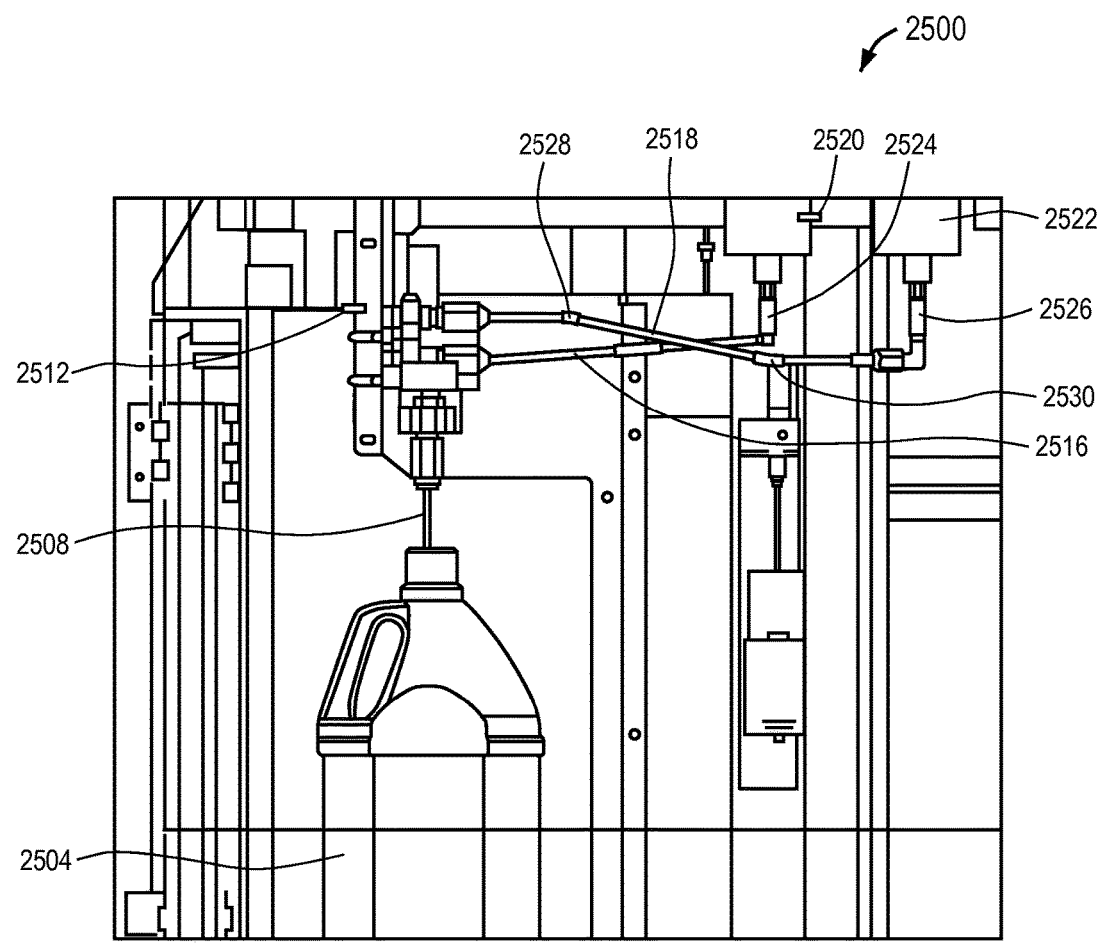
FIG. 25B illustrates a side view of the waste drain system of FIG. 25A.
Figure 25C:
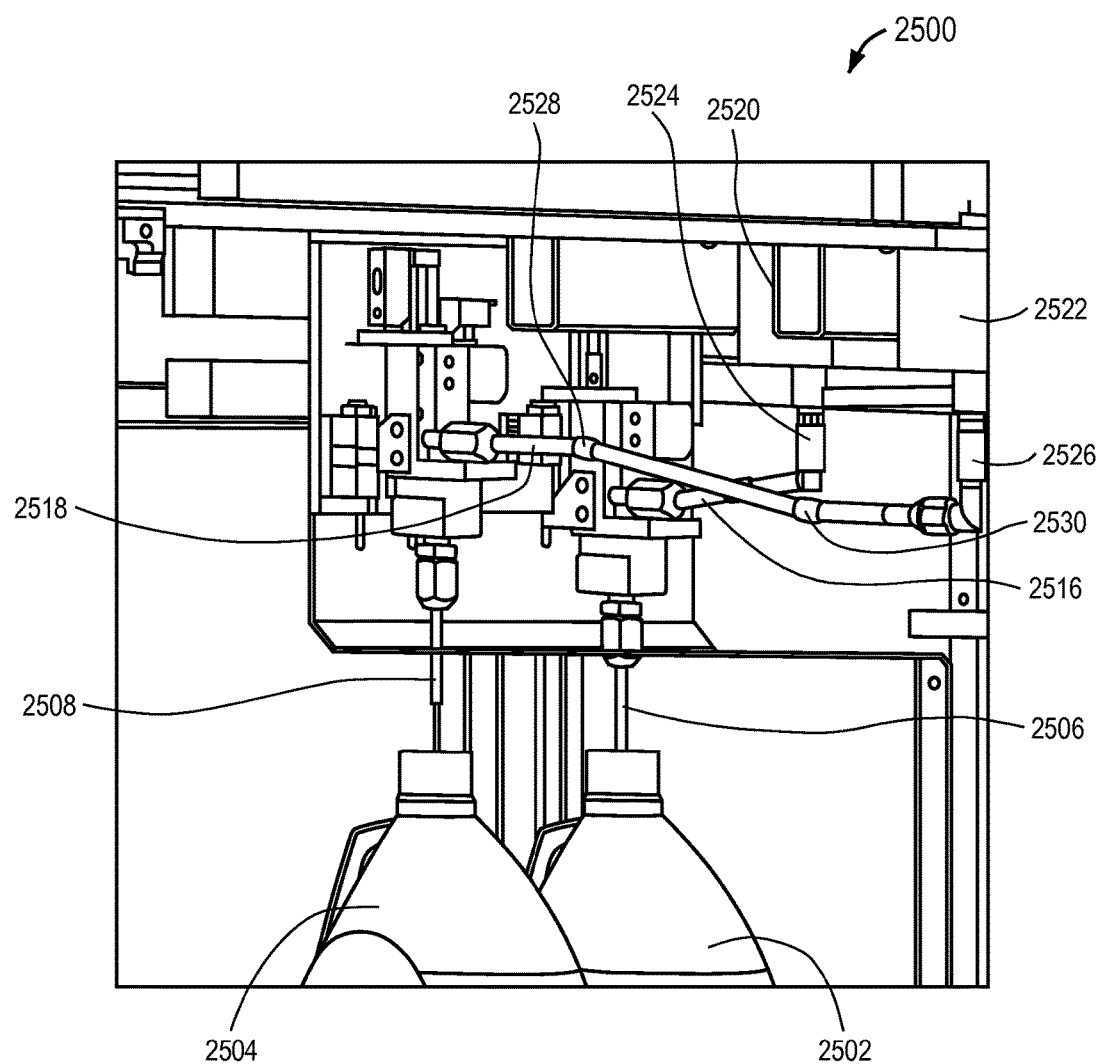
FIG. 25C illustrates a back side view of the waste drain system of FIG. 25A.

FIG. 25A, FIG. 25B and FIG. 25C illustrate perspective views of an embodiment of a waste drain system within the sample processing system. Waste drain system 2500 may include waste containers 2502, 2504. Waste containers 2502, 2504 may be similar to bulk containers 118 described in reference to FIG. 1. Although two waste containers 2502, 2504 are illustrated, the following description may apply to any number of waste containers positioned within the sample processing system. In addition, although the containers are described as waste containers, it is contemplated that the containers may be any type of bulk container used to hold any type of fluid (e.g. a reagent or wash fluid).

Waste containers 2502, 2504 may be positioned within the sample processing system below the reaction compartment holding the reaction stations as described in reference to FIG. 1. Waste containers 2502, 2504 may rest upon sensing plate 2514. Sensing plate 2514 may be similar to sensor 1904 described in reference to FIG. 19. In this aspect, sensing plate 2514 may be used to detect a fluid level within waste containers 2502, 2504. Drain tubes 2506, 2508 may be aligned with waste containers 2502, 2504, respectively, to help direct a waste fluid from the reaction stations into waste containers 2502, 2504. During operation, it may be desirable to raise or lower drain tubes 2506, 2508 depending on whether filling or removal of waste containers 2502, 2504 is desired. For example, during a processing operation it is desirable for drain tubes 2506, 2508 to be lowered within waste containers 2502, 2504 so that waste is deposited directly into containers 2502, 2504. Drain tubes 2506, 2508 are then raised to facilitate changing, replacing or emptying of waste containers 2502, 2504. In this aspect, levers 2510, 2512 are attached to drain tubes 2506, 2508, respectively, to raise or lower drain tubes 2506, 2508. FIG. 25A illustrates an embodiment where lever 2510 is lowered and drain tube 2506 is lowered into waste container 2502 while lever 2512 is raised and drain tube 2508 is raised above waste container 2504.

Drain tubes 2506, 2508 are fluidly connected to connecting tubes 2516, 2518, respectively, as illustrated in FIG. 25B. Connecting tubes 2516, 2518 provide a fluid conduit for waste to travel from the reaction stations to drain tubes 2506, 2508. Connecting tubes 2516, 2518 may have a modifiable configuration such that they provide a sloped-down conduit when drain tubes 2506, 2508 are lowered within waste containers 2502, 2504 and a sloped-up conduit when drain tubes 2506, 2508 are raised above waste containers 2502, 2504. Each of connecting tubes 2516, 2518 may be independent from one another and therefore independently modifiable. In this aspect, connecting tube 2518 may be a jointed tube having first joint 2528 proximal to drain tube 2508 and second joint 2530 distal to drain tube 2508. Connecting tube 2518 may be made of sections of a rigid material such as a metal or rigid plastic material or a more flexible material such as a flexible plastic connected by joints 2528, 2530. Alternatively, connecting tube 2518 may be an integrally formed tube made of a flexible plastic material that is modifiable in the absence of joints and therefore joints 2528 and 2530 may be omitted. When drain tube 2508 is raised, for example to remove waste containers 2504, the portion of connecting tube 2518 between first joint 2528 and drain tube 2508 is raised above the portion of connecting tube 2518 between second joint 2530 and vertical connecting member 2526 while the portion of connecting tube 2518 between first joint 2528 and second joint 2530 has a sloped-up orientation. Connecting tube 2516 may further be jointed similar to connecting tube 2518. FIGS. 25A, 25B and 25C illustrate an embodiment where drain tube 2508 is raised and in turn connecting tube 2518 includes the raised and sloped-up portion previously discussed, while drain tube 2506 is lowered such that connecting tube 2516 has a sloped-down orientation. In the case of a flexible plastic tube, similar regions of connecting tubes 2516, 2518 may have raised and sloped orientations as previously discussed.

Flow of fluids through waste drain system 2500 is substantially a passive process driven primarily by gravity. As such, the ability to modify the orientation of connecting tubes 2516, 1518 helps to control a flow of fluid through drain tubes 2506, 2508 as well as fluid back up into the associated reaction stations. In particular, when drain tube 2506 is lowered and, in turn, connecting tube 2516 has a sloped-down configuration, gravity drives flow of a waste fluid from waste drain 2520 of the reaction station, through vertical connecting member 2524, and into connecting member 2516. Since connecting member 2516 is sloped-down, fluid drained from the reaction station easily flows into drain tube 2506 and is deposited within waste container 2502. When connecting member 2518 is in a sloped-up configuration (i.e. when drain tube 2508 is raised) fluid may stop flowing, and in some cases, begin to flow away from drain tube 2508 back toward waste drain 2522 of the associated reaction station. Stopping or reversing the flow of fluid may be desirable when, for example, waste container 2504 is being removed or replaced by another container as it prevents waste from dripping onto sensing plate 2514 and/or the operator. It is recognized, however, that when a level of fluid within connecting member 2518 reaches a level within vertical connecting member 2526 above the highest point of connecting member 2518 (e.g. joint 2528), fluid begins to flow in a direction of drain pipe 2508 so that the fluid does not flow back into the associated reaction station. Such feature is desirable, for example, where an operator forgets to lower drain tube 2508 into drain container 2504 before starting the processing operation. Once a sufficient level of fluid begins to collect within vertical connecting member 2526 (i.e. a fluid level above the highest point of connecting member 2518) the fluid will begin to flow through connecting member 2518 and into waste container 2504 via drain tube 2508, thereby preventing waste back up within the reaction station.

The algorithms and displays presented herein are not inherently related to any particular computer or other apparatus. Various general purpose systems may be used with programs in accordance with the teachings herein or it may prove convenient to construct a more specialized device to perform the described method. In addition, the invention is not described with reference to any particular programming language. It will be appreciated that a variety of programming languages may be used to implement the teachings of the invention as described herein.

A computer readable medium includes any mechanism for storing information in a form readable by a computer. For example, a computer readable medium includes read only memory ("ROM"), random access memory ("RAM"), magnetic disk storage media, optical storage media, flash memory devices or other type of machine-accessible storage media.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

In the foregoing specification, the invention has been described with reference to specific embodiments thereof. It will, however, be evident that various modifications and changes can be made thereto without departing from the broader spirit and scope of the invention as set forth in the appended claims. For example, a reagent cartridge as disclosed herein (e.g. reagent cartridge 408) may contain solvent or water instead of a reagent and used for purposes other than, for example, staining a sample on an underlying slide. The specification and drawings are, accordingly, to be regarded in an illustrative rather than a restrictive sense.

What is claimed is:

1. An apparatus comprising:
    a reagent cartridge comprising a housing that defines a reagent retaining recess and a reagent directing channel, the reagent retaining recess is fluidly connected to a first sloped surface connecting the reagent retaining recess to an outlet channel extending from a bottom side of the housing, and the reagent directing channel comprises a first inclined portion and a second inclined portion connecting the reagent directing channel to the outlet channel, the second inclined portion extends from the first inclined portion at a substantially right angle, and in a direction toward the first sloped surface, such that the first sloped surface and the second inclined portion converge with one another at the outlet channel, and wherein the reagent retaining recess comprises a sidewall and a ledge extending inwardly from the sidewall, wherein the ledge is dimensioned to support a reagent capsule removably positioned within the reagent retaining recess and fluidly couple the reagent capsule with the first sloped surface.

2. The apparatus of claim 1 wherein the first inclined portion and the second inclined portion have a same slope and a tubular rounded surface through which a fluid flows to the outlet channel.

3. The apparatus of claim 1 wherein a reagent capsule is positioned within the reagent retaining recess, and the reagent capsule comprises a collapsible container and a plunger dimensioned to break a seal of the container when the container is collapsed.

4. The apparatus of claim 1 wherein a reagent capsule is positioned within the reagent retaining recess, the apparatus further comprising a bracket assembly coupled to the capsule, the bracket assembly dimensioned to secure the capsule to the reagent cartridge.

5. The apparatus of claim 4 wherein the bracket assembly comprises a identifier identifying a reagent contained within the capsule.

6. The apparatus of claim 4 wherein the capsule is removably coupled to the bracket assembly.

7. An apparatus comprising:
a reagent cartridge comprising:
a housing that defines a reagent retaining recess and a reagent directing channel, the reagent retaining recess is fluidly connected to a first sloped surface connecting the reagent retaining recess to an outlet channel extending from a bottom side of the housing, and the reagent directing channel comprises a first inclined portion and a second inclined portion connecting the reagent directing channel to the outlet channel, the second inclined portion extends from the first inclined portion at a substantially right angle, and in a direction toward the first sloped surface, such that the first sloped surface and the second inclined portion converge with one another at the outlet channel;
a reagent capsule positioned within the reagent retaining recess; and
a bracket assembly coupled to the capsule, the bracket assembly configured to secure the capsule to the reagent cartridge, wherein the bracket assembly comprises an identifier identifying a reagent contained within the capsule.

8. The apparatus of claim 7 wherein the first inclined portion and the second inclined portion have a same slope and a tubular rounded surface through which a fluid flows to the outlet channel.

9. The apparatus of claim 7 wherein the reagent capsule comprises a collapsible container and a plunger dimensioned to break a seal of the container when the container is collapsed.

10. The apparatus of claim 7 wherein the capsule is removably coupled to the bracket assembly.

* * * * *